United States Patent
Degertekin

(10) Patent No.: US 8,220,318 B2
(45) Date of Patent: Jul. 17, 2012

(54) FAST MICROSCALE ACTUATORS FOR PROBE MICROSCOPY

(75) Inventor: Fahrettin Levent Degertekin, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1386 days.

(21) Appl. No.: 11/777,518

(22) Filed: Jul. 13, 2007

(65) Prior Publication Data

US 2011/0170108 A1  Jul. 14, 2011

Related U.S. Application Data

(63) Continuation-in-part of application No. 11/260,238, filed on Oct. 28, 2005.

(60) Provisional application No. 60/830,445, filed on Jul. 13, 2006, provisional application No. 60/707,219, filed on Aug. 11, 2005, provisional application No. 60/691,972, filed on Jun. 17, 2005.

(51) Int. Cl.
*G01B 5/28* (2006.01)

(52) U.S. Cl. ......................................... 73/105
(58) Field of Classification Search ...................... 73/105
See application file for complete search history.

(56) References Cited

U.S. PATENT DOCUMENTS

| 5,247,186 | A | 9/1993 | Toda |
| 5,253,515 | A | 10/1993 | Toda et al. |
| 5,445,011 | A | 8/1995 | Ghislain et al. |
| 5,553,486 | A * | 9/1996 | Bonin ........................... 73/105 |
| 5,576,483 | A * | 11/1996 | Bonin ........................... 73/105 |
| 5,900,729 | A | 5/1999 | Moser et al. |
| 5,923,033 | A | 7/1999 | Takayama et al. |
| 6,249,747 | B1 | 6/2001 | Binnig et al. |
| 6,272,907 | B1 | 8/2001 | Neukermans et al. |
| 6,291,927 | B1 | 9/2001 | Percin et al. |
| 6,400,166 | B2 | 6/2002 | Babson et al. |
| 6,567,572 | B2 | 5/2003 | Degertekin et al. |
| 6,672,144 | B2 | 1/2004 | Adderton et al. |
| 6,676,813 | B1 | 1/2004 | Pelekhov et al. |
| 6,836,112 | B2 | 12/2004 | Hennessy |
| 6,862,923 | B2 | 3/2005 | Buguin et al. |
| 6,862,924 | B2 | 3/2005 | Xi et al. |

(Continued)

FOREIGN PATENT DOCUMENTS

JP  05248810 A  9/1993

(Continued)

OTHER PUBLICATIONS

Solgaard, et al., "Deformable Grating Optical Modulator," Optics Letters, vol. 17, No. 9, May 1, 1992, pp. 688-690.

(Continued)

*Primary Examiner* — Daniel Larkin
(74) *Attorney, Agent, or Firm* — Bryan W. Bockhop; Bockhop & Associates, LLC

(57) ABSTRACT

A system for measuring a property of a sample includes an actuation device disposed on a substrate and includes a flexible surface spaced apart from the substrate and configured so as to allow placement of the sample thereupon. The actuation device also includes a vertical actuator that is configured to cause the flexible surface to achieve a predetermined displacement from the substrate when a corresponding potential is applied thereto. A sensing probe is disposed so as to be configured to interact with the sample thereby sensing the property of the sample.

12 Claims, 32 Drawing Sheets

U.S. PATENT DOCUMENTS

| | | |
|---|---|---|
| 6,882,429 B1 | 4/2005 | Weitekamp et al. |
| 2001/0000279 A1 | 4/2001 | Daniels et al. |
| 2001/0013574 A1 | 8/2001 | Warren et al. |
| 2001/0035700 A1 | 11/2001 | Percin et al. |
| 2001/0049959 A1 | 12/2001 | Neukermans et al. |
| 2003/0042409 A1 | 3/2003 | Warren et al. |
| 2004/0065821 A1 | 4/2004 | Warren et al. |
| 2004/0206165 A1 | 10/2004 | Minne et al. |
| 2004/0216517 A1 | 11/2004 | Xi et al. |
| 2005/0066714 A1 | 3/2005 | Adderton et al. |
| 2005/0180678 A1 | 8/2005 | Panepucci et al. |

FOREIGN PATENT DOCUMENTS

| | | |
|---|---|---|
| JP | 07065428 A | 3/1995 |
| JP | 10090287 A | 4/1998 |
| JP | 2004093574 A | 3/2004 |

OTHER PUBLICATIONS

DeWitt et al., "Range-finding Method Using Diffraction Gratings," Applied Optics, vol. 34, No. 14, May 10, 1995, pp. 2510-2521.

* cited by examiner

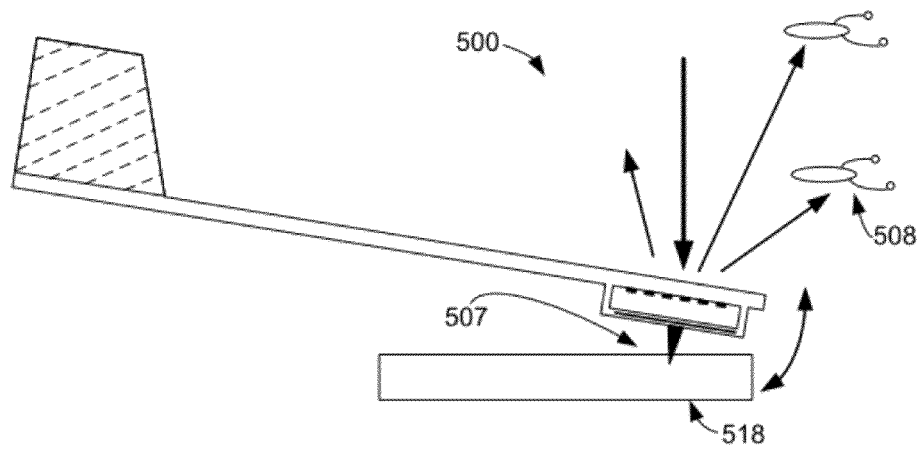
FIG. 5A
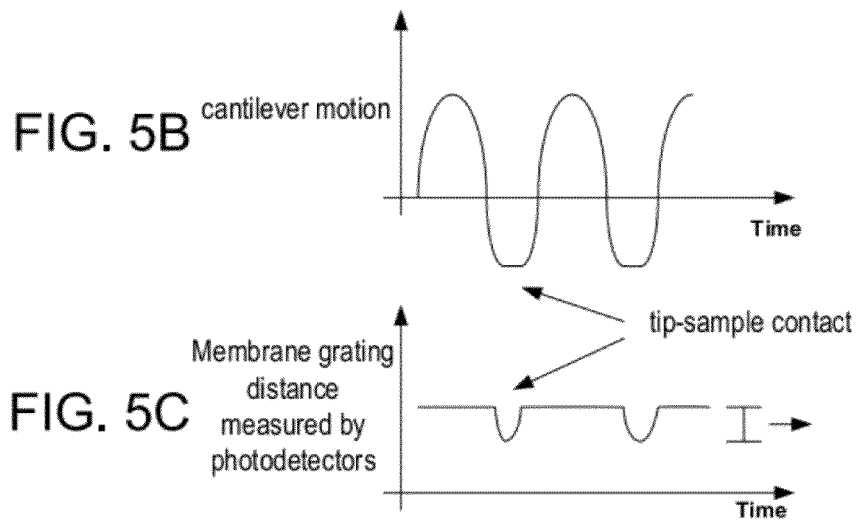
FIG. 5B cantilever motion
FIG. 5C Membrane grating distance measured by photodetectors
tip-sample contact

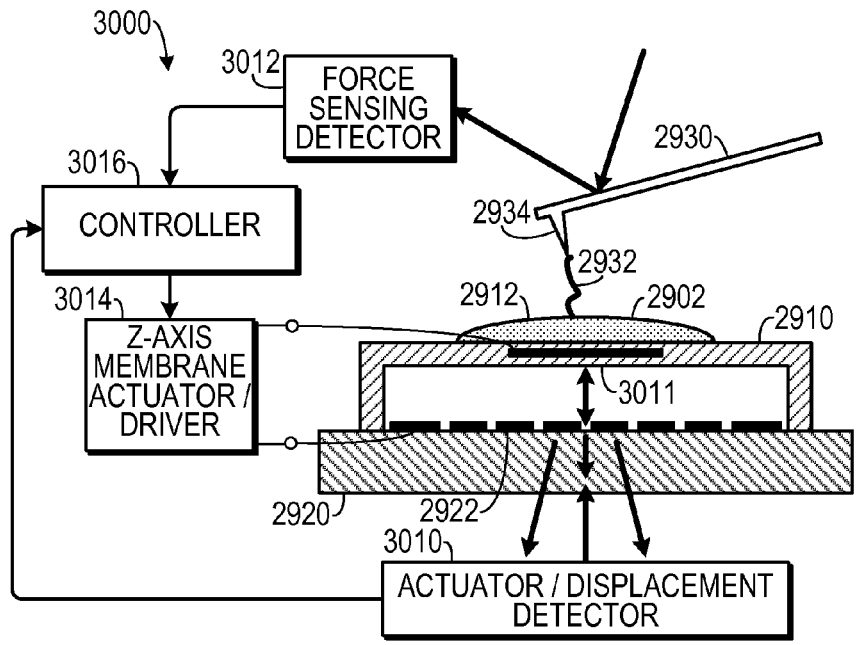
FIG. 30
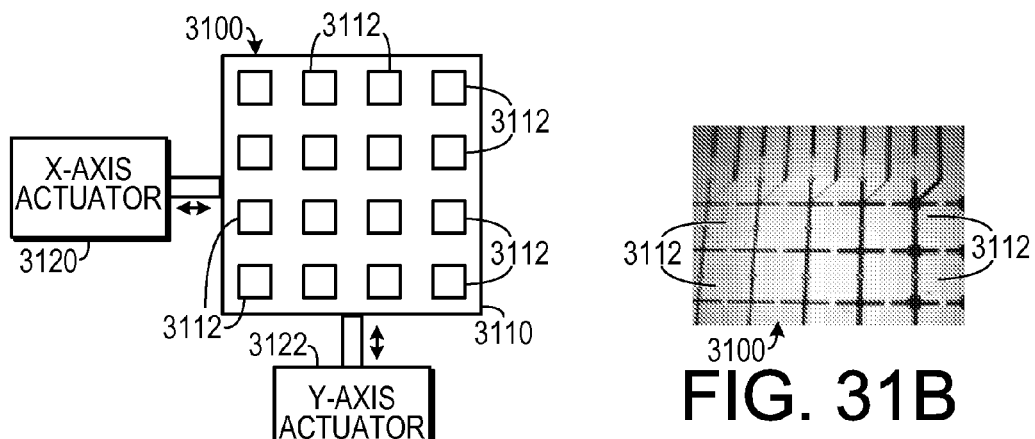
FIG. 31A
FIG. 31B
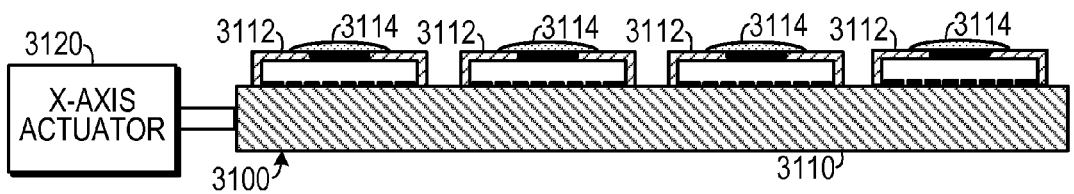
FIG. 31C

FAST MICROSCALE ACTUATORS FOR PROBE MICROSCOPY

CROSS-REFERENCE TO RELATED APPLICATION(S)

This application claims the benefit of U.S. Provisional Patent Application Ser. No. 60/830,445, filed Jul. 13, 2006, the entirety of which is hereby incorporated herein by reference. This application is also a continuation-in-part of, and claims the benefit of, U.S. patent application Ser. No. 11/260,238, filed Oct. 28, 2005, which is a non-provisional application claiming priority on U.S. Provisional Patent Application Ser. No. 60/691,972 filed on Jun. 17, 2005, and U.S. Provisional Patent Application Ser. No. 60/707,219 filed on Aug. 11, 2005, the entirety of each of which is hereby incorporated herein by reference.

STATEMENT OF GOVERNMENT INTEREST

This invention was made with support from the U.S. government under grant number ECS 0348582, awarded by National Science Foundation and grant number 1 R01 A1060799-01A2, awarder by the National Institutes of Health. The government may have certain rights in the invention.

BACKGROUND OF THE INVENTION

1. Field of the Invention

The present invention relates to probe sensing and, more specifically, to a system for controlling spacing in a probe sensor system with a high level of precision.

2. Description of the Prior Art

Conventional atomic force microscope (AFM) and its variations have been used to probe a wide range of physical and biological processes, including mechanical properties of single molecules, electric and magnetic fields of single atoms and electrons. Moreover, cantilever based structures inspired by the AFM have been a significant driver for nanotechnology resulting in chemical sensor arrays, various forms of lithography tools with high resolution, and terabit level data storage systems. Despite the current rate of success, the AFM needs to be improved in terms of speed, sensitivity, and an ability to generate quantitative data on the chemical and mechanical properties of the sample. For example, when measuring molecular dynamics at room temperature, the molecular forces need to be measured in a time scale that is less than the time of the thermal fluctuations to break the bonds. This requires a high speed system with sub-nanonewton and sub-nanometer sensitivity.

Current cantilever-based structures for AFM probes and their respective actuation methodologies lack speed and sensitivity and have hindered progress in the aforementioned areas. Imaging systems based on small cantilevers have been developed to increase the speed of AFMs, but this approach has not yet found wide use due to demanding constraints on optical detection and bulky actuators. Several methods have been developed for quantitative elasticity measurements, but the trade-off between force resolution, measurement speed, and cantilever stiffness has been problematic especially for samples with high compliance and high adhesion. Cantilever deflection signals measured during tapping mode imaging have been inverted to obtain elasticity information with smaller impact forces, but complicated dynamic response of the cantilever increases the noise level and prevents calculation of the interaction forces. Arrays of AFM cantilevers with integrated piezoelectric actuators have been developed for parallel lithography, but low cantilever speed and complex fabrication methods have limited their use.

Most of the scanning probe microscopy techniques, including tapping mode imaging and force spectroscopy, rely on measurement of the deflection of a micro-cantilever with a sharp tip. Therefore, the resulting force data depend on the dynamic properties of the cantilever, which shapes the frequency response. This can be quite limiting, as mechanical structures like cantilevers are resonant vibrating structures and they provide information mostly only around these resonances. For example, in tapping mode imaging it is nearly impossible to recover all the information about the tip-sample interaction force, since the transient force applied at each tap cannot be observed as a clean time signal.

Moreover, conventional methods of imaging with scanning probes can be time consuming while others are often destructive because they require static tip-sample contact. Dynamic operation of AFM, such as the tapping-mode, eliminates shear forces during the scan. However, the only free variable in this mode, the phase, is related to the energy dissipation and it is difficult to interpret. Further, the inverse problem of gathering the time-domain interaction forces from the tapping signal is not easily solvable due to complex dynamics of the AFM cantilever. Harmonic imaging is useful to analyze the sample elastic properties, but this method recovers only a small part of the tip-sample interaction force frequency spectrum.

Applications of atomic force microscopy (AFM) in life sciences have been increasing in both variety and significance. In addition to high resolution imaging of cells, DNA and other biological structures, AFM enables single-molecule mechanics studies characterizing both intra-molecular and intermolecular forces. Studying biological samples in aqueous environments, which can be corrosive and electrically conducting, imposes challenging electrical isolation requirements. This is especially important for AFM cantilevers or cantilever arrays with integrated piezoelectric detectors or piezoelectric actuators. To collect statistically significant data even on a single type of molecule, measurements need to be repeated many times, which requires durable sensors. To implement single-molecule experiments to protein chips for applications such as drug discovery and screening, the throughput needs to be significantly improved. This can be achieved by development of systems that can perform parallel single-molecule measurements on many different molecular pairs. Some parallel techniques have been demonstrated for bond rupture frequency measurements where a molecule of known mechanical properties is used as a force gauge. However, many other single-molecule experiments, such as those that measure bond lifetime at a clamped force, require applying controlled forces on molecules and measuring these forces with pico-Newton resolution. Therefore, both parallel actuation and parallel force sensing are required for parallel single-molecule mechanics experiments. AFM cantilever arrays with integrated piezoelectric actuators and either optical or piezo-resistive sensing have demonstrated this capability. These devices, which are used mainly for fast imaging so far, require complex fabrication processes and may be difficult to isolate electrically for operation in liquid environments.

Recently, membrane-based probe structures with electrostatic actuation and integrated diffraction-based optical interferometric displacement detection have been introduced for SPM applications. Initial implementation of these force sensing integrated readout and active tip (FIRAT) devices used aluminum membranes over an unsealed air cavity and hence was not suitable for operation in immersion. A version of these surface micromachined structures suitable for operation in biologically relevant, electrically conductive buffer solutions has already been realized for medical ultrasonic imaging applications. These capacitive micromachined ultrasonic transducers (CMUT) use a dielectric material such as silicon nitride as the structural membrane, and a metal actuation electrode buried in the dielectric membrane which is electrically isolated from the immersion medium. The cavity between the membrane and the bottom electrode is sealed under low pressure to prevent liquid leakage.

Thus, there is a need to overcome these and other problems of the prior art associated with probe microscopy.

SUMMARY OF THE INVENTION

The disadvantages of the prior art are overcome by the present invention which, in one aspect, is an apparatus for measuring a property of a sample. An actuation device is disposed on a substrate and includes a flexible surface spaced apart from the substrate and configured so as to allow placement of the sample thereupon. The actuation device also includes a vertical actuator that is configured to cause the flexible surface to achieve a predetermined displacement from the substrate when a corresponding potential is applied thereto. A sensing probe is disposed so as to be configured to interact with the sample thereby sensing the property of the sample.

In another aspect, the invention is a sensing structure for sensing a property of a sample. A force sensing detector detects a state of a force sensor. An actuation device upon which the sample may be placed has a flexible surface and is spaced apart from a substrate. An actuation device driver controls a displacement of the flexible surface from the substrate by applying a potential to the actuation device. An actuation device displacement sensor detects the displacement of the flexible surface from the substrate. A control circuit is responsive to the force sensing detector and the actuation device displacement sensor. The control circuit directs control information to the actuation device driver so as to cause the displacement of the flexible surface to be a predetermined displacement.

In another aspect, the invention is a parallel force spectroscopy apparatus that includes an array of sensing probes that are each capable of sensing a property of a sample. An array of actuation devices each includes a flexible surface that is spaced apart from a substrate. The array of actuation devices is disposed so that each of the actuation devices is configured to interact with exactly one of the sensing probes. A control circuit is configured to apply a potential to each of the actuation devices so as to control displacement of the flexible surface from the substrate.

In yet another aspect, the invention is a method of detecting a property of a sample, in which the sample is placed on an actuator that includes a flexible actuation surface that is spaced apart from a substrate. A sensing probe is placed in a position so as to be configured to interact with the sample. The flexible actuation surface is moved relative to the substrate so that the sample interacts with the sensing probe. Interaction between the sensing probe and the sample is sensed so as to detect the property of the sample.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

The following is a brief description of the Figures of the Drawings. Unless otherwise stated, the drawings are not necessarily drawn to scale.

FIG. 5A shows a cross-sectional schematic diagram of another exemplary force sensor in accordance with the present teachings.

FIG. 5B is a graph plotting cantilever motion versus time for an exemplary force sensor in accordance with the present teachings.

FIG. 5C is a graph plotting flexible mechanical structure grating-distance versus time for an exemplary force sensor in accordance with the present teachings.

FIG. 8B shows a graph plotting voltage output versus time for a tapping cantilever for a force sensor in accordance with the present teachings.

FIG. 8C shows a close up of a portion of the graph shown in FIG. 8B.

FIG. 17A shows a topographical image of a sample using an exemplary force sensor in accordance with the present teachings.

FIG. 17B shows line scans of the sample shown in FIG. 17A measured at different speeds.

FIG. 20A shows a graph plotting photo-detector output versus bias voltage for a force sensor in accordance with the present teachings.

FIG. 20B shows a graph plotting photo-detector output versus time for a force sensor in accordance with the present teachings.

FIG. 24A shows a graph plotting detector output bias voltage using a force sensor in accordance with the present teachings.

FIGS. 24B and 24C show graphs plotting detector output bias voltage using a force sensor in accordance with the present teachings.

FIG. 30 is a schematic drawing of a feedback actuation and sensing system.

FIG. 31A is a schematic drawing of an array of flexible-surface actuators and lateral actuators.

FIG. 31B is a micrograph of an array of flexible-surface electrostatic actuators.

FIG. 31C is a schematic drawing of a cross section of the array shown in FIG. 31A.

DETAILED DESCRIPTION OF THE INVENTION

Figure 1A:
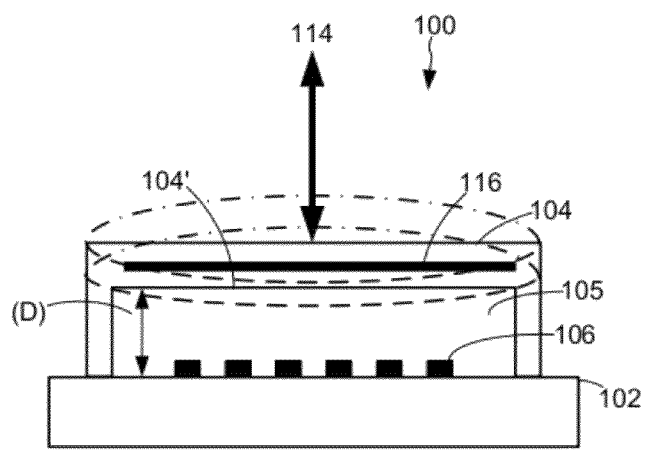
FIG. 1A shows a cross-sectional schematic diagram of an exemplary force sensor in accordance with the present teachings.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, I., 1 to 5.

One representative embodiment of the invention includes FIRAT structures for parallel single molecular force spectroscopy and SPM applications and a fabrication procedure of sealed membrane probe arrays on quartz substrates using a low temperature plasma-enhanced chemical vapor deposition (PECVD) dielectric film and a polymer sacrificial layer. Biomolecular bond unbinding force measurements are performed by pulling the molecules using individually actuated membranes, thereby eliminating the need for the piezoelectric actuator. Therefore, we have demonstrated the feasibility for using these devices in parallel single-molecule mechanics experiments.

According to various embodiments there is a force sensor for use in, for example, probe based instruments, such as probe microscopy and structure manipulation. The force sensor can comprise a detection surface, a flexible mechanical structure, and a gap between the detection surface and the flexible mechanical structure. The force sensors can also comprise a tip in contact with the flexible mechanical structure.

Force sensors described herein can eliminate the corruption of utility, such as measurement information, that can arise from a cantilever. These force sensors can also be used as actuators to apply known forces, providing clean and valuable elasticity information data on surfaces, biomolecules, and other materials. Moreover, these force sensors can be integrated on cantilevers and can be compatible with existing AFM systems while providing accurate tip displacement and also act as "active tips."

According to various embodiments, a displacement measurement can be made using a flexible mechanical structure, such as a membrane, a diaphragm, a cantilever, a clamped-clamped beam, a flexible structure comprising multiple flexible elements partially or totally fixed at one end on a substantially rigid surface and connected at a point so as to form a symmetry axis. These flexible mechanical structures can be micro-machined. These flexible mechanical structures can have uniform or non-uniform cross sections to achieve desired static and dynamic deflection characteristics. For example, the vibration modes that are symmetric and anti-symmetric with respect to the symmetry axis can be used to detect forces in different directions. These flexible mechanical structures can be made of metals such as gold, aluminum, or a semiconductor such as single crystal silicon or polycrystalline silicon, or dielectric materials such as silicon nitride, silicon oxide, or a polymer such as SU-8, or they can be a composite structure of metallic, semiconducting, polymer, or dielectric materials. While not intending to be so limited, measurements can be made to detect, for example: localized forces, such as, a force experienced by a tip contacting the flexible mechanical structure; surface topography using for example, a flexible mechanical structure with an integrated tip contacting a surface; a flexible mechanical structure with an integrated tip in close proximity of a surface or substance; and forces between a reactive substance, such as a molecule, bound to the flexible mechanical structure and another reactive substance, such as a molecule, bound on a close by structure such as a tip.

According to various embodiments, the detection surface can be a surface of a rigid substrate, or a part of a rigid substrate, with an optically reflective diffraction grating, a part of a rigid substrate with a reflective and/or electrically conductive diffraction grating for optical interferometric detection and electrostatic actuation, a part of a rigid substrate with electrically conductive members for electrostatic actuation and capacitive detection, a surface of a rigid substrate with a semi-transparent layer for optical interferometry. In some cases the detection surface can be a surface of a deformable mechanical structure such as a membrane, clamped-clamped beam or a cantilever. The rigidity of the mechanical structure with the detection surface can be substantially higher than the flexible mechanical structure of the force sensor. The detection surface can contain conductive and dielectric portions to have electrical isolation between actuation and detection electrodes. In some cases, the deformable detection surface can be actuated and therefore it can contain a separate electrode or piezoelectric film for actuation purposes. Still further, in some cases the detection surface can form a substrate.

According to various embodiments, displacement can be measured using interferometric techniques or capacitive techniques. For example, a grating, such as that used in a diffraction based optical interferometric method or any other optical interferometric method such as, for example, Fabry-Perot structures, an example of which is described in U.S. patent application Ser. No. 10/704,932, filed Nov. 10, 2003, now U.S. Pat. No. 7,116,430, which is incorporated herein by reference in its entirety, can be used. Capacitive measurements can use techniques used to monitor capacitance, such as that used in capacitive microphones.

The flexible mechanical structure dimensions and materials can be adjusted to have desired compliance and measurement capabilities to make static and dynamic measurements with sufficient bandwidth. The overall shape of the flexible mechanical structure can be circular, square, or any other suitable shape. Typical lateral dimensions can be from 10 μm to 2 mm, flexible mechanical structure thickness can be from 10 nm to 3 μm, and the gap can be from 1 nm to 10 μm. In some embodiments the gap can be as large as 1 mm. The flexible mechanical structure material can comprise, for example, aluminum, gold, silicon nitride, silicon, silicon oxide, or polysilicon or can be a composite structure of metallic, semiconducting, and dielectric materials. The gap can be sealed or partially sealed for applications in liquids, or it can be open for vacuum and atmospheric measurements.

For some force measurements, a soft cantilever may not be required. Using the output from the force sensors in a feedback loop, one can use an external actuator to individually adjust the tip-flexible mechanical structure, tip-sample distances. According to various embodiments, the flexible mechanical structure can be electrostatically actuated to apply desired forces. According to various embodiments, force sensors described herein can be attached to a cantilever to form a force sensor structure. Further, the force sensor structure can be combined with a detector to form a force sensor unit that can be used in a probe based instrument.

FIG. 1A shows a cross-sectional schematic diagram of an exemplary force sensor 100 in accordance with the present teachings. The force sensor 100 comprises a detection surface 102 and a flexible mechanical structure 104. The flexible mechanical structure 104 can be disposed distance (D) above the detection surface so as to form a gap 105 between the flexible mechanical structure 104 and the detection surface 102. The flexible mechanical structure can be configured to move to a new position 104' upon exposure to an external stimuli 114, such as a force. Moreover, the force sensor 100 can include elements configured to detect changes in the distance (D). Still further, the force sensor 100 can be actuated to affect the distance (D) using, for example, bottom electrode 106, such as a grating, and a top electrode 116, both of which are described in more detail below.

The detection surface 102 can be made of a material transparent to predetermined wavelengths of light. For example, the detection surface can be made from silicon oxide, such as quartz. The overall shape of the flexible mechanical structure 104 can be circular, square, or any other suitable shape. Typical diameters of flexible mechanical structure 104 can range from 5 μm to 2 mm and the thickness of flexible mechanical structure 104 can be from 10 nm to 10 μm. The flexible mechanical structure can be a micro-machined material that can comprise, for example, aluminum, gold, silicon nitride, silicon oxide, or polysilicon.

According to various embodiments, the distance (D) of gap 105 can be from 50 nm to 50 μm. Moreover, the gap 105 can be sealed for applications in liquids, or it can be open for vacuum and atmospheric measurements. In some embodiments, the gap can be formed by the flexible mechanical structure can be supported over the detection surface by at least one sidewall. Movement of the flexible mechanical structure, or displacement measurements, can be made, for example using a grating as described below, that uses a diffraction based optical interferometric method or any other optical interferometric method or a capacitive method, such as in that used in capacitive microphones can be used for detection. According to various embodiments, grating periods of the grating 106 can range from about 0.5 μm to about 20 μm. The incident light can be from the UV (with wavelengths starting at about 0.2 μm) to IR (with wavelengths starting at about 1.5 μm).

Figure 1B:
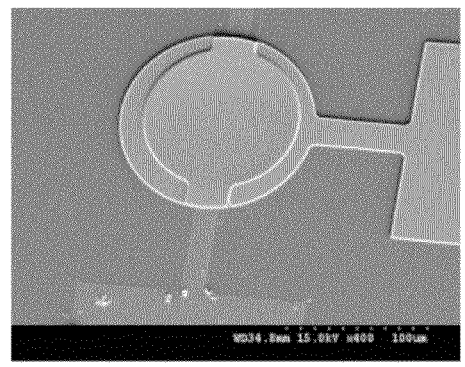
FIG. 1B shows a scanning electron microscope (SEM) picture of an exemplary force sensor in accordance with the present teachings.
Figure 1C:
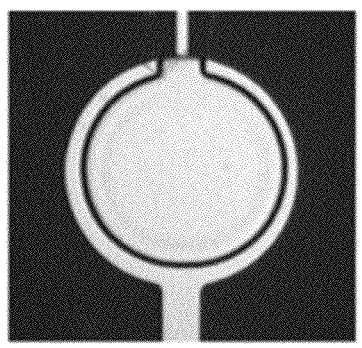
FIG. 1C shows a photograph of a top down view of a force sensor in accordance with the present teachings.
Figure 1D:
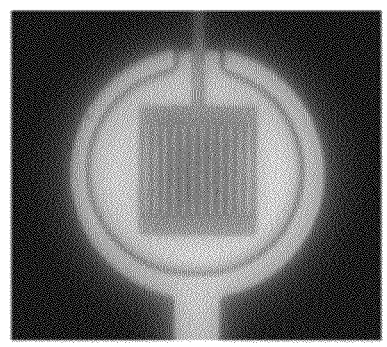
FIG. 1D shows a photograph of a bottom up view of a force sensor in accordance with the present teachings.

FIGS. 1B-1D show various perspective views of exemplary force sensors. For example, FIG. 1B shows a view using a scanning electron microscope (SEM) of the sensor 100. FIG. 1B is a top down photographic view of the force sensor 100 and shows flexible mechanical structure 104. FIG. 1D is a photographic view of the force sensor 100 as seen by passing light through the transparent detection surface 102 and shows grating 106 positioned under the flexible mechanical structure 104.

Figure 1E:
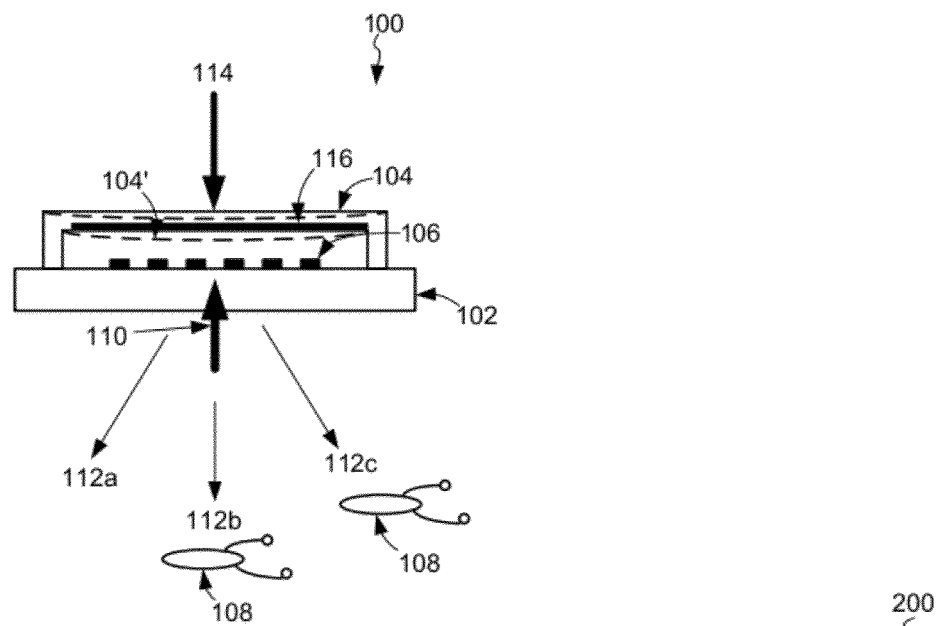
FIG. 1E shows a cross-sectional schematic diagram of another exemplary force sensor in accordance with the present teachings.

According to various embodiments, the force sensor 100 can also include a grating 106, as shown in FIG. 1E. In FIG. 1E, a beam of light 110 can be directed through the detection surface 102 to impinge on the flexible mechanical structure 104 and the grating 106. According to various embodiments, the beam of light can be directed at the detection surface 102 at an angle, such as, in the range of, for example +10o away from normal to the detection surface 102. A portion of the flexible mechanical structure 104 can be reflective such that light 110 can be reflected from the flexible mechanical structure 104 and another portion can be reflected by the grating 106. As a result, different diffraction orders with different intensity levels can be generated as the light passes through the grating 106 depending on the gap thickness.

For example, FIG. 1E shows first diffraction order light 112 reflected from the grating 106 and the flexible mechanical structure 104. The diffracted light 112 can be detected by a detector 108. It is to be understood that alternatively, the detectors can be used to detect changes in capacitance due to changes in the gap 105.

As shown in FIG. 1E, a stimuli 114, such as a force, can be applied to the flexible mechanical structure 104. The stimuli 114 causes the flexible mechanical structure 104 to bend, or flex, shown as 104'. According to various embodiments, the flexible mechanical structure 104 can bend in various directions, such as toward the detection surface 102 or away from the detection surface 102. Bending the flexible mechanical structure 104 causes the thickness (D) of the gap 105 shown in FIG. 1A to change.

When using a beam of light, the light 110 is reflected in a different direction when the flexible mechanical structure is in the bent position 104' than when the flexible mechanical structure is in the rest position 104. Further, light 110 reflected from the bent flexible mechanical structure 104' interacts differently with the grating 106 to produce changes in the intensity of different diffraction orders, shown in FIG. 1E as 112a-112c. The detectors 108 can then detect the intensity of the diffracted light output from the grating 106. This provides a robust, micro-scale interferometer structure. Generally, information obtained from the detectors 108 can be used to determine the stimuli 114, such as the amount of force, applied to the flexible mechanical structure 104. This determination can be done using a computer processor (not shown) or other various techniques as will be known to one of ordinary skill in the art. Also shown in FIG. 1E is a top electrode 116 that can cooperate with, for example grating 106, to serve as an actuator, as will be described in detail below.

According to various embodiments the detector 108 can be a photo-detector, such as a silicon photodiode operated in photovoltaic or reverse biased mode or another type of photo-detector sensitive in the wavelength range of the light source. Moreover, the light 110 can be a coherent light source such as a laser. Exemplary light sources can include, but are not limited to, helium neon type gas lasers, semiconductor laser diodes, vertical cavity surface emitting lasers, light emitting diodes.

Figure 2A:
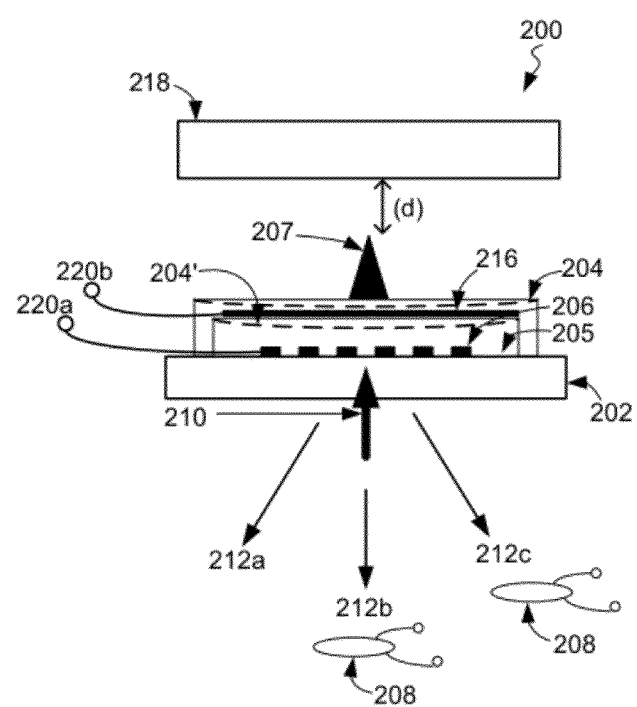
FIG. 2A shows a cross-sectional schematic diagram of another exemplary force sensor in accordance with the present teachings.

FIG. 2A shows a cross-sectional schematic diagram of another exemplary force sensor 200 in accordance with the present teachings. The force sensor 200 comprises a detection surface 202, a flexible mechanical structure 204, a grating 206, and a tip 207. In some embodiments, the force sensor 200 can also include a top electrode 216. Moreover, the grating 206 can be covered with a dielectric layer to prevent electrical shorting in case of flexible mechanical structure collapse.

Generally, the force sensor 200 can be used to manipulate structures, such as atoms, molecules, or micro-electro-mechanical systems (MEMs) or to characterize various material properties of a sample 218. For example, the topography of the sample 218 can be determined by moving the sample 218 in a lateral direction across the tip 207. It is also contemplated that the sample 218 can remain stationary and the tip 207 can be moved relative to the sample 218. Changes in height of the sample 218 are detected and cause the tip 207 to move accordingly. The force on the tip 207 caused by, for example the tip motion, can cause the flexible mechanical structure 204 to bend, or flex as shown by 204'. Light 210 can also be directed through detection surface 202 to impinge on the flexible mechanical structure 204. The light 210 is reflected from the flexible mechanical structure and diffracted by the grating 206. As the tip 207 applies force to the flexible mechanical structure, the thickness of the gap 205 changes. This can cause the reflected light to diffract differently than if the flexible mechanical structure were in its un-bent position. Thus, different diffraction orders intensity can change depending on the gap thickness.

After passing through the grating 206 the diffracted light 212a-c can be detected by the detectors 208. The output from the flexible mechanical structure 204 can be used in a feedback loop to direct an external actuator (not shown) to adjust the tip-flexible mechanical structure distance (i.e., the gap thickness), and thus the tip-sample distance (d). The flexible mechanical structure 204 can be electrostatically actuated to apply desired forces or to adjust the tip-flexible mechanical structure distance (i.e., the gap thickness), and thus the tip-sample distance (d) by biasing electrodes 220a and 220b attached to the grating 206 and the top electrode 216, respectively. Although two detectors are shown in FIG. 2A, one of ordinary skill in the art understands that one or more detectors can be used.

According to various embodiments, the force sensor 200 can form an integrated phase-sensitive diffraction grating structure that can measure the flexible mechanical structure 204 and/or tip 207 displacement with the sensitivity of a Michelson interferometer. The displacement of the tip 207 due to stimuli acting on it can be monitored by illuminating the diffraction grating 206 through the transparent detection surface 202 with a coherent light source 210 and the intensity of the reflected diffraction orders 212a-c can be recorded by the detectors 208 at fixed locations. The resulting interference curve is typically periodic with $\lambda/2$, where $\lambda$ is the optical wavelength in air. According to an exemplary embodiment, the displacement detection can be within the range of about $\lambda/4$ (167.5 nm for $\lambda=670$ nm) in the case of a fixed grating 206. However, the detection surface 202 and the grating 206 can be moved by suitable actuators to extend this imaging range. Furthermore, the grating 206 can be located not at the center but closer to the clamped edges of the flexible mechanical structure to increase the equivalent detectable tip motion range. In the case of a microscope, the "active" tip can be moved by electrostatic forces applied to the flexible mechanical structure 204 using the diffraction grating 206 as an integrated rigid actuator electrode. In some applications, this actuator can be used to adjust the tip 207 position for optimal displacement sensitivity to provide a force feedback signal to an external actuator moving the transparent detection surface 202.

In some embodiments, such as applications requiring high speeds, this integrated actuator can be used as the only actuator in the feedback loop to move the tip 207 with a speed determined by the flexible mechanical structure 204 dynamics both in liquids and in air.

Figure 2B:
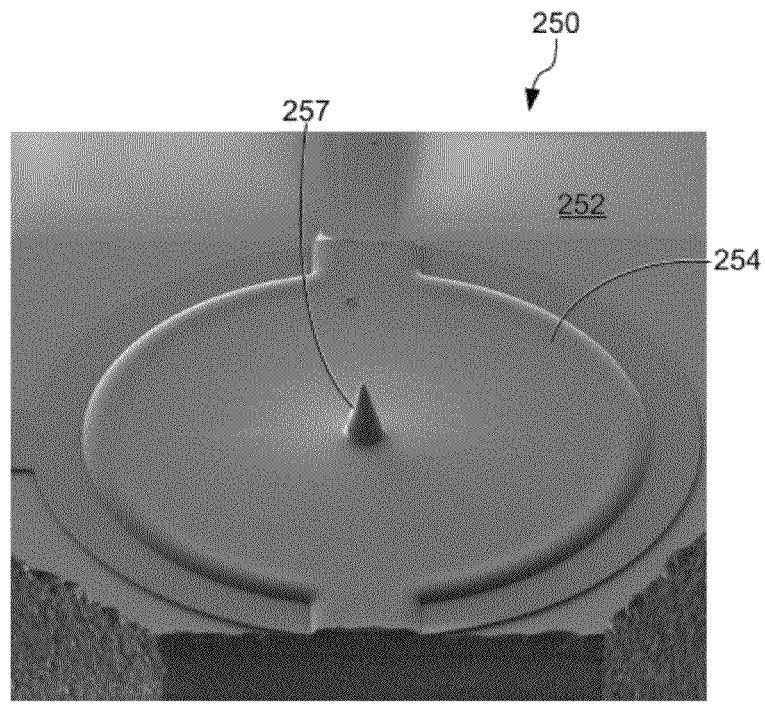
FIG. 2B shows a scanning ion beam image of another exemplary force sensor in accordance with the present teachings.
Figure 2C:
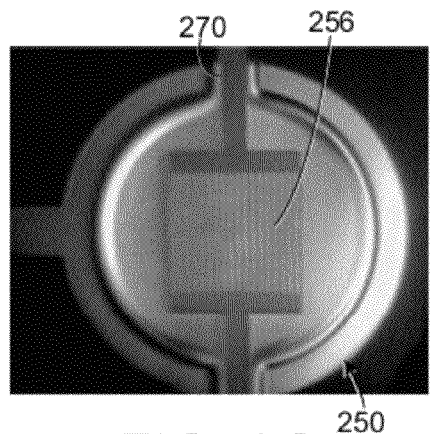
FIG. 2C shows photograph of a bottom up view of a force sensor in accordance with the present teachings.
Figure 2D:
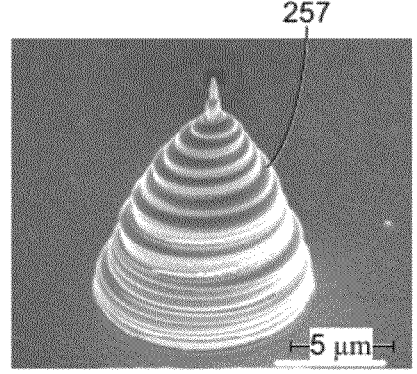
FIG. 2D shows a scanning electron microscope (SEM) picture of a force sensor tip in accordance with the present teachings.

FIG. 2B shows a focused ion beam (FIB) micrograph of a force sensor 250 according to an exemplary embodiment. In the embodiment shown in FIG. 2B, the flexible mechanical structure 254 is 0.9 μm thick and is made from aluminum. Moreover, the flexible mechanical structure 254 is 150 μm in diameter and it can be formed by sputter deposition on a 0.5 mm thick quartz substrate over a 1.4 μm thick photoresist sacrificial layer. FIG. 2C shows the optical micrograph of the flexible mechanical structure 254 from the backside as seen through the substrate 252. The grating 256 and the electrical connections 270 can be seen as well as the darker spot at the position of the tip 257 at the middle of the flexible mechanical structure 254. In FIG. 2B, the 90 nm thick aluminum grating 256 can be formed by evaporation over a 30 nm thick titanium or titanium nitride adhesion layer and then patterned to have 4 μm grating period with 50% fill factor. A 220 nm thick oxide layer can be deposited over the grating 256 using plasma enhanced chemical vapor deposition. In this case, the subsequent flexible mechanical structure stiffness was measured to be approximately 133 N/m using a calibrated AFM cantilever and the electrostatic actuation range was approximately 470 nm before collapse. The tip 257 was fabricated out of platinum using an FIB. The process involved ion beam assisted chemical vapor deposition of platinum using methyl platinum gas where molecules adsorb on the surface but only decompose where the ion beam interacts. The tip 257, with a radius of curvatures down to 50 nm on the aluminum flexible mechanical structures 254, were fabricated with this method. An SEM micrograph of a typical tip with 70 nm radius of curvature is shown in FIG. 2D. According to various embodiments, the force sensor 200 can have a compact integrated electrostatic actuator, where the electric field between the grating electrode 206 and the top electrode 216 is contained within the gap 205. This structure can be replicated to form planar arrays of sensors, as described in more detail below, with good electrical and mechanical isolation. With a suitable set of flexible mechanical structure and electrode materials, the device can be operated in a dielectric or conductive fluid. According to various embodiments, the electrostatic forces may act only on the probe flexible mechanical structure 204. As such, the actuation speed can be quite fast. Therefore, combined with array operations, the force sensor can be used in probe applications that call for high speeds.

Figure 3A:
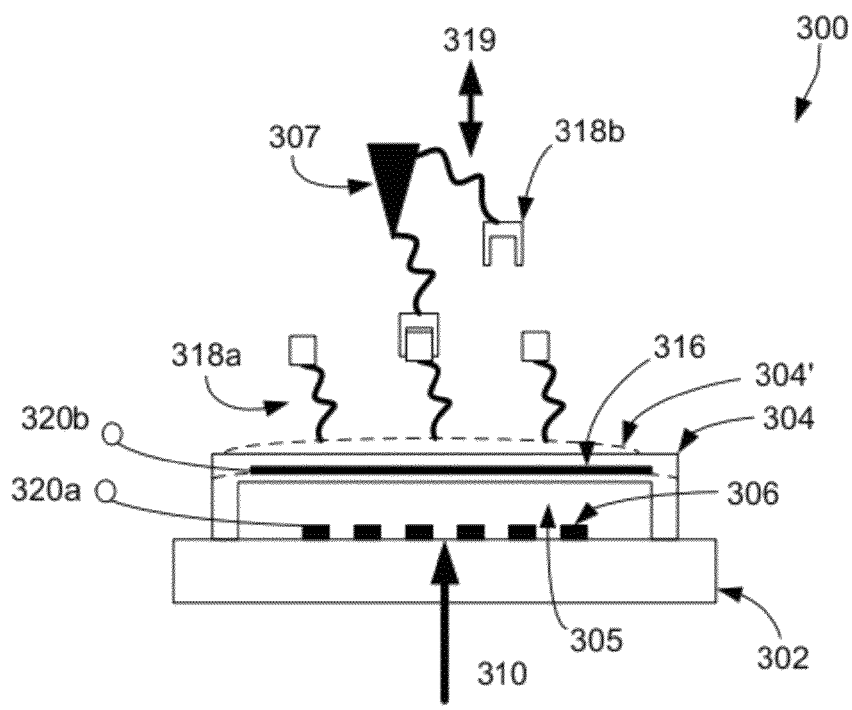
FIG. 3A shows a cross-sectional schematic diagram of another exemplary force sensor in accordance with the present teachings.
Figure 3B:
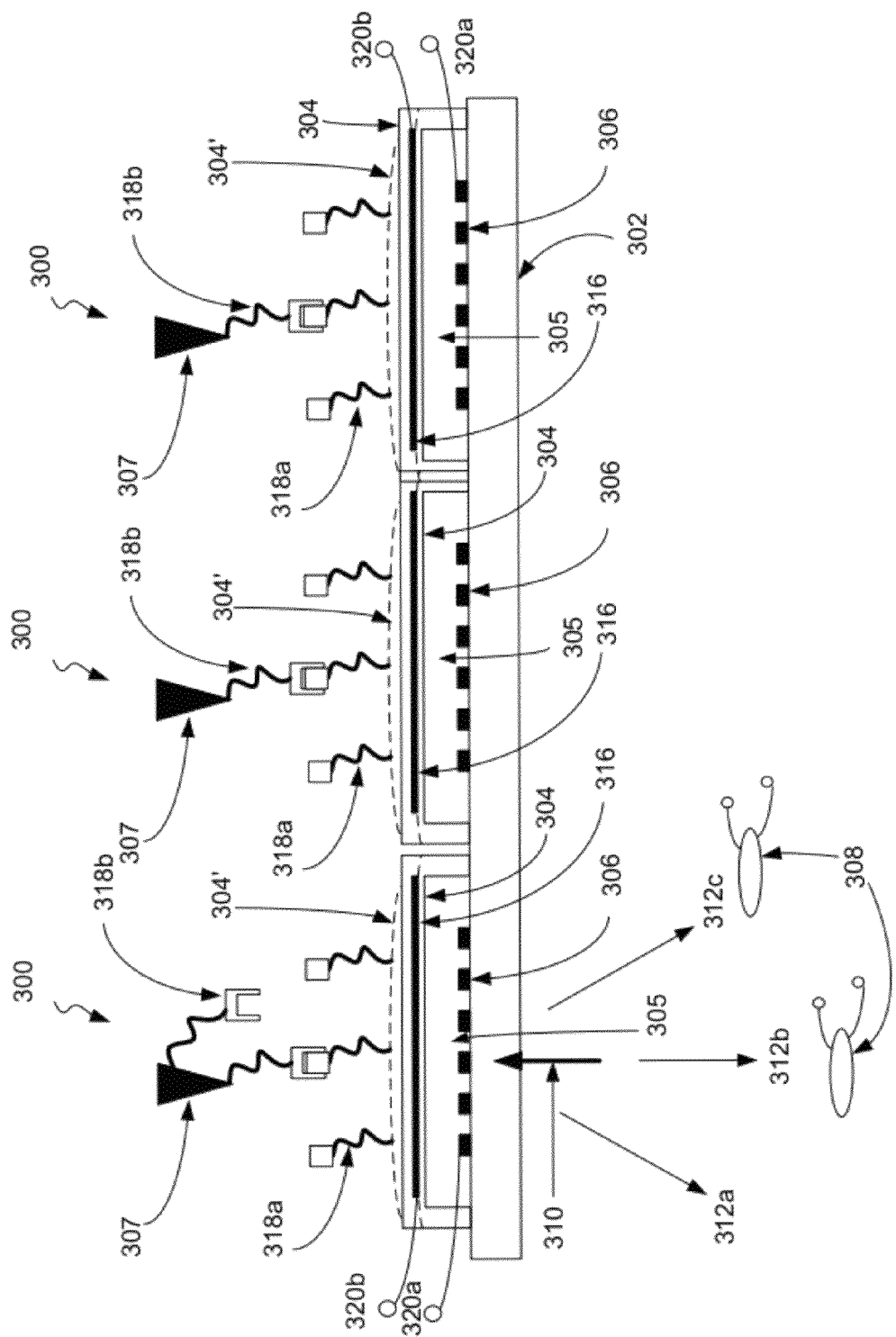
FIG. 3B shows a cross-sectional schematic diagram of another exemplary force sensor in accordance with the present teachings.

FIG. 3A depicts a schematic diagram of another exemplary force sensor 300 and FIG. 3B depicts a schematic diagram of multiple force sensors 300 working in concert in accordance with the present teachings. The embodiments shown in FIGS. 3A and 3B can be used as force sensors for parallel force measurements, such as in the case of biomolecular mechanics. The force sensors 300 shown in FIGS. 3A and 3B can comprise a detection surface 302 and a flexible mechanical structure 304. The force sensor 300 can also comprise a grating 306 and a tip 307 positioned above the flexible mechanical structure 304. According to various embodiments reactive substances, such as molecules, including biomolecules, labeled 318a and 318b in FIGS. 3A and 3B can be attached to flexible mechanical structure 304 and tip 307, respectively. In some embodiments, the force sensors 300 can also include a top electrode 316. FIG. 3B shows the force sensors 300 in contact with a single detection surface 302. However, in some cases more than one force sensor 300 can contact a separate detection surface so as to be controlled separately.

The force sensors 300 can be used to characterize various material properties of the reactive substance. For example, biomolecular bonding can be determined by moving the tip 307 contacted by a reactive substance, including, for example, inorganic molecules and/or organic molecules, such as biomolecules, over the force sensors 300. It is also contemplated that the tip 307 can remain stationary and the force sensors 300 can be moved relative to the tip 307. The reactive substance on the flexible mechanical structure 304 can be attracted to the reactive substance on the tip 307. A stimuli 319, such as a force, light, or temperature, on, for example, the force sensor 300 or the tip 307 caused by, for example the molecular attraction, a light source, or a temperature source, can cause the flexible mechanical structure 304 to bend, or flex as shown by 304'. Light 310 can also be directed through detection surface 302 to impinge on the flexible mechanical structure. The light 310 is reflected from the flexible mechanical structure and then diffracted by the grating 306. As the stimuli displaces the flexible mechanical structure, the thickness of the gap 305 changes. This can cause the reflected light to diffract differently than if the flexible mechanical structure were in its un-bent position. Thus, different diffraction order intensities can be generated as the light passes through the grating 306 depending on the gap thickness. After passing through the grating 306 the diffracted light 312a-c can be detected by the detectors 308. The output from the flexible mechanical structure 304 can be used in a feedback loop to direct an external actuator (not shown) to adjust the tip-flexible mechanical structure distance (i.e., the gap thickness), and thus the tip-sample distance (d). According to various embodiments, the flexible mechanical structure 304 can be electrostatically actuated to apply desired forces by biasing electrodes 320a and 320b attached to the grating 306 and the top electrode 316, respectively.

By using a variety of techniques disclosed herein, displacements from 1 mm down to $1 \times 10^{-6}$ Å/√Hz or lower can be measured. As such, forces from 1N down to 1 pN can be detected with 10 kHz bandwidth with an effective spring constant of the sensor flexible mechanical structure from about 0.001N/m to about 1000N/m at its softest point. These mechanical parameters can be achieved by micro-machined flexible mechanical structures, such as MEMs microphone flexible mechanical structures. Therefore, using flexible mechanical structure surfaces and tips functionalized by interacting reactive substances, as shown in FIGS. 3A and 3B, force spectroscopy measurements can be performed in parallel using optical or electrostatic readout.

For example, in the case of rupture force measurements, the reactive substance, such as a molecule, is pulled and if the bond is intact, the flexible mechanical structure is also pulled out while the displacement, i.e., applied force, is measured. With the bond rupture, the flexible mechanical structure comes back to rest position. The force sensor flexible mechanical structures can be individually actuated to apply pulling forces to individual molecules and measuring their extensions allowing for array operation.

Figure 4A:
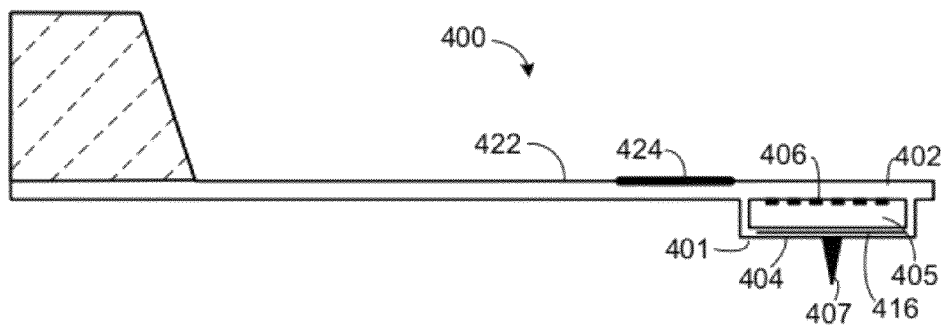
FIG. 4A shows a cross-sectional schematic diagram of another exemplary force sensor in accordance with the present teachings.
Figure 4B:
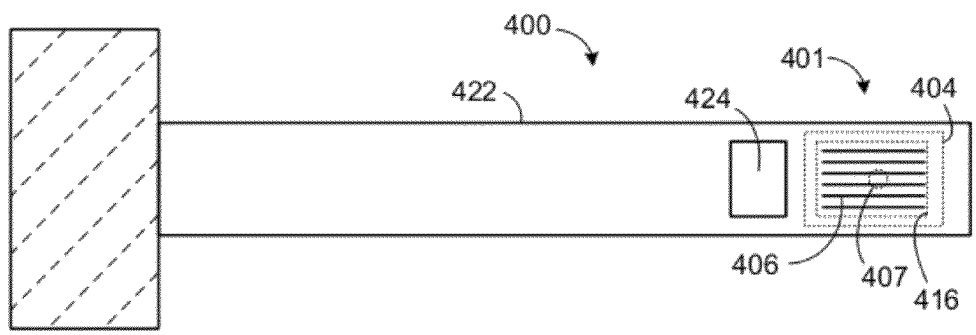
FIG. 4B shows a bottom up view perspective of another exemplary force sensor in accordance with the present teachings.
Figure 4C:
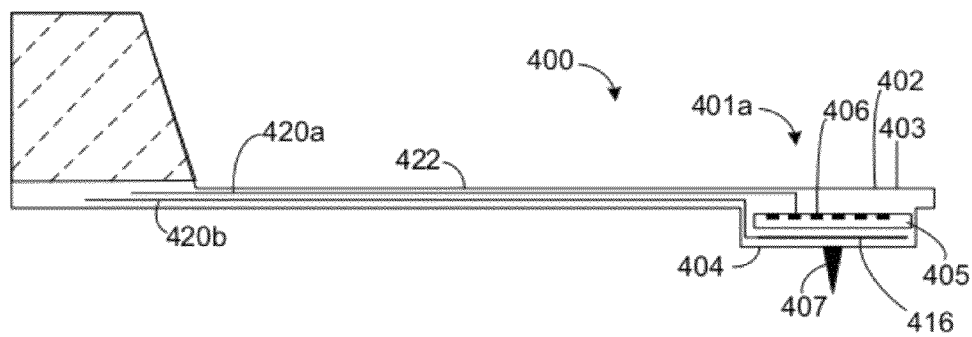
FIG. 4C shows a cross-sectional schematic diagram of an exemplary force sensor array in accordance with the present teachings.

FIGS. 4A-4C depict perspective views of exemplary embodiments in accordance with the present teachings. FIG. 4A depicts a cross-sectional schematic diagram and FIG. 4B depicts a view of the top of a force sensor structure 400. The force sensor structure 400 can include a cantilever 422, such as that used in AFM, and a force sensor 401 positioned on the free end of the cantilever 422. The force sensor 401 can comprise a detection surface 402, a flexible mechanical structure 404, a gap 405, grating 406, a tip 407, and a top electrode 416. Further, the cantilever 422 can be transparent to allow for optical readout of the deflection of the flexible mechanical structure, which has an integrated tip for imaging. The cantilever 422 can be made of materials similar to those of the detection surface material, described above. Indeed, in some embodiments, the cantilever 422 itself can comprise the detection surface 402. Alternatively, the detection surface can be a substrate formed on the cantilever. In some embodiments the cantilever 422 can also include a reflector 424.

The cantilever 422 can be used to provide periodic tapping impact force for tapping mode imaging to apply controlled forces for contact mode or molecular pulling experiments. Because the flexible mechanical structure 404 can be stiffer than the cantilever 422 and can be damped by immersion in a liquid, the measurement bandwidth can be much larger than the cantilever 422. Furthermore, optical readout of the diffraction orders can directly provide tip displacement because the diffraction orders can be generated by the grating 406 under the flexible mechanical structure 404.

According to various embodiments, the reflector 424 can be used to beam bounce to find cantilever deflection for feedback, if needed. In some cases, the tip-force sensor output can provide the real force feedback signal. The cantilever 422 and the flexible mechanical structure 404 dimensions can be adjusted for the measurement speed and force requirements.

FIG. 4C depicts a cross-sectional schematic diagram of another exemplary force sensor 401a in accordance with the present teachings. The force sensor 401a is similar to the force sensor 401 but includes a thicker base region 403 of the detection surface 402. Also shown in FIG. 4C are electrical connections 420a and 420b that contact the grating 406 and the top electrode 416, respectively. The electrical connections can be used to provide electrostatic actuation or capacitive detection.

FIG. 5A shows an embodiment of a force sensor structure 500 according to the present teaching for tapping mode imaging. In addition to topography, tapping mode can also provide material property imaging and measurement if the tip-sample interaction forces can be accurately measured. The disclosed force sensor structure solves a significant problem for this mode of operation. For example, when the cantilever is vibrated using a sinusoidal drive signal, shown in FIG. 5B, and it is brought to a certain distance to the surface, the tip starts to contact the surface during a short period of each cycle, as shown in FIG. 5C. While the oscillation amplitude is kept constant for topography information, the contact force i.e., the tip-sample interaction force and duration can be related to the material properties of the sample and adhesion forces. With a regular cantilever, the deflection signal can be dominated by the vibration modes of the signal, which can significantly attenuate the information in the harmonics. According to various embodiments, the transient force that the tip 507 or the sample 518 experiences at each tap can be measured. Because the force sensors disclosed herein can directly measure the flexible mechanical structure/tip displacement directly using optical interferometry or capacitive measurement, this transient force signal can be obtained. By designing the flexible mechanical structure stiffness, broadband response is possible and short transient force signals can be measured. This situation can be valid in both air and liquids, as the information is independent of the cantilever vibration spectrum.

Figure 6:
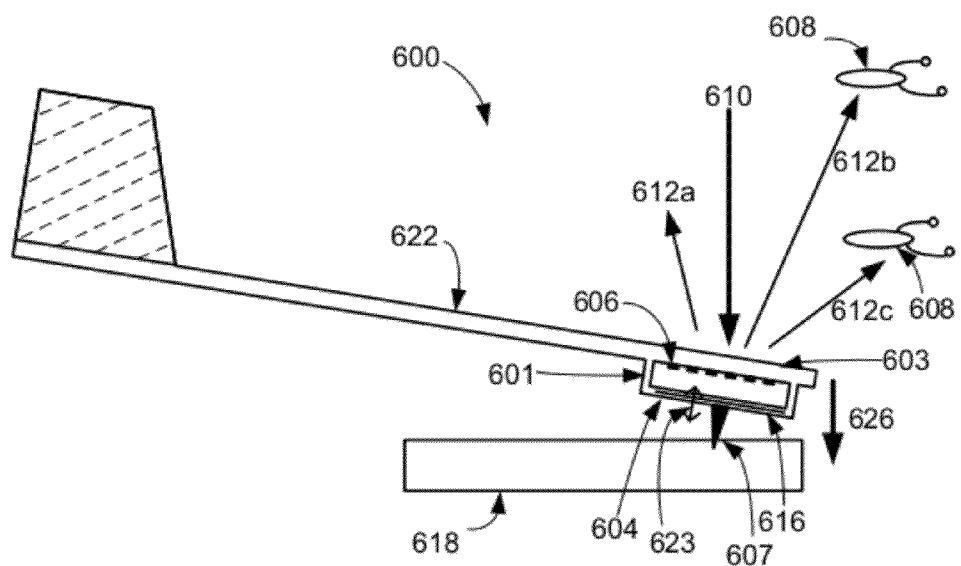
FIG. 6 shows a partial cross-sectional schematic diagram of another exemplary force sensor in accordance with the present teachings.

Using electrically isolated electrodes, the flexible mechanical structure can be actuated so as to have an "active tip". Further the actuated flexible mechanical structure can optimize the optical detection or capacitive detection sensitivity in air or in liquid environments. FIG. 6 shows an application of a force sensor structure 600 comprising a sensor 601 on a cantilever 622 where the tip 607 is active, as shown by arrow 623. In FIG. 6, the active tip 607 can be used to apply known forces to the surface of sample 618 using electrostatic actuation and optical interferometric displacement detection or capacitive displacement detection can be achieved. The tip 607 can be activated, for example, by applying a bias between the grating 606 and the top electrode 616. Further, a DC force, shown by arrow 626, can be used to keep the tip 607 in constant contact with the sample.

Light 610 can be directed to the flexible mechanical structure 604 and the orders 612a-c of light diffracted by the grating 606 can be detected by the detector 608. Similar to the force sensor 401a shown in FIG. 4C, designing the dimensions of the flexible mechanical structure base 603, or choosing the operation frequency at an anti-resonance of the cantilever, the flexible mechanical structure 604 can be moved, and hence the tip 607 can be pushed into the sample 618 by known electrostatic forces. Accordingly, displacements of the flexible mechanical structure 604 can be measured optically or capacitively. Furthermore, in some embodiments there is no need for an active tip on the force sensor. Moreover for optical measurements, the gap between the flexible mechanical structure and the grating can be optimized during fabrication of the force sensor. Thus, there is no need to actively adjust that gap during tapping mode operation as shown in FIG. 6. Similarly for capacitive detection, an electrical connection for detection of capacitance changes can be provided. In that case, the force sensor 601 can be connected to a detection circuit such as used in a capacitive microphone for measuring the force on the tip 607.

The thickness of the base 603 (or the substrate) supporting the flexible mechanical structure 604 can be adjusted to control the operation frequency to insure that the motion of the flexible mechanical structure 604 produces an indentation in the sample surface. This measurement, therefore, provides surface elasticity information directly. According to various embodiments, the frequency of electrostatic actuation can be in the ultrasonic range. Alternatively, a wideband impulse force can be applied and resulting displacements can be detected in the bandwidth of the flexible mechanical structure displacement force sensor. For these applications, it may be desirable to move the higher cantilever vibration mode frequencies away from the first resonance. This can be achieved, for example, by increasing the mass close to the tip of the cantilever, such as by adjusting the thickness, or mass of the base 603. With added mass, the cantilever acts more like a single mode mass spring system and can generate tapping signals without spurious vibrations and can also be effective at a broad range of frequencies.

Figure 7:
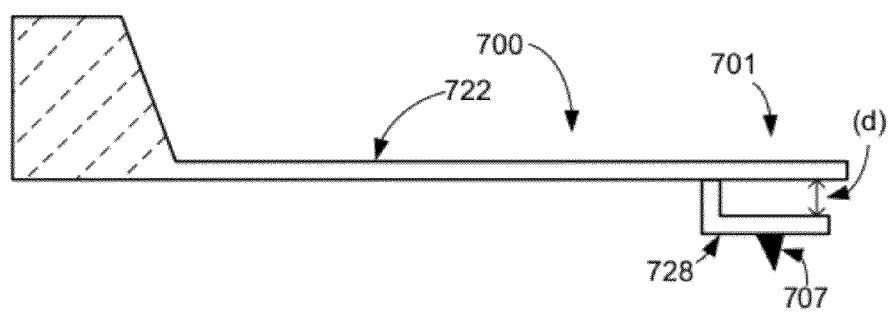
FIG. 7 shows a partial cross-sectional schematic diagram of another exemplary force sensor in accordance with the present teachings.

In general, for tapping mode AFM and UAFM applications a broadband, stiff tip displacement measurement sensor/structure can be integrated into compliant structures, such as regular AFM cantilevers. Although flexible mechanical structures are primarily described here, according to another embodiment, the tip displacement measurement structure can be a stiff beam structure with the same cross-section of the flexible mechanical structure or another stiff cantilever, as shown, for example, in FIG. 7. In FIG. 7, there is a force sensor structure 700, comprising a force sensor 701, a compliant structure 722, a tip 707, and a flexible mechanical structure 728 such as a stiff broadband structure. In this case, the stiff broadband structure 728 can be a small cantilever mounted to an end of the compliant structure 722, also a cantilever. The small cantilever 728 can be spaced a distance (d) from the compliant structure 722. The compliant structure 722 can be used to control the impact and/or contact force of the tip 707 mounted to a side of the stiff broadband structure 728. Further, the stiff broadband structure 728 can be used to measure tip displacements. Displacement of the tip 707 can be measured, for example, optically, electrostatically, capacitively, piezoelectrically or piezoresistively.

According to various embodiments, for fast imaging and tapping mode applications, the cantilever can be eliminated. In this case, a fast x-y scan of a sample or the integrated tip can be used with the described sensor/actuator for tapping and detecting forces. The large, fast z-axis motion can be generated, for example, by a piezoelectric actuator that moves the base of the force sensor, which can be a thick, rigid substrate.

Figure 8A:
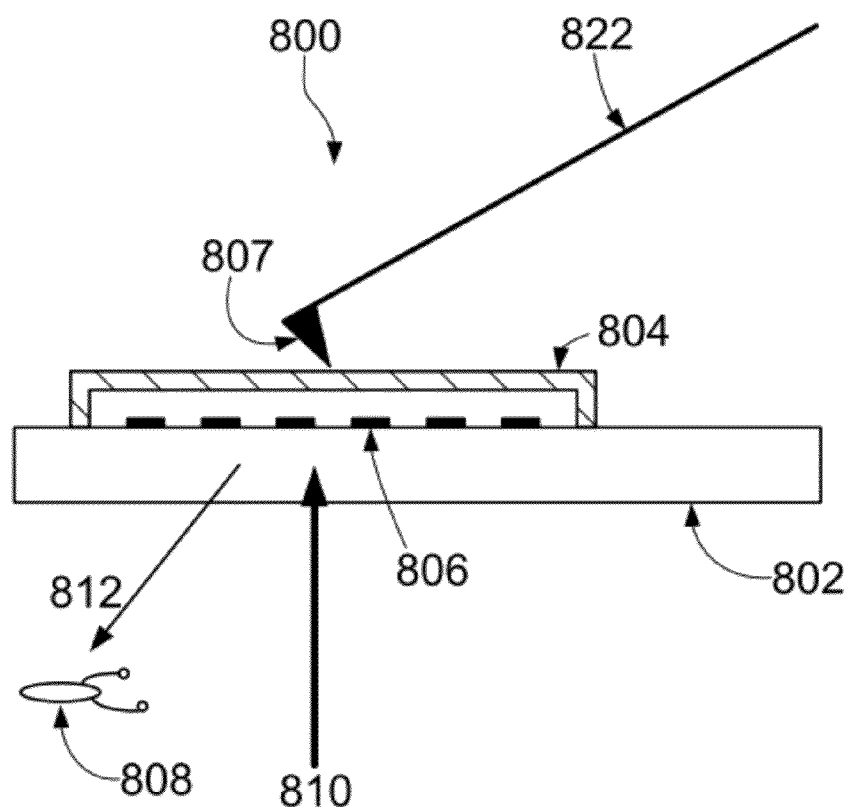
FIG. 8A shows a cross-sectional schematic diagram of an arrangement used to monitor sensitivity of an exemplary force sensor in accordance with the present teachings.

The sensitivity of a force sensor in accordance with the present teachings can be described by the following exemplary embodiment, depicted in FIG. 8A. In FIG. 8A, a rectangular silicon AFM cantilever 822 with a tip 807 is vibrated at 57 kHz above a 150 µm diameter, ~1 µm thick aluminum flexible mechanical structure 804 with an integrated diffraction grating 806. The force sensor 800 flexible mechanical structure 804 is built on a quartz detection surface or substrate 802. A DC bias of 37V is applied to move the flexible mechanical structure 804 to a position of optimal detection sensitivity and the vibrating tip 807 is brought close enough to have tapping mode-like operation with intermittent contact. Diffraction order 812 can be detected by detector 808 when a beam 810 is diffracted by grating 806 upon exiting force sensor 800.

The single shot signals collected at this position are shown at the top two rows (Row 1 and Row 2) of the four rows of the graph in FIG. 8B. The bottom graph, in FIG. 8C, shows a zoomed in version of Row 2 of individual taps, where the transient displacement of the flexible mechanical structure due to impact of the tip is clearly seen. If the flexible mechanical structure material were softer or there were a compliant coating on the flexible mechanical structure 804, the measured tap signals would be longer in duration and smaller in amplitude because the tip 807 would spend more time indenting the softer surface while transmitting less force to the flexible mechanical structure 804. Therefore, the tapping force measurement provides elasticity information and this embodiment can be used as a material property sensor for a thin film coating on the flexible mechanical structure.

In addition, when the tip 807 leaves contact, the flexible mechanical structure 804 is pulled away due to adhesion or capillary forces, permitting force spectroscopy measurement methods. When the tip 807 is moved progressively closer, it is in contact with the flexible mechanical structure 804 for a longer duration of each cycle and finally it pushes the flexible mechanical structure 804 down during the whole cycle. Thus, the simple force sensing structures disclosed herein provide information not available by conventional AFM methods and result in more effective tools for force spectroscopy applications.

Figure 9A:
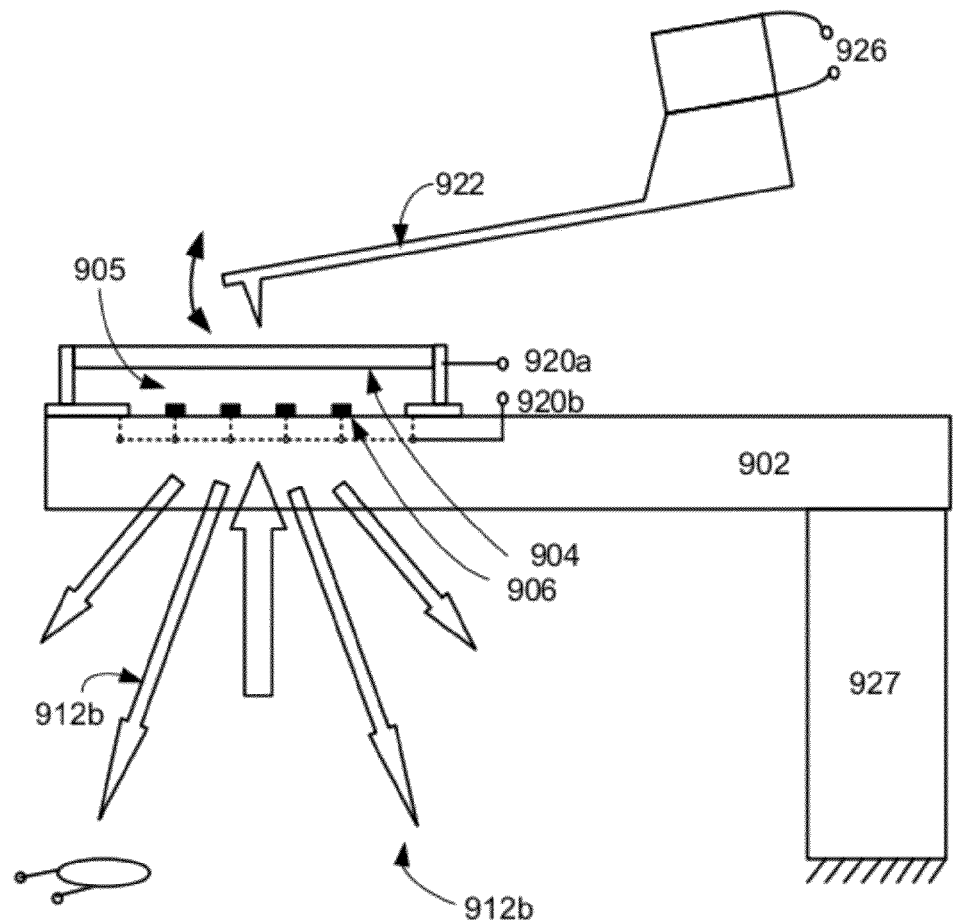
FIG. 9A shows a schematic diagram of another exemplary force sensor in accordance with the present teachings.

The sensitivity of another force sensor in accordance with the present teaching can be described by the following exemplary embodiment, depicted in FIGS. 9A-9H. As shown in FIG. 9A, a quartz substrate 902 with a sensor flexible mechanical structure 904 is placed on a piezoelectric stack transducer 927, which can be used to approach to the tip 907 and obtain force distance curves. The flexible mechanical structure 904 is aluminum and can be 150 μm in diameter, 1 μm thick, and located over a 2 μm gap 905 above the rigid diffraction grating electrode 906. In this case, the grating period is 4 μm. The gap 905 is open to air through several sacrificial layer etch holes (not shown). The grating 906 can be illuminated through the quartz substrate 902 using, for example, a HeNe laser ($\lambda$=632 nm) at a 5° angle away from normal to the substrate. The output optical signal can be obtained by recording the intensity of the 1st diffraction order beam 912b.

For measuring the AFM dynamic tip-sample interaction forces, the cantilever 922 can be glued on a piezoelectric AC drive transducer 926 that can drive the cantilever 922 at its resonant frequency. The flexible mechanical structure 904, with a stiffness of approximately 76N/m as measured at the center using a calibrated AFM cantilever 922, can be used. The DC bias on the flexible mechanical structure 904 is adjusted to 27V to optimize the optical detection, and the sensitivity is calibrated as 16 mV/nm by contacting the flexible mechanical structure 904 with a calibrated AFM cantilever 922 and a calibrated piezo driver. In this case, the broadband RMS noise level of the system was about 3 mV (0.18 nm) without much effort to reduce mechanical, laser, or electrical noise.

A force curve can be produced by moving the piezoelectric stack 927 supporting the substrate 902 with a 20 Hz, 850 nm triangular signal and making sure that there is tip-flexible mechanical structure contact during a portion of the signal period. The cantilever 922 can be, for example, a FESP from Veeco Metrology, Santa Barbara, Calif., with k=2.8N/m.

Figure 9B:
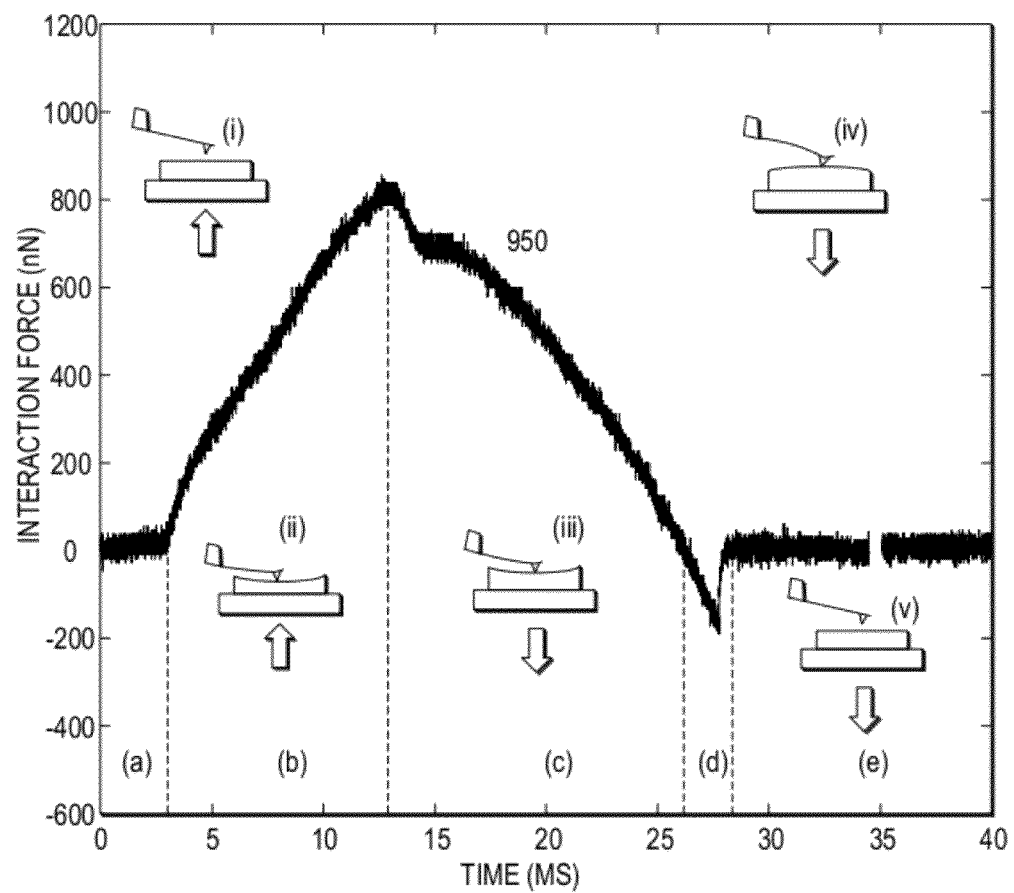
FIG. 9B shows a graph of interaction force versus time for an exemplary force sensor in accordance with the present teachings.

FIG. 9B shows a force curve 950 where the inset drawings (i)-(v) indicate the shape of the cantilever 922 and flexible mechanical structure 904, and the hollow arrow indicates the direction of motion of the piezo stack 927 and the quartz substrate 902. Moreover, the insert drawings (i)-(v) correspond to sections (a)-(e), respectively, of the curve 950. Before measurement, the flexible mechanical structure 904 is at rest, as seen in insert (i) and section (a). Tip-flexible mechanical structure contact happens starting in section (b) at around 3 ms and the tip bends the flexible mechanical structure 904 downwards, as shown in insert drawings (ii) and (iii). Tip-flexible mechanical structure contact continues through section (c) until about 26 ms, which is in section (d). The piezoelectric motion is reversed starting at section (c). Section (d) shows that attractive forces due to adhesion pulls the flexible mechanical structure 904 up, as seen in insert (iv), for 2 ms and then the flexible mechanical structure 904 moves back to its rest position, as seen in insert (v) after a 180 nN jump at the end of the retract section. Curve 950 in section (e) shows the rest position.

Figure 9C:
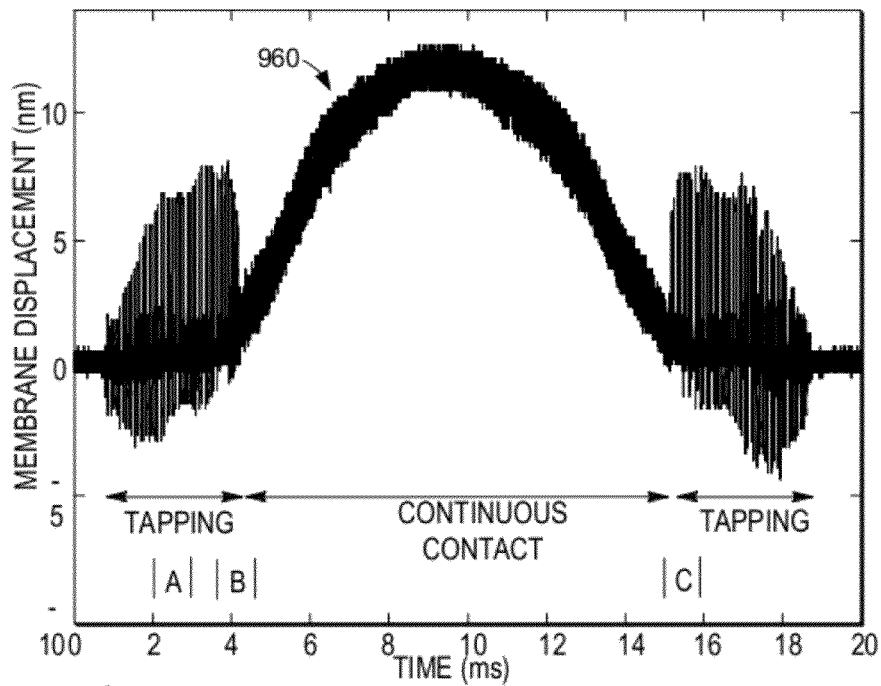
FIGS. 9C-9F show graphs of a flexible mechanical structure displacement versus time for an exemplary force sensor in accordance with the present teachings.

For direct observation of time resolved dynamic interaction forces along the force curve, a similar experiment can be performed while the cantilever 922 is driven into oscillation by applying a sinusoidal signal to the AC drive piezo 926 at 67.3 kHz. The single shot, transient flexible mechanical structure displacement signal 960 obtained during a cycle of the Hz drive signal is shown in FIG. 9C. Dynamic interaction force measurements provide various types of information, as indicated by the various interaction regimes (A)-(C) during the measurement. The data of FIG. 9C is shown expanded in FIGS. 9D-F in the initial tapping region (A), intermittent to continuous contact region (B), and continuous to intermittent contact transition region (C), respectively.

Figure 9D:
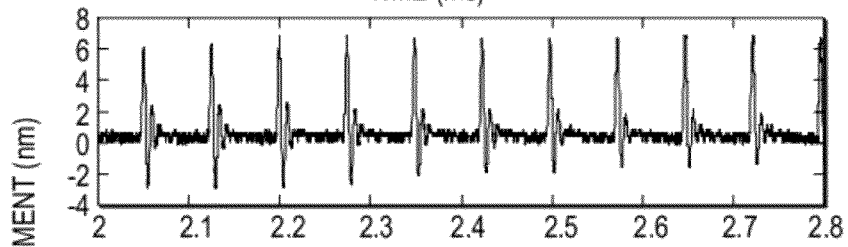
Figure 9E:
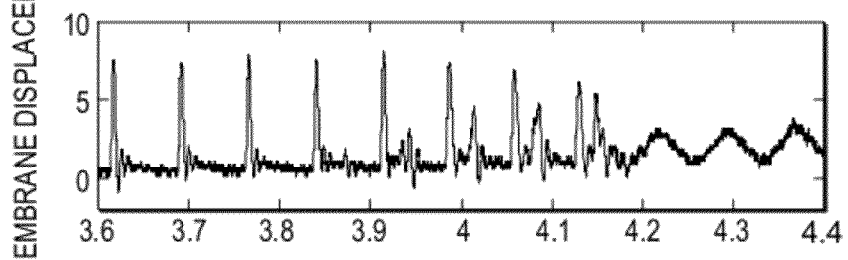
Figure 9F:
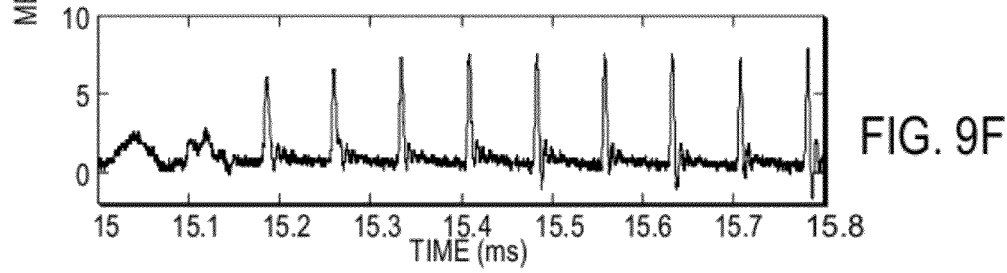

Starting from the left, the cantilever tip 907 is first out of contact with the flexible mechanical structure 904. At around 1 ms it starts intermittent contact (tapping) with the flexible mechanical structure 904 as individual taps are detected, as shown in FIG. 9D. As the cantilever 922 gets closer to the flexible mechanical structure 904, the pulses become unipolar and the distortion is more severe as there are double peaked tap signals when the cantilever 922 gets into contact due to non-linear interaction forces, as shown FIG. 9E. When the tip 907 is in continuous contact, which happens around 4.2 ms, the displacement signal has the periodicity of the drive signal in addition to distortion that can be caused by contact non-linearities and higher order vibration modes of the cantilever 922 with its tip 907 hinged on the flexible mechanical structure 904. Similarly, around 15 ms, the cantilever 922 starts breaking off the flexible mechanical structure surface and tapping resumes, as shown in FIG. 9F. Between 7 ms and 12 ms the curve is not linear.

Individual tapping signals can be filtered by the dynamic response of the flexible mechanical structure 904. In this example, the force sensor was not optimized and the flexible mechanical structure 904 acted as a lightly damped resonator with a resonant frequency at 620 kHz rather than having broadband frequency response that is ideal for fast interaction force measurements. Nevertheless, the transfer function of the flexible mechanical structure 904 can be obtained using, for example, integrated electrostatic actuators, as described herein.

Figure 9G:
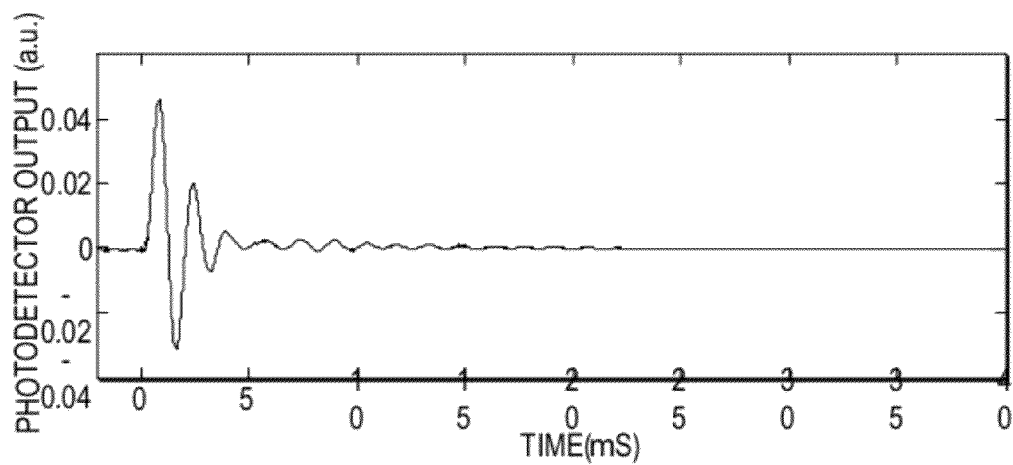
FIGS. 9G-9H show graphs of photo-detector output versus time for an exemplary force sensor in accordance with the present teachings.
Figure 9H:
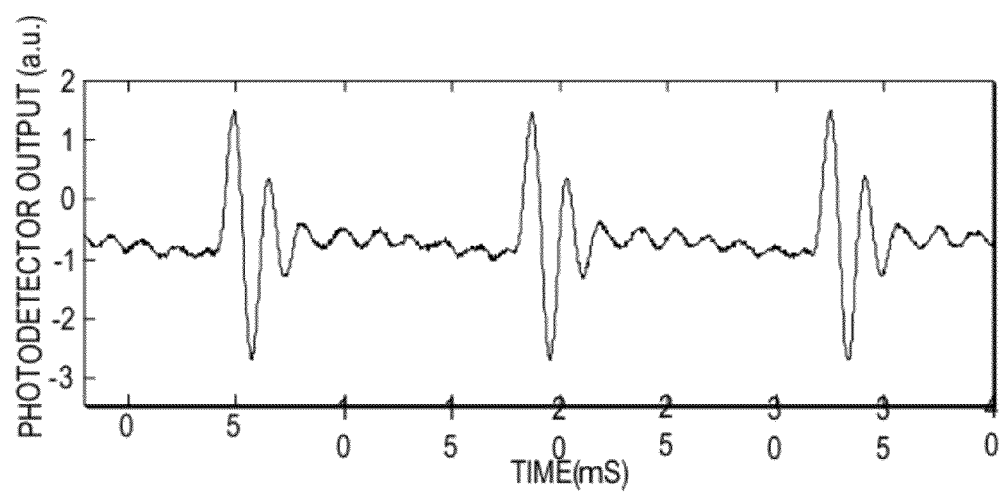

Still further, FIG. 9G shows the measured temporal response of the flexible mechanical structure 904 when a 2V square pulse 100 ns in length is applied in addition to the 27V DC bias at the actuator terminals. Comparing the trace waveform in FIG. 9G with averaged data from individual tap signals shown in FIG. 9H, it can be seen that the stiff cantilever tap is nearly an impulsive force, which can be recovered by inverse filtering.

Thus, according to various embodiments, minimum displacement detection levels down to $10\text{-}4 \text{ Å}/\sqrt{Hz}$ can be measured and mechanical structures with spring constants in the 0.001 to 10N/m range can be built that can monitor force levels in the pico-Newton range. These sensitivity levels can make it useful for a wide range of probe microscopy applications including quantitative interaction force measurements, fast imaging in liquids and in air, and probe arrays for imaging, lithography, and single molecule force spectroscopy.

While FIGS. 8A-9H are examples of sensitivity testing made by applying a force from a tip to the force sensor, similar sensitivities can be achieved when a tip is mounted to the force sensor and the force sensor is used to characterize a sample.

Figure 10A:
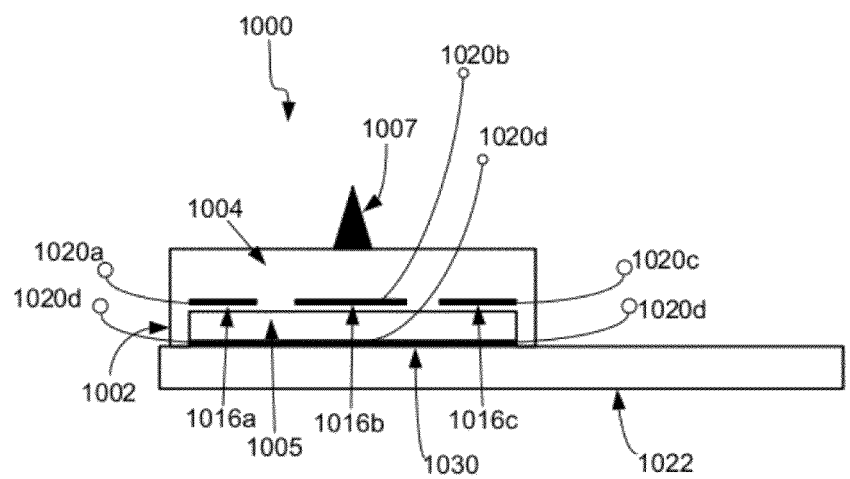
FIG. 10A shows a cross-sectional schematic diagram of another exemplary force sensor in accordance with the present teachings.
Figure 10B:
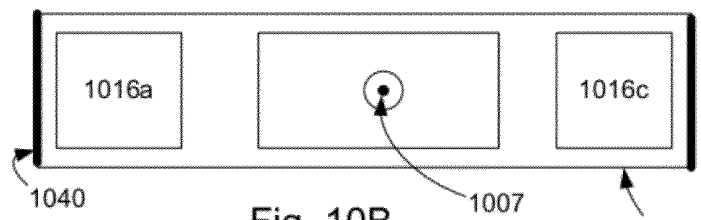
FIG. 10B shows a cross-sectional schematic diagram of another exemplary force sensor in accordance with the present teachings.
Figure 10C:
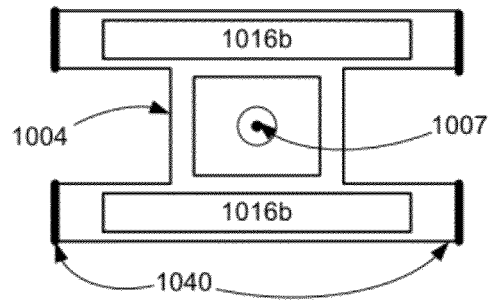
FIG. 10C shows a cross-sectional schematic diagram of another exemplary force sensor in accordance with the present teachings.
Figure 10D:
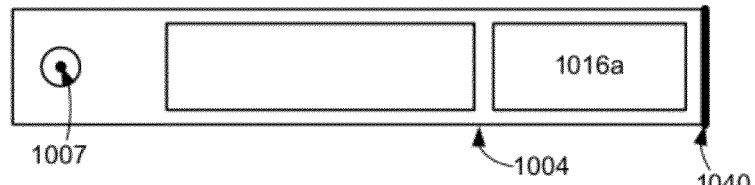
FIG. 10D shows a cross-sectional schematic diagram of another exemplary force sensor in accordance with the present teachings.

FIG. 10A depicts a cross-sectional schematic diagram of another exemplary force sensor 1000 in accordance with the present teachings. The sensor 1000 can comprise a substrate 1002, a flexible mechanical structure 1004, a gap 1005, a tip 1007, a plurality of separate top electrodes, such as electrodes 1016a-c, and a bottom electrode 1030. The force sensor 1000 substrate 1002 can be positioned at an end of a cantilever 1022. According to various embodiments, the flexible mechanical structure 1004 can be fully clamped around its circumference as described above and shown in FIG. 10A. Alternatively, the flexible mechanical structure 1004 can be a clamped-clamped beam with a rectangular or H-shape, as shown in FIGS. 10B and 10C, respectively, where the short edges 1040 at the ends are clamped. Still further, the flexible mechanical structure 1004 can be a cantilever structure or a similar structure that changes shape in a predictable manner in response to a force applied to the tip 1007, as shown in FIG. 10D.

Each of the plurality of separate top electrodes 1016a-c can be electrically isolated and formed in the flexible mechanical structure 1004. Moreover, the bottom electrode 1030 can spaced apart from the separate top electrodes 1016*a-c* by the gap 1005. Further, the bottom electrode can be positioned in the substrate 1002 and can be contacted by electrode terminals 1020*d*. Similarly, each of the separate top electrodes 1016*a-c* can be contacted by electrode terminals 1020*a-c*. In some cases, the electrode terminals 1020*a-c* and 1020*d* can be capacitive sensing terminals that can detect a capacitance change formed between the separate top electrodes 1016*a-c* and the bottom electrode 1030.

In FIG. 10A, a voltage can be applied between the electrode terminals 1020*a-c* and 1020*d*. The voltage can be used to independently control and move any of the separate top electrodes 1016*a-c*, so that they can serve as actuators. Further, the separate top electrodes 1016*a-c* can also perform sensing, similar to that of a dual electrode capacitive micromachined ultrasonic transducer where the vibrations of the sensor flexible mechanical structure are converted to electrical current signals through change in capacitance.

For example, the force sensor 1000 can be used for fast imaging where bias voltages are applied between the electrode terminals 1020*a*, 1020 *c* and the bottom electrode terminal 1020*d* and alternating voltages of the same or reverse phase are applied to the electrode terminals 1020 *a* and 1020 *c* to vibrate the tip 1007 vertically or laterally to have intermittent contact with a sample surface. In some cases, the forces between the tip 1007 and a close by surface can be sensed without contact for non-contact imaging. The bias voltages applied to the electrode terminals 1020*a*, 1020*c* also control the position of the tip 1007 in response to changes in capacitance detected between the electrode terminals 1020*b* and the bottom electrode terminal 1020*d*. An external controller (not shown) can read the detected capacitance change and generate the control signals (bias voltages) applied to the electrode terminals 1020*a*, 1020*c* and the bottom electrode terminal 1020*d*.

Figure 11A:
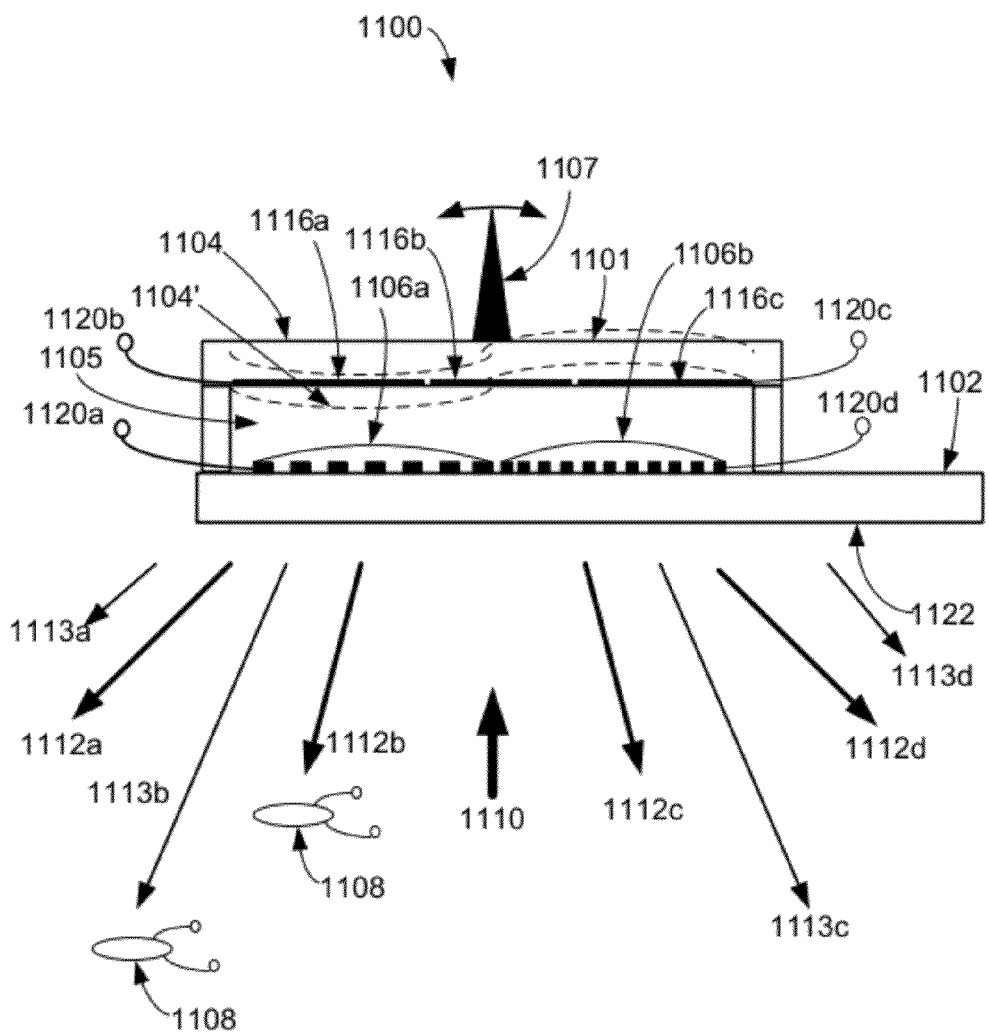
FIG. 11A shows a schematic diagram of another exemplary force sensor in accordance with the present teachings.

FIG. 11A depicts a cross-sectional schematic diagram of another exemplary force sensor unit 1100 in accordance with the present teachings. The force sensor unit 1100 can comprise a force sensor 1101, a detection surface 1102, a flexible mechanical structure 1104, a gap 1105, a tip 1107, a plurality of separate top electrodes, such as electrodes 1116*a-c*, a plurality of gratings, such as first grating 1106*a* and second grating 1106*b*, at least one detector 1108, and a cantilever 1122. The first grating 1106*a* can have a different grating spacing than the grating spacing of 1106*b*. Furthermore, the first grating 1106*a* can have a different orientation as compared to the grating 1106*b*. It is to be understood that other force sensor embodiments described herein can also comprise multiple gratings.

The detection surface 1102 can be positioned at a free end of the cantilever 1122. Moreover, the flexible mechanical structure 1104 can be fully clamped around its circumference, it can be a clamped-clamped beam with a rectangular or H shape where the short edges at the ends are clamped, or it can be a cantilever structure or a similar structure that changes shape in a predictable manner in response to a force applied to the tip 1007.

The force sensor 1101 shown in FIG. 11A can be used for lateral force or friction measurements. For example, force sensor 1101 can be used to sense torsion created on the flexible mechanical structure, shown as 1104'. Separate top electrodes 1116*a-c* can be positioned on the flexible mechanical structure 1104 to excite the torsional motion or resonances. Similarly, the flexible mechanical structure 1104 can be bent asymmetrically, shown as 1104', due to torsion created by the tip 1107 or due to out of phase actuation from the first grating 1106*a*, the second grating 1106*b*, and the top electrodes 1116*a-c* acting as electrostatic actuators. In particular, a voltage can be applied to the electrical contacts 1120*a* and 1120*b* that contact the first grating 1106*a* and the top electrode 1116*a*, respectively. The same voltage can be applied to the electrical contacts 1120*c* and 1120*d* that contact the second grating 1106*b* and the a top electrode 1116*c*, respectively. Applying this same voltage can cause the flexible mechanical structure 1104 to bend up and down. In contrast, similarly applying a differential voltage can cause torsion of the flexible mechanical structure 1104.

A light beam 1110 can be directed through the detection surface 1102 to impinge on the flexible mechanical structure 1104. The beam 1110 reflects off of the flexible mechanical structure 1104, a portion of which can be reflective, and is diffracted differently by the first grating 1106*a* and the second grating 1106*b*. As shown in FIG. 11A, the first grating 1106*a* can generate a first set of diffraction orders 1112*a-d* and the second grating 1106*b* can generate a second set of diffraction orders 1113*a-d*. The detectors 1108 can detect the different diffraction orders. The detector outputs can be added to obtain up and down bending displacement detection. Similarly, the outputs can be subtracted to obtain torsional motion and force detection. This information can be obtained when the spring constant for the second bending mode (torsion around the mid axis) of the flexible mechanical structure 1104, clamped-clamped beam or a cantilever is known. Thus, in addition to acting as actuators, the first grating 1106*a* and second grating 1106*b* can be used to optically or capacitively decouple the bending motion from the torsional motion. As such, the sensed outputs of these detectors yield both bending and torsional motion information. One can also use separate beams 1110 to illuminate the plurality of gratings.

Figure 11B:
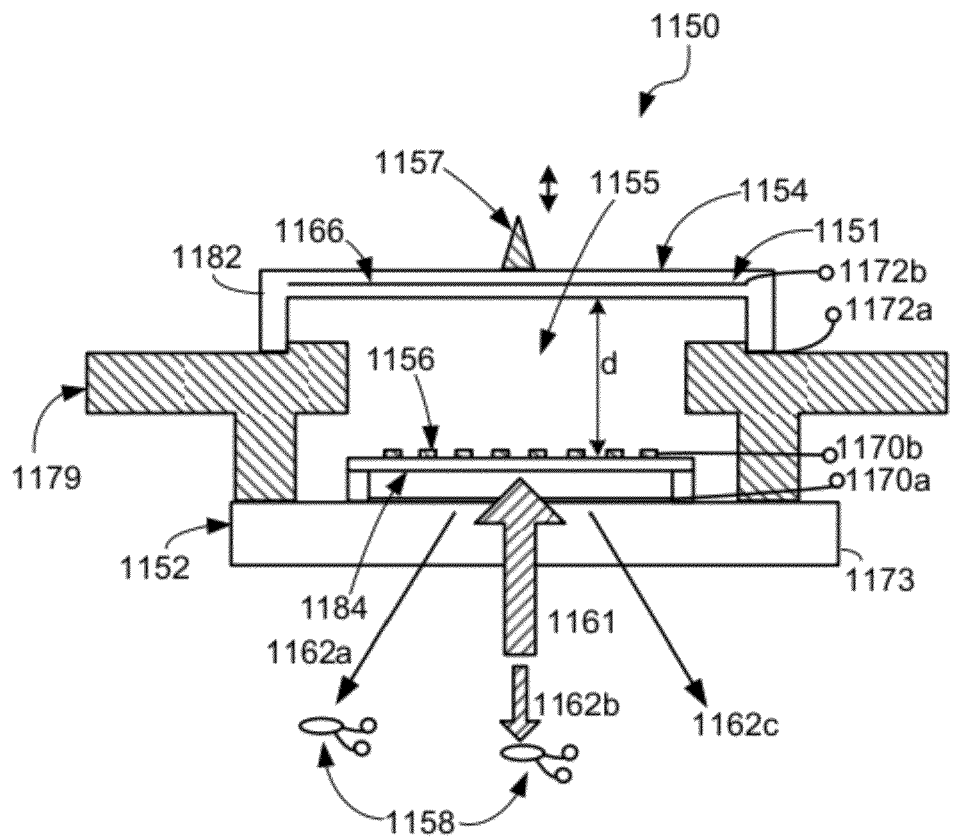
FIG. 11B shows a schematic diagram of another exemplary force sensor in accordance with the present teachings.

FIG. 11B depicts a cross-sectional schematic diagram of another exemplary force sensor unit 1150 in accordance with the present teachings. The force sensor unit 1150 can comprise a force sensor 1151, a first detection surface 1152 such as a substrate, a flexible mechanical structure 1154, a gap 1155, a tip 1157, a top electrode 1166, a grating 1156, grating flexible mechanical structure actuation inputs 1170*a* and 1170*b*, and tip flexible mechanical structure actuation inputs 1172*a* and 1172*b*. The force sensor 1151 can be affixed to a free end of a cantilever (not shown). The grating flexible mechanical structure actuation input 1170*a* can contact a transparent conductor 1173, such as indium tin oxide, formed on the first detection surface 1152. According to various embodiments, the flexible mechanical structure 1154 can be separated from the grating by a distance (d). Moreover, the flexible mechanical structure 1154 can comprise the top electrode 1166 and the grating 1156 can be spaced away from the first detection surface 1152.

The force sensor 1151 shown in FIG. 11B can extend the tip actuation range without degradation in optical displacement measurement sensitivity. For example, the tip 1157 can be positioned at a relatively large distance away from the grating 1156. In this manner, the tip 1157 can be moved large distances without shorting or damaging the sensor 1150. Moreover, the grating 1156 can be actuated to keep the detection sensitivity at an optimal level. For example, the gating can be actuated a distance of $\lambda/4$, where $\lambda$ is the wavelength of light 1161, to provide proper sensitivity.

The tip 1157 and flexible mechanical structure 1154 can be spaced away from the grating in various ways. For example, rigid supports 1179 can be formed on the first detection surface 1152 to support the first detection surface 1154. In this manner, the flexible mechanical structure 1154 is separated from the grating 1156 at a predetermined distance. A second detection surface 1184 can be separated from the first detection surface 1152 by a gap so as to provide a predetermined separation distance. The grating 1156 can be formed on the second detection surface 1184.

Operation of the sensor 1150 is similar to that described above. For example, light 1161 is directed through the first detection surface 1152, which can be transparent. The light 1161 passes through the transparent conductor 1173 and through the grating 1156 and impinges the flexible mechanical structure 1154. The light is reflected from the flexible mechanical structure 1154 and is diffracted by grating 1156 before being detected by detectors 1158.

Figure 11C:
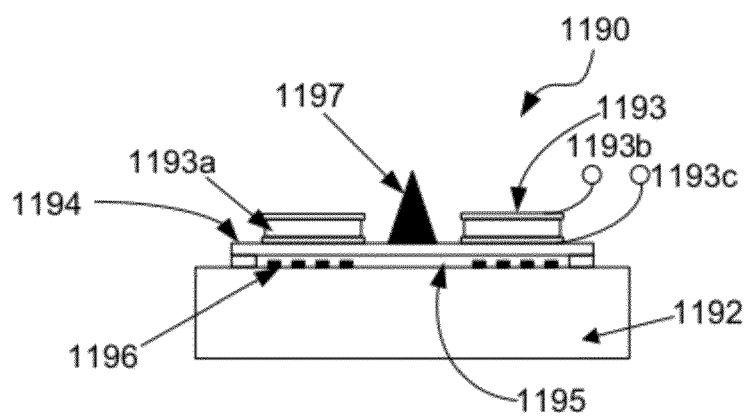
FIG. 11C shows a schematic diagram of another exemplary force sensor in accordance with the present teachings.

FIG. 11C depicts a cross-sectional schematic diagram of another exemplary force sensor 1190 in accordance with the present teachings. The force sensor 1190 can comprise a detection surface 1192, a piezoelectric actuator 1193 comprising a thin piezoelectric film 1193a disposed between a pair of electrodes 1193b and 1193c, a flexible mechanical structure 1194, a gap 1195, a tip 1197, and a grating 1196. The force sensor 1190 can be combined with at least one detector and a cantilever to form a force sensor unit.

According to various embodiments, the thin piezoelectric film can comprise a piezoelectric material such as, for example, ZnO or AlN. The piezoelectric film can be deposited and patterned on the flexible mechanical structure 1194 along with the tip 1197. The piezoelectric actuator 1193 can form, for example, a bimorph structure that can be bent and vibrated by applying DC and AC signals through the electrodes 1193b and 1193c. According to various embodiments, the grating 1196 can be placed off-center so as to provide a large range of tip motion that can be detected without losing sensitivity.

Figure 12:
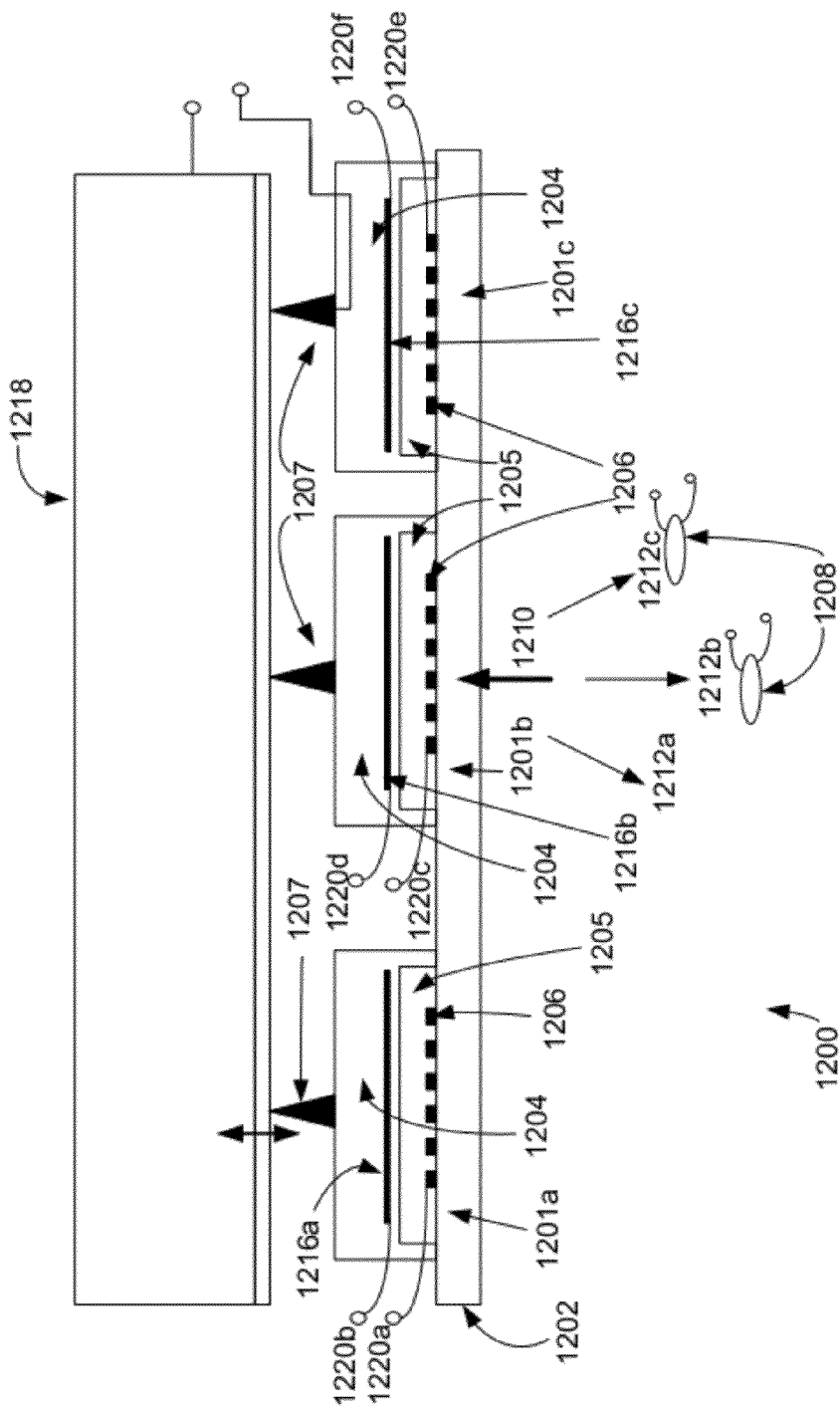
FIG. 12 shows a schematic diagram of another exemplary force sensor in accordance with the present teachings.

FIG. 12 depicts a cross-sectional schematic diagram of an array 1200 of force sensors 1201a-c in accordance with the present teachings. The array 1200 can comprise multiple force sensors, such as force sensors 1201a-c, formed on a detection surface 1102. Each of the force sensors 1201a-c can comprise a flexible mechanical structure 1204, a gap 1205, a tip 1207, an electrode, such as electrodes 1216a-c, and a grating 1206. According to various embodiments, the array 1200 of force sensors can be used for imaging and sensing at the same time so as to enable simultaneous sensing of a physical, chemical, or biological activity and imaging of the sample 1218 surface. The force sensors 1201a-c can be combined with at least one detector 1208 and a cantilever (not shown) to form a force sensor unit. Some of the force sensors 1201a-c can be modified to include, for example, electrodes, sensitive films, or optical waveguides, while the others can be used for regular probe microscopy imaging of topography. Thus, each force sensor can perform the same of different function.

For example, force sensor 1201a can be used to measure and image the elasticity or adhesion of the surface of sample 1218. Further, the grating 1206 can be used with electrode 1216a to provide actuation of the flexible mechanical structure 1204 by applying a voltage between contacts 1220a and 1220b, respectively. The elasticity information can be measured by applying known dynamic and quasi-static forces to the surface with the tip 1207 using an external actuator or by applying voltage to the terminals 1220a and 1220b. At the same time, the diffraction order intensities can be monitored by the optical detectors 1208 or a capacitance change can be detected by electrical means to determine the resulting tip displacement. visco-elasticity or adhesion can be calculated using computer models well known by those who are skilled in the art of probe microscopy.

Force sensor 1201b can be used to measure and image the topography of the surface of sample 1218 similarly as described herein using beam 1210 to generate diffraction orders 1212a-c that can be detected by detectors 1208. In the case of force sensor 1201b, the grating 1206 can be used with electrode 1216b to provide actuation of the flexible mechanical structure 1204 by applying a voltage between contacts 1220c and 1220d, respectively.

Still further, the force sensor 1201c can be used to measure and image the surface potential of sample 1218. In the case of force sensor 1201c, the grating 1206 can be used with electrode 1216c to provide actuation of the flexible mechanical structure 1204 by applying a voltage between contacts 1220e and 1220f, respectively. Moreover, the sample 1218 can be biased with respect to the tip 1207 of the force sensor 1201c using the electrical terminal 1220g to assist in surface potential measurements. The tip 1207 on the force sensor 1216c can have a separate electrical terminal 1220h which is electrically isolated from the other electrodes 1220f and 1220e and placed in the dielectric sensor flexible mechanical structure 1204. The surface potential can then be measured using a electric potential measurement device connected between terminals 1220g and 1220h. Furthermore, an external source can be connected to terminals 1220g and 1220h and the current flow in that electrical circuit can be measured to determine locally the flow of ions or electrons available from the sample 1218 or in a solution that the force sensor 1216c is immersed.

As described previously, the fore sensors 1216a and 1216b can be used to obtain surface topography and elasticity information. This information can be used by an external controller to adjust the position of the tips 1207 of individual force sensors to optimize the measurements. As such, the array 1200 can be used to measure elasticity, electrochemical potential, optical reflectivity, and fluorescence while also imaging the surface.

Figure 13A:
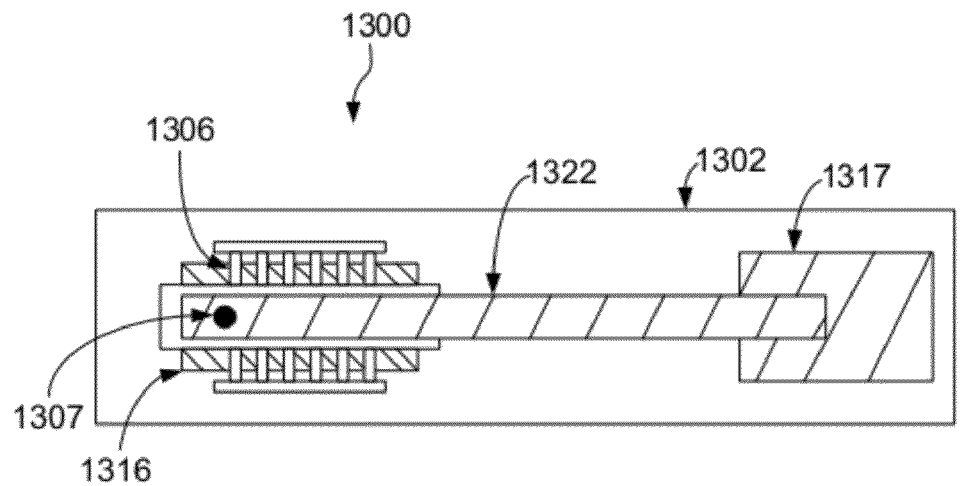
FIG. 13A shows a schematic diagram of another exemplary force sensor in accordance with the present teachings.
Figure 13B:
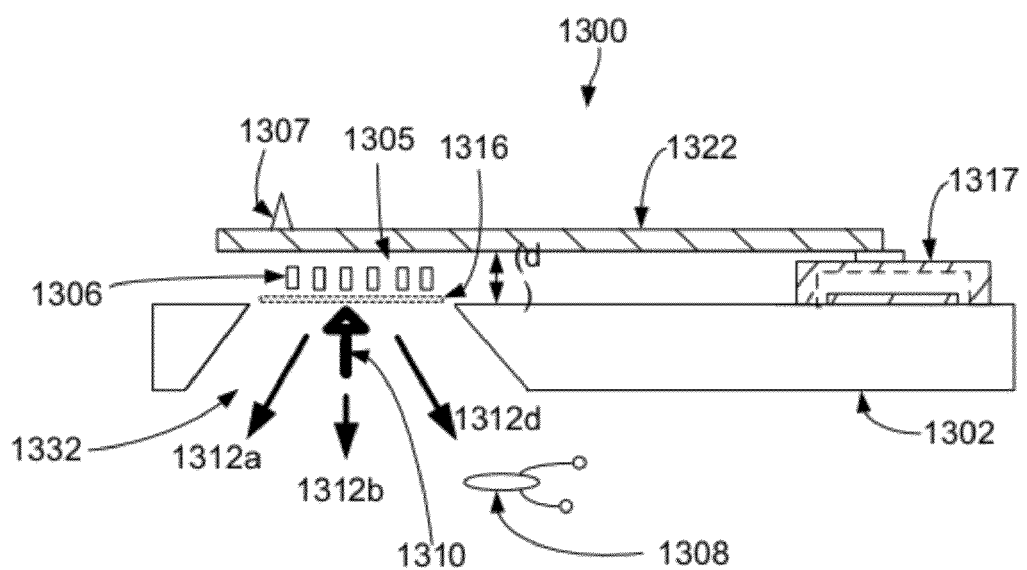
FIG. 13B shows a cross-sectional schematic diagram of another exemplary force sensor in accordance with the present teachings.

FIGS. 13A and 13B depict top-down and cross-sectional schematic diagrams of an exemplary force sensor 1300 in accordance with the present teachings. In FIGS. 13A and 13B, the force sensor 1300 can comprise a detection surface 1302, a grating 1306, a tip 1307, an electrostatic cantilever actuator flexible mechanical structure 1317, and a cantilever 1322. As shown in FIG. 13B, the force sensor 1300 can also include an optical port that can be created, for example, by etching a hole 1332 through the detection surface 1302. According to various embodiments, the grating 1306 can be a diffraction grating comprising a plurality of conductive fingers that can be deformable and that can be electrostatically actuated independently of the cantilever 1322 in order to control the relative gap 1305 distance (d) between the grating 1306 and the reflecting cantilever 1322. Further, the cantilever 1322 can have its own electrostatic actuation mechanism 1317. With the cantilever 1322 having its own electrostatic actuation mechanism 1317, displacement measurements can be optimized on each cantilever 1322 of an array of independent force sensor structures. With this capability, the initial positions from topography, misalignment with the imaged sample, and/or process non-uniformities can be measured and corrected.

In operation, as shown, for example, in FIG. 13B, a light 1310 can be directed at the cantilever 1322 through the hole 1332. The light 1310 is reflected from the cantilever and then diffracted by the grating 1306. Various diffraction orders 1312a-c can be detected by detectors 1308.

Figure 14:
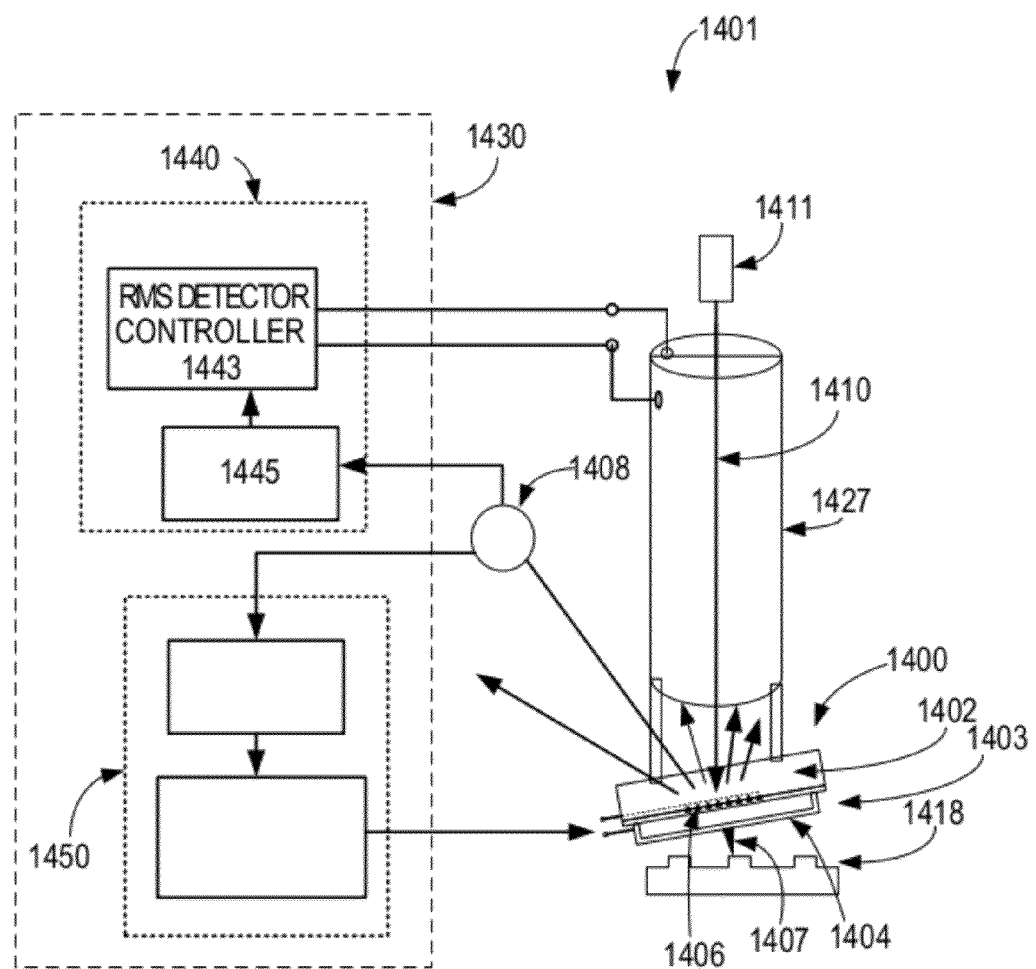
FIG. 14 shows a schematic diagram of an exemplary AFM system in accordance with the present teachings.

FIG. 14 shows a force sensor structure 1400 used in an AFM system 1401 according to various embodiments. The AFM system 1401 can comprise a force sensor 1403, a detector 1408, such as a photodiode, a light source 1411, such as a laser diode, and a computer 1430 comprising a first processor 1440 to generate a control loop for imaging material properties and a second processor 1450 to generate a control loop for fast tapping mode imaging. The second processor 1450 can further control an integrated electrostatic actuator, as described herein.

As shown in FIG. 14, the force sensor 1403 can be fabricated, for example, on a detection surface 1402 and placed on a holder 1428, which can be attached to an external piezoelectric actuator (piezo tube) 1427. The intensity of, for example, the +1st diffraction order of light diffracted by a grating 1406 in the force sensor 1403 is detected by the detector 1408 as the tip 1407 displacement signal. For example, with a 4 μm grating period and a 670 nm laser wavelength, the +1st diffraction order is reflected at a 9.6° angle from the grating normal. Tilting the detection surface 1402 by 6.2° with respect to the incident beam 1410 provides a total of 22° angular deflection. According to various embodiments with the force sensor 1403, significantly all of the light 1410 can be reflected from the grating 1406 and the flexible mechanical structure 1404, eliminating optical interference problems due to reflections from the sample 1418. This can provide a clean background for tip displacement measurements.

The performance of the AFM 1401 having a force sensor, such as those described herein, can be characterized using an integrated electrostatic actuator. For example, an optical interference curve with a DC bias range of 24-36 V was traced and the bias was adjusted for optimum sensitivity point at 30 V. The displacement sensitivity at this bias level was 204 mV/nm. The RMS noise measured in the full DC-800 kHz bandwidth of the photodetector 1408 was 18 mV RMS. This value, confirmed by spectrum analyzer measurements, corresponds to $1\times10^{-3}$ Å/$\sqrt{Hz}$ minimum detectable displacement noise with 1/f corner frequency of 100 Hz. Using the laser power available from the 0th and −1st orders and differential detection, this value can be lowered well below $5\times10^{-4}$ Å/$\sqrt{Hz}$ without increasing the laser power or using etalon detection. The dynamic response of a typical flexible mechanical structure was also measured using electrostatic actuation, indicating a resonance frequency of 720 kHz with a quality factor of 4.1, suitable for fast tapping mode imaging.

Two controller schemes interfaced with the AFM system 1401 can be used. The first scheme is used with the first processor 1440 comprising a controller 1443 and a RMS detector 1445 for material property measurement and imaging using transient interaction force signals. The Z-input of the piezo tube 1427 is driven to generate a 2 kHz 120 nm peak sinusoidal signal while the controller 1443 keeps constant the RMS value of the photo-detector signal generated by the force sensor 1403 when it taps on the sample 1418. The 2 kHz signal frequency is chosen as a compromise between the ability to generate adequate vertical (Z direction) displacement of the piezo tube and the frequency response of the internal RMS detector 1445 for a typical force sensor structure 1401. The second controller scheme is used with the second processor 1450 for fast tapping mode imaging. In this case, the Z-input of the piezo tube is disabled and the integrated electrostatic actuator is used to generate a 10 nm peak-to-peak free air tapping signal in the 500-700 kHz range as well as the signals to control the force sensor 1403 tip 1407 position keeping the RMS value of the tip vibration at the desired set point.

Figure 15A:
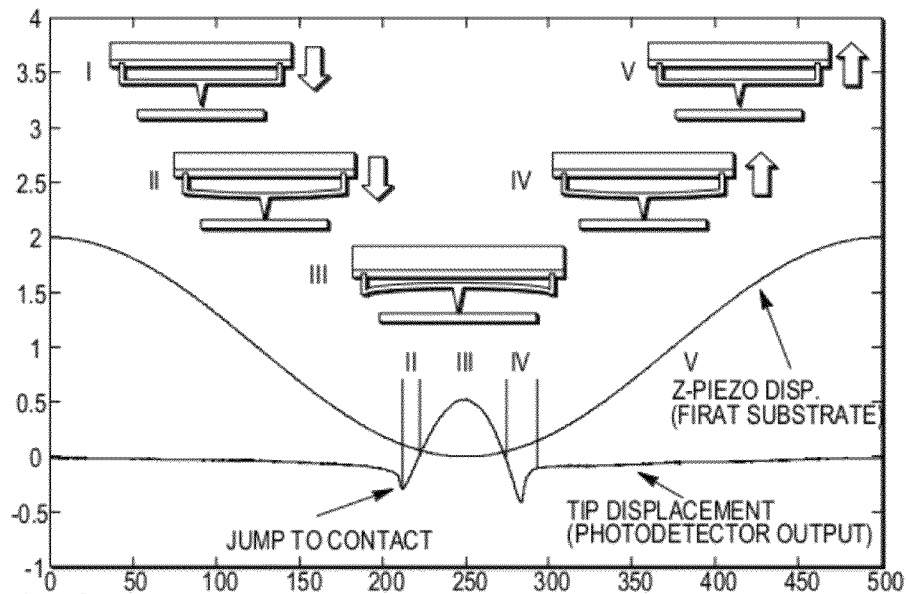
FIGS. 15A-15C show graphs of interaction intensity versus time for an exemplary force sensor in accordance with the present teachings.
Figure 15B:
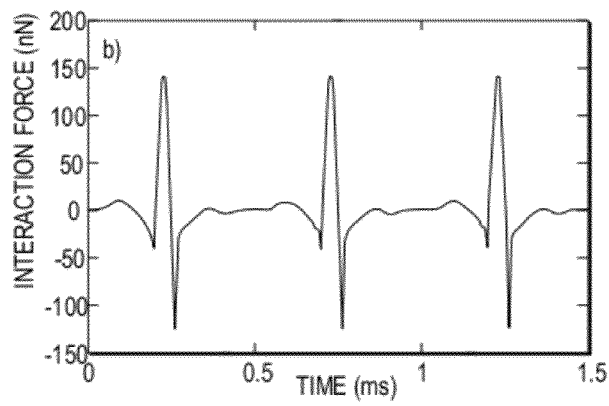
Figure 15C:
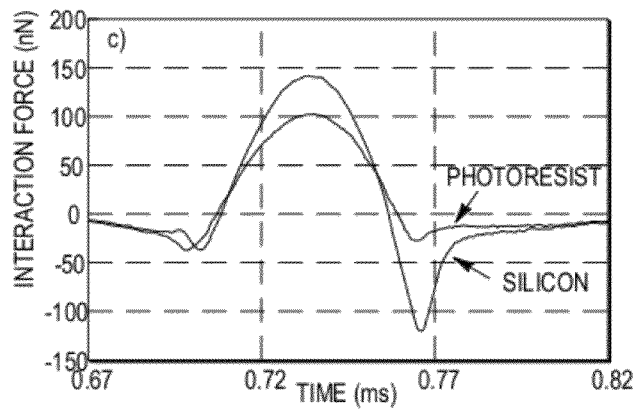

FIGS. 15A-15C show the results of a force sensor described herein used in a dynamic mode in an AFM system, such as that shown in FIG. 14. The results shown in FIGS. 15A-15C provide information about the transient interaction forces with a resolution that exceeds conventional systems. In this example, the detection surface, such as a substrate, can be oscillated, and can be driven by a suitable actuator. Both the attractive and repulsive regions of the force curve are traced as the tip 1407 contacts the sample 1418 during some phases (I-V) of each cycle. The inserts (i)-(v) in FIG. 15A show the shape of the flexible mechanical structure 1404 during different phases of a cycle while substrate is oscillated at 2 kHz by the Z-piezo. FIG. 15A also shows the measured detector output signal during each phase corresponding to each cycle. The detector 1408 output is proportional to the force acting on the tip 1407.

In this particular case, during phase I, the tip 1407 is away from the sample 1418 surface where it experiences long range attractive forces. When brought close to the surface, the tip 1407 jumps to contact (0.2 nm change in tip position, phase II) and remains in contact for about 14% of the cycle. In the middle of the period, the repulsive force applied to the sample 1418 reaches to a peak value of 163 nN (1.22 nm tip displacement, phase III). When the tip 1407 is withdrawn, the tip 1407 experiences capillary forces of 133 nN (phase IV) before breaking off from the liquid film on the sample 1418 surface (phase V). As shown in FIG. 15B, the controller 1443 of FIG. 14 can be used to stabilize the signal with a constant RMS, so that the output signal of the force sensor shows individual and repeatable taps on the sample 1418. The signals shown are averaged 100 times on a digitizing oscilloscope, and the noise level is less than 1 nN with 800 kHz measurement bandwidth.

An application of this mode of operation is the measurement of local visco-elastic properties. For example, in FIG. 15C individual tap signals obtained on (100) silicon (E=117 GPa) and photoresist (PR, Shipley 1813) (E=4 GPa) samples using a sensor with having a tip 50 nm radius of curvature were compared. The maximum repulsive force is significantly larger for the silicon sample even though the tip-sample contact time is less than that of photoresist (PR) indicating that the silicon is stiffer than PR. Consequently, the positive slope of the time signal during the initial contact to silicon sample is significantly larger than it is when in contact with the PR sample. The silicon sample also shows higher capillary hysteresis. Both of these results are consistent with existing models and data. Moreover, the tip 1407 can encounter different long range van der Waals or electrostatic forces on these two samples.

The results shown in FIGS. 15A-15C demonstrate a unique feature of the force sensors described herein for dynamic force measurements. In particular, the output signal is generated only when there is an interaction force on the tip. With broad bandwidth and high sensitivity, the force sensors enable direct measurement of transient interaction forces during each individual tap with high resolution and without background signal. This provides information on properties of the sample such as adhesion, capillary forces, as well as visco-elasticity.

Figure 16A:
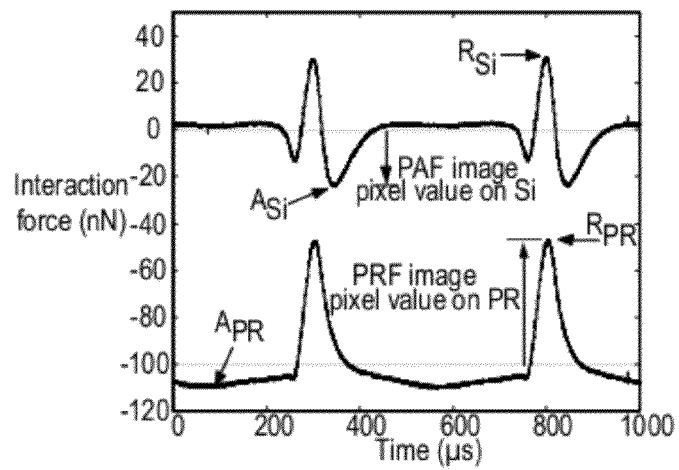
FIG. 16A shows a graph of interaction intensity versus time for an exemplary force sensor in accordance with the present teachings.

The force sensor can be used to image various material properties by recording at each pixel the salient features of the tap signal. For example, the AFM system 1401 shown in FIG. 14 can be used to monitor transient interaction forces. The first controller 1440 of system 1401 can be used to maintain a constant RMS value of the output signal while scanning the tapping tip 1407. FIG. 16A shows the transient tap signals on the PR and silicon regions of a sample that having 360 nm thick, 2 μm wide PR strips with 4 μm periodicity patterned on silicon surface. Significant differences exist between the tap signals in terms of both the attractive and repulsive forces acting on the tip 1407. For example, the silicon surface exhibits a much larger adhesion force when compared to the PR surface. Because the first controller 1440 attempts to maintain a constant RMS value over the sample, it forces the tip 1407 to indent more into the PR region. As such, the tip 1407 experiences a larger repulsive force. The shape of the individual tap signals in the attractive region has a strong dependence on the environment.

Figure 16B:
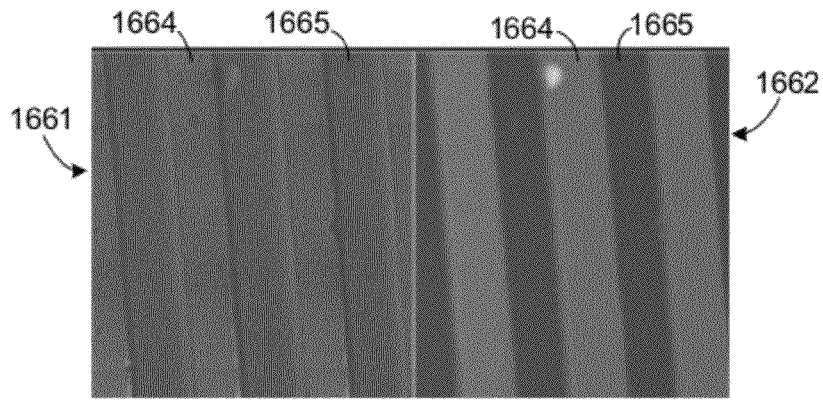
FIG. 16B shows a PAF image and a topography image of a sample using an exemplary force sensor in accordance with the present teachings.

To form an image in which sample adhesion dominates the contrast mechanism, a peak detector circuit can be used to record the peak attractive force (PAF) as the pixel value, such as points Asi, APR in FIG. 16A. Simultaneously, the sample topography can be recorded using a fixed RMS value set point. FIG. 16B shows the resulting adhesion (PAF) and topography images, 1661 and 1662, respectively, of the sample. In the topography image 1662, the stripes 1664 correspond to the 360 nm high PR pattern (Shipley 1805) and stripes 1665 correspond to the silicon surface. In the PAF image 1661, the silicon surface appears brighter than PR due to higher adhesion forces. By recording the peak repulsive force (PRF) as the pixel value, images where sample viscoelasticity dominates the contrast, such as at points Rsi, RPR in FIG. 16A, can be obtained.

Figure 16C:
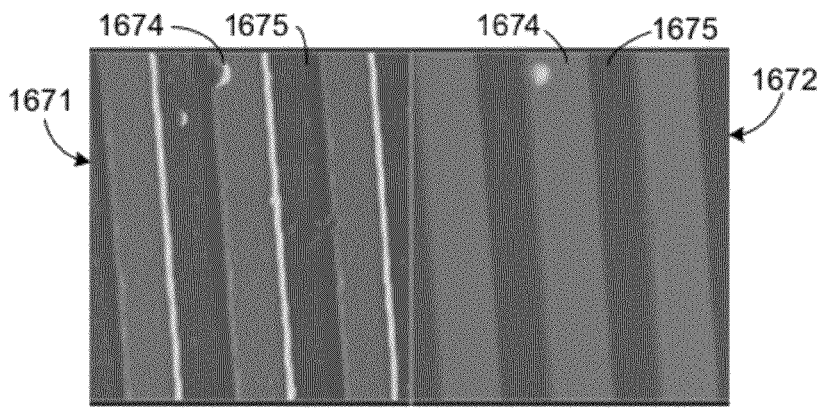
FIG. 16C shows a PRF image and a topography image of a sample using an exemplary force sensor in accordance with the present teachings.

Simultaneously recorded PRF and topography images of the same sample region are shown in FIG. 16C at 1671 and 1672, respectively. The PRF image 1671 shows a reversed contrast when compared to the PAF image, while the topography image is repeatable. The PR strips 1674 appear brighter in the PRF image as indicated by the individual tap signals shown in FIG. 16A. Also, many more contamination particles are adhered to the silicon 1665 surface as compared to the PR strips 1664, and these particles are seen with high contrast. This is consistent with higher adhesion measured on the silicon in the PAF image 1661.

Although a simple controller based on the RMS value set point is described in this embodiment, it is contemplated that different control schemes, such as those sampling individual tap signals at desired time instants and use those values in the control loop can also be used. For example, if the peak value of the repulsive force is kept constant as the control variable, images where the contact-to-peak force time determines the contrast—a direct measure of sample stiffness can be obtained. Several existing models can then be used to convert these images to quantitative material properties. Similarly, by detecting the attractive force peaks before and after the contact one can obtain quantitative information on the hysteresis of the adhesion forces.

FIGS. 17A and 17B show the results of fast tapping mode imaging of sample topography with a single sensor probe using the setup shown in FIG. 14. In this mode, the Z-input of the piezo tube 1427 is disconnected and used only for x-y scan. The integrated electrostatic actuator is used for both oscillating the tip 1407 at 600 kHz and controlling the flexible mechanical structure 1404 bias level in order to keep the oscillation amplitude constant as the tapping mode images are formed.

A standard calibration grating with 20 nm high, 1 μm wide, sharp steps with 2 μm periodicity was used as the fast imaging sample (NGR-22010 from Veeco Metrology). FIG. 17A shows the images of a 4 μm×250 nm area (512×16 pixels) of the grating with line scan rates of 1 Hz, 5 Hz, 20 Hz, and 60 Hz. FIG. 17B shows the cross sectional profiles of individual scan lines for each image. The AFM system 1401 had an x-y scan capability that can go up to 60 Hz.

Figure 17C:
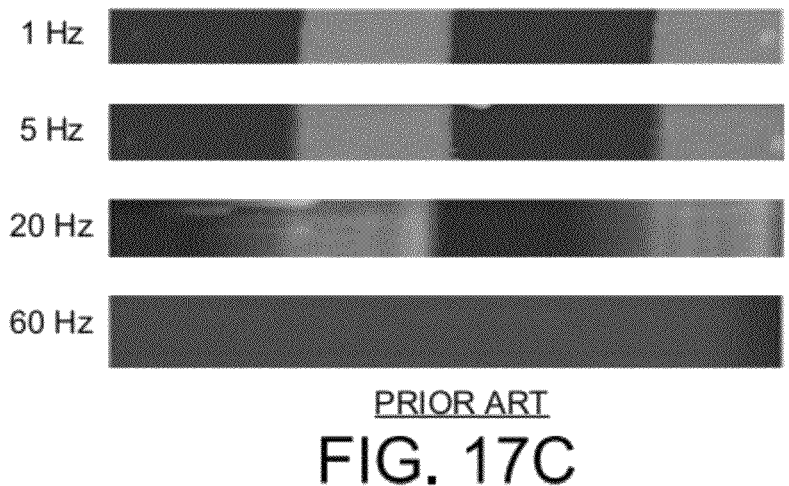
FIG. 17C shows a topographical image of sample in FIG. 17A made using a conventional AFM system.
Figure 17D:
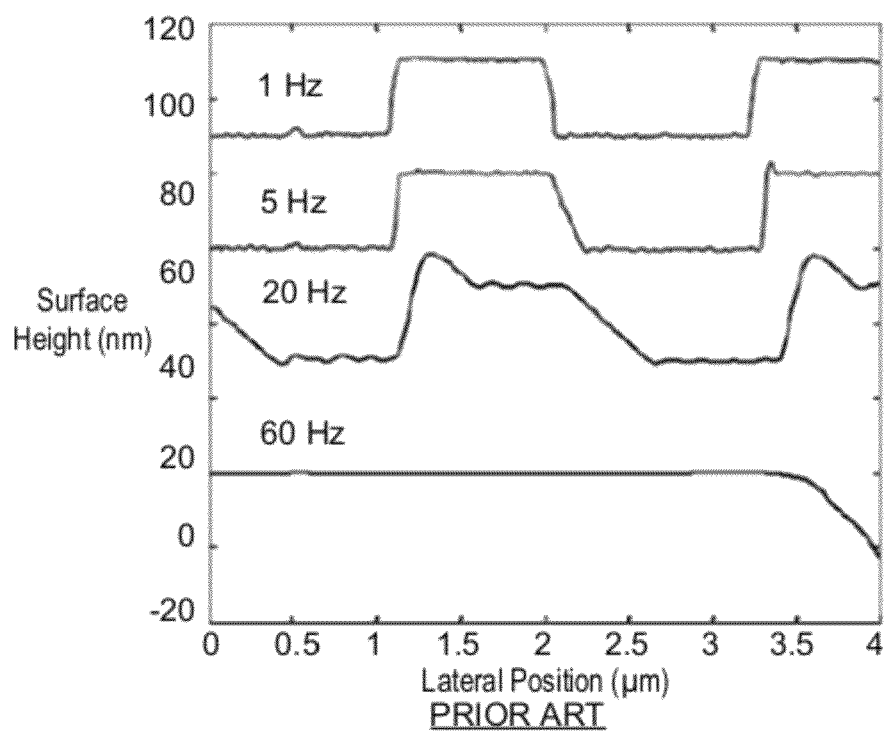
FIG. 17D shows line scans of the sample shown in FIG. 17C measured at different speeds using a conventional AFM system.

For comparison, FIGS. 17C and 17D, show the tapping mode images and line scans using a conventional AFM system on the same sample used in the example of FIGS. 17A and 17B. The commercial AFM system used a tapping mode cantilever. The cantilever was made of silicon and had a 300 kHz resonance frequency (TESP-A from Veeco Metrology). In this case, the tapping piezo on the cantilever holder was used as the actuator.

As can be seen in the figures, AFM systems described herein are able to resolve the grating with at least a 20 Hz line scan rate, and in some cases a 60 Hz line scan rate. In contrast, conventional AFM systems are not able to follow the sharp steps starting at 5 Hz, and fail to produce a viable image after 20 Hz line scan rate. The imaging bandwidth of the AFM system 1401 described herein was about 6 kHz. However, controlling the dynamics of the air flow in and out of etch holes on two sides of the flexible mechanical structure, such as those shown at 280 in FIG. 2C. With a sealed cavity, the imaging bandwidth of various force sensors described herein can be increased to more than 60 kHz. Moreover, since the force sensor unit is a well damped system even in air, methods other than RMS detection can be used to implement faster controllers.

Figure 18:
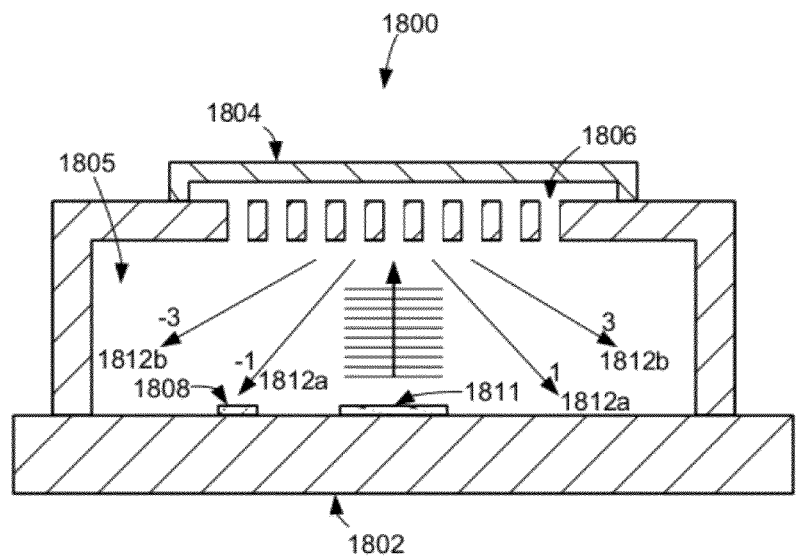
FIG. 18 shows a cross-sectional schematic diagram of another exemplary force sensor in accordance with the present teachings.

FIG. 18 depicts a cross-sectional schematic diagram of another exemplary force sensor unit 1800 in accordance with the present teachings. FIG. 18 shows a light source 1811 and a photodiode 1808 on the surface of an opaque, rigid, detection surface 1802. The detection surface 1802 can be a printed circuit board, a silicon wafer, or any other solid material. Furthermore, the light source 1811 and photodiode 1808 can be constructed or sourced externally and attached to the detection surface or fabricated directly into the material using integrated circuit or micromachining fabrication techniques.

The light source 1811 can be an optical fiber or the end of a micro-fabricated waveguide with an appropriate reflector to direct the light to the desired location in the force sensor unit 1800, such as a diffraction grating 1806. The optical diffraction grating structure 1806 exists above the light source 1811, and is characterized by alternating regions of reflective and transparent passages. A gap 1805 forming a cavity is formed between the grating 1806 and the detection surface can be sealed at some desired pressure (including low pressures) with any gas or gas mixture, or can be open to ambient. Further, a flexible mechanical structure 1804 (also called a reflective surface or reflective diaphragm) exists above the diffraction grating 1806 that reflects light back towards the detection surface 1802. The diffraction grating 1806 and the reflective surface 1804 together form a phase sensitive diffraction grating.

When illuminated with the light source 1811 as shown, diffracted light reflects back towards the detection surface 1802 in the form of diffracted orders 1812a and 1812b with intensity depending on the relative position between the reflective surface 1804 and the diffraction grating 1806, or the gap 1805 thickness. The diffracted orders 1812a and 1812b emerge on both the right and left side and are traditionally numbered as shown in FIG. 18. For the phase sensitive diffraction grating with 50% fill factor, i.e. reflective and transparent passages with the same width, only the zero order and all odd orders emerge. The intensity of any one or any subset of these orders can be measured with photo-diodes 1808 to obtain information about the relative distance between the diffraction grating 1806 and the reflective surface 1804. The angles of the orders are determined by the diffraction grating period, $\Lambda g$, and the wavelength of the incident light, $\lambda$. For example, in the far field the angle of the order n, $\theta n$, will be given by the relation [1]:

$$\sin(\theta_n) = n \frac{\lambda}{\Lambda_g} \qquad [1]$$

Figure 19:
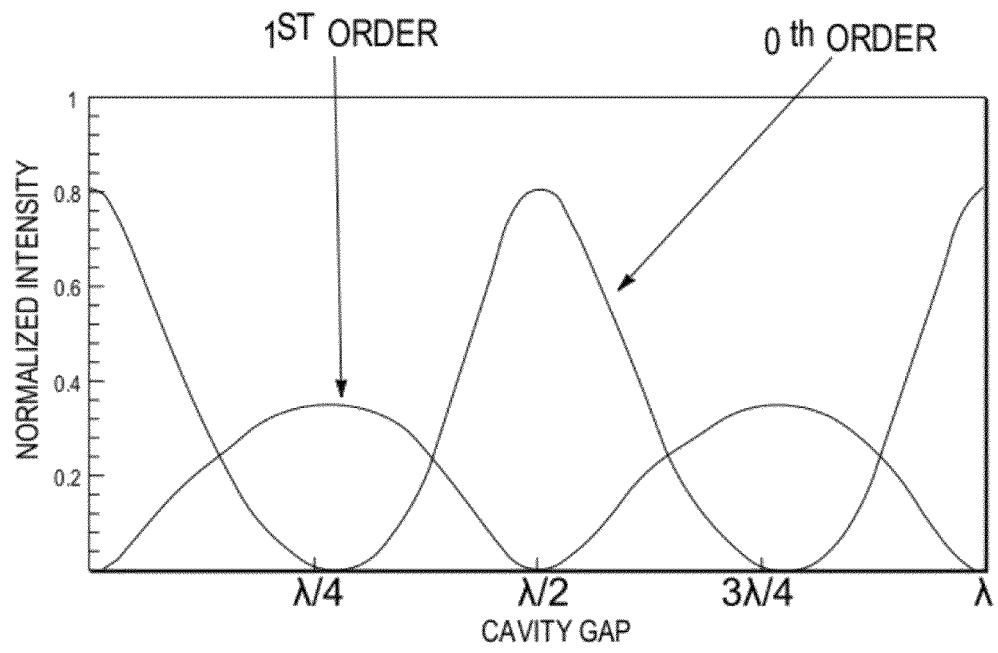
FIG. 19 shows a graph plotting normalized intensity versus gap thickness using a force sensor in accordance with the present teachings.

In order to illustrate how the intensity of the reflected orders depends on the gap thickness, the normalized intensity of the zero and first orders are plotted versus the gap in FIG. 19 assuming normal incidence. The remaining odd orders (i.e. 3rd, 5th, etc.) are in phase with the 1st but have decreasing peak intensities. This behavior can be obtained when the light source 1811 remains coherent over the distance between the reflector and the diffraction grating 1806.

Furthermore, the diffracted orders can be steered to desired locations using structures such as Fresnel lenses. For this purpose, the gratings 1806 can be curved or each grating finger can be divided into sections of sub-wavelength sized gratings.

Also using wavelength division multiplexing, light with different wavelengths can be combined and used to illuminate a multiplicity of force sensors with different grating periods. The reflected diffraction orders from different force sensors can either be converted to electrical signals by separate photodetectors, or the reflected light at different wavelengths can be combined in an optical waveguide or optical fiber to minimize the number of optical connections to a processor that subsequently decodes the information carried at different wavelengths. Therefore, a multiplicity of force sensors can be interrogated using a single physical link or a reduced number of physical links to a processing system.

According to various embodiments, such as chemical and biological sensors, the reflective surface 1804 can be made of single material or a multi layered material that changes its optical properties, such as reflectivity, in response to a chemical or biological agent. Similarly, the reflective surface 1804 can be a micromachined cantilever or a bridge structure made of single or layered material that deforms due to thermal, chemical, magnetic, or other physical stimulus. For example, an infrared (IR) sensor can be constructed by having a bimorph structure including an IR absorbing outer layer and a reflective layer facing the light source 1811. In other embodiments, such as a microphone or a pressure sensor, the reflector 1804 can be in the shape of a diaphragm.

In many applications, moving or controlling the position of the reflective surface 1804 may be desired for self-calibration, sensitivity optimization, and signal modulation purposes. For example, if the reflective surface 1804 is a diaphragm or flexible mechanical structure, as in the case of a microphone or a capacitive micromachined transducer, vibrating the diaphragm to produce sound in a surrounding fluid may be desired for transmission and self-calibration. Also, while measuring the displacement of the diaphragm, controlling the nominal gap 1805 height to a position that will result in maximum possible sensitivity for the measurement may be desired. These positions correspond to points of maximum slope on the curves in FIG. 19, where it can be seen graphically that a change in gap thickness results in a maximum change in intensity of the diffracted order. These examples can use an added actuation function that can be accomplished with electrostatic actuation. In one exemplary embodiment, the entire diaphragm structure 1804 or just a certain region thereof can be made electrically conductive. This can be accomplished by using a non-conductive material for the reflective surface 1804 such as a stretched polymer flexible mechanical structure, polysilicon, silicon-nitride, or silicon-carbide, and then making the material conductive in the desired regions either through doping or by depositing and patterning a conductive material such as aluminum, silver, or any metal or doping the flexible mechanical structure 1804, such as when the flexible mechanical structure comprises polysilicon.

In another exemplary embodiment, the entire diffraction grating 1806 or a portion of the grating 1806 can be made conductive. The flexible mechanical structure 1804 and diffraction grating 1806 can together form a capacitor which can hold charge under an applied voltage. The strength of the attraction pressure generated by the charges can be adjusted by controlling the voltage, and precise control of the flexible mechanical structure 1804 position is possible.

FIGS. 20A and 20B demonstrate this function. First, increasing voltage levels were applied to pull the flexible mechanical structure 1804 towards the detection surface 1802, which resulted in decreasing gap 1805 height (i.e. a movement from right to left on the curve in FIG. 19). The change in light intensity of the first diffracted order that resulted was measured with a photodiode and plotted at the top. To illustrate why controlling the flexible mechanical structure position may be important, a displacement measurement of the flexible mechanical structure 1804 was made at different gap 1805 heights as follows. At different applied voltages, sound was used to vibrate the flexible mechanical structure 1804 with constant displacement amplitude and the resulting change in light intensity of the first diffracted order was again measured with a photodetector. As shown in the bottom of FIG. 20A, voltage levels that move the gap height to a point corresponding to a steep slope of the optical curve are desirable as they produce larger measurement signals for the same measured input. Although sound pressure was used to displace the flexible mechanical structure 1804, the device can be tailored to measure any physical occurrence, such as a change in temperature or the exposure to a certain chemical, or an applied force so long as the flexible mechanical structure 1804 was designed to displace as a result of the occurrence.

This displacement measuring scheme has the sensitivity of a Michelson interferometer, which can be used to measure displacements down to $1 \times 10^{-6}$ Å for 1 Hz bandwidth for 1 mW laser power. Various embodiments disclosed herein can provide this interferometric sensitivity in a very small volume and can enable integration of light source, reference mirrors and detectors in a mechanically stable monolithic or hybrid package. This compact implementation further reduces the mechanical noise in the system and also enables easy fabrication of arrays. The high sensitivity and low noise achieved by the various embodiments far exceed the performance of other microphones or pressure sensors based on capacitive detection.

Figure 21:
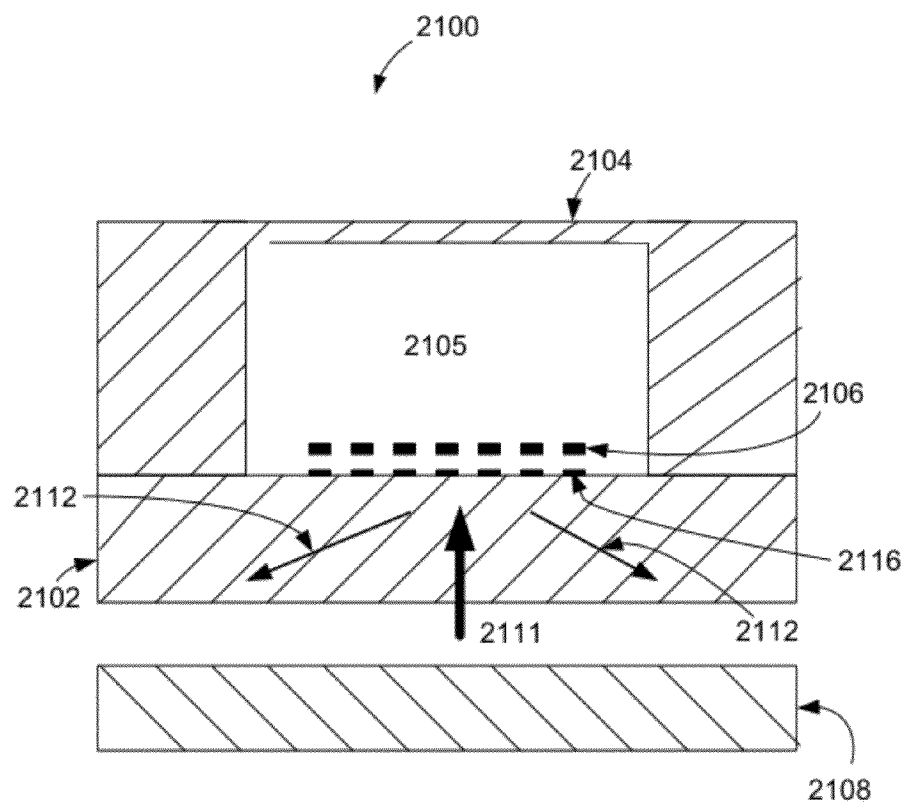
FIG. 21 shows a cross-sectional schematic diagram of another exemplary force sensor in accordance with the present teachings.

FIG. 21 depicts a cross-sectional schematic diagram of another exemplary force sensor 2100 in accordance with the present teachings. FIG. 21 shows a force sensor comprising a detection surface 2102, which allows the light source 2111 to be placed at a location behind the substrate 2102. The detection surface 2102 also allows the reflected diffracted orders 2112 to pass through, and the light intensity of any of these orders can measured at a location behind the substrate 2102. The force sensor 2100 can also comprise a flexible mechanical structure 2104, such as a diaphragm, and a diffraction grating 2106 that can be made moveable so that its position may be controlled via electrostatic actuation, with a region of the substrate serving as a bottom electrode 2116. Changing the flexible mechanical structure—grating gap thickness can be used to optimize the displacement sensitivity of the flexible mechanical structure, as discussed above with reference to FIG. 18.

Several material choices exist for the detection surface 2102 that is transparent at the wavelength of the incident light. These include quartz, sapphire, and many different types of glass, and it can be silicon for light in the certain region of the IR spectrum. Furthermore, several manufactures sell these materials as standard 100 mm diameter, 500 µm thick wafers, which makes them suitable for all micro-fabrication processes including lithographic patterning. As in the force sensor 1800, several different material types may be used for the flexible mechanical structure, and the cavity between the platform and diaphragm may be evacuated or filled with any type of gas mixture.

The diffraction grating 2106 may be made of any reflective material, as long as the dimensions are chosen to produce a compliant structure that may be moved electrostatically. As explained for force sensor 1800, electrostatic actuation requires a top and bottom electrode. According to various embodiments, the diffraction gating 2106 can serve as the top electrode and the bottom electrode 2116 can be formed on the substrate 2102. Furthermore, the distance between these electrodes can be small (order of a micrometer) to be able to perform the actuation with reasonable voltage levels (<100V). For example, for force sensor 2100 this means regions of both the diffraction grating 2106 and the detection surface 2102 can be made electrically conductive. If a metal or any other opaque material is chosen to form the bottom electrode 2116 on the detection surface 2102, the electrode region should exist in a region that will not interfere with the propagation of light towards the diffraction grating 2106 and the flexible mechanical structure 2104. Alternatively, a material that is both optically transparent and electrically conductive, such as indium-tin oxide, may be used to form the bottom electrode 2116 on the platform. Force sensor 2100 enables one to use the advantages of electrostatic actuation while having a large degree of freedom in designing the flexible mechanical structure 2104 in terms of geometry and materials.

Figure 22:
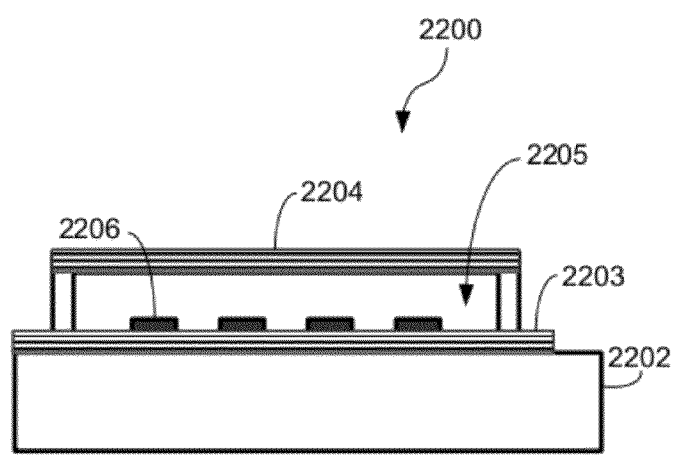
FIG. 22 shows a cross-sectional schematic diagram of another exemplary force sensor in accordance with the present teachings.

FIG. 22 depicts a cross-sectional schematic diagram of another exemplary force sensor in accordance with the present teachings. FIG. 22 shows the implementation of a resonant-cavity-enhanced (Fabry-Perot cavity) optical force sensor 2200 that can be used to improve displacement sensitivity, which may be defined as the intensity variation of the diffracted beam per unit flexible mechanical structure displacement (i.e., the change of the cavity gap) due to the external excitation. The force sensor 2200 can comprise a detection surface 2202, two parallel mirror layers, such as a bottom mirror 2203 and a top mirror 2204, and a grating 2206. According to various embodiments, the bottom mirror 2203 can be formed on the detection surface 2202 and can include the grating 2206. Further, the top mirror 2204 can also serve as a diaphragm or flexible mechanical structure.

The bottom mirror 2203 and the top mirror 2204 can be separated by the grating-embedded gap or cavity 2205, as illustrated in FIG. 22. As mentioned, the flexible mechanical structure 2204 can have a high reflectance and can act as the top mirror, and the bottom mirror 2203 can be placed beneath the diffraction grating 2206. The mirror layers can be built, for example, using a thin metal film, a dielectric stack of alternating quarter-wave ($\lambda/4$) thick media, or combination of these two materials.

Figure 23A:
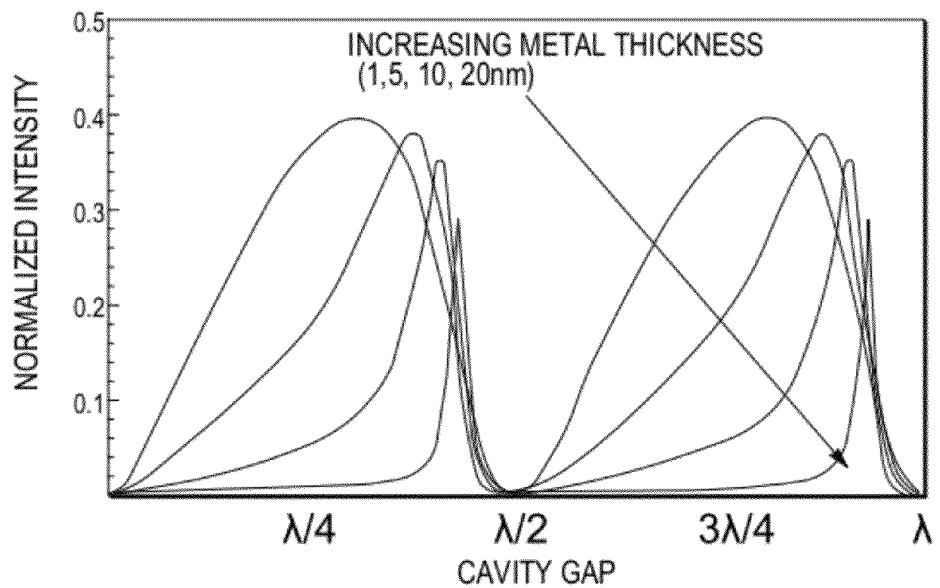
FIG. 23A shows a graph plotting normalized intensity versus gap thickness using a force sensor in accordance with the present teachings.
Figure 23B:
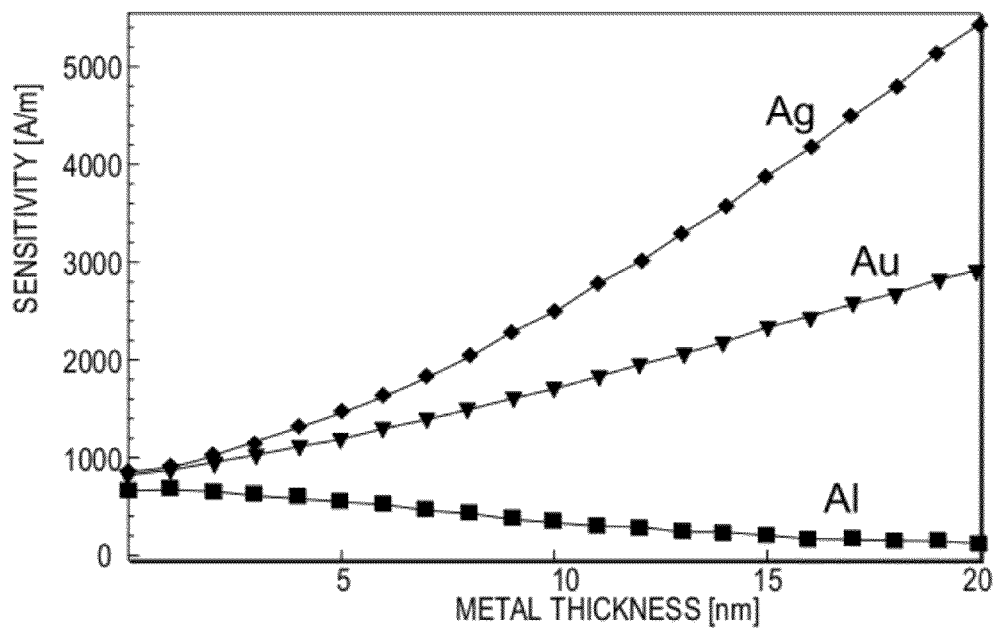
FIG. 23B shows a graph plotting sensitivity versus metal thickness using a force sensor in accordance with the present teachings.

FIG. 23A shows the calculated intensity of the first order versus the gap 2205 for the case of a metal mirror made of silver, but any other metal with a high reflectivity and low loss at the desired wavelength can be used. It can be noticed that the change in the diffracted order intensity with cavity gap 2205 in the resonant-cavity-enhanced optical force sensor 2200 departs from that shown in FIG. 19, depending on optical properties of the mirror layers, such as reflectance. As seen in FIG. 23A, the slope of the intensity curve increases with increasing metal layer thickness, hence the mirror reflectivity. The sensitivity in the unit of photocurrent per flexible mechanical structure displacement (A/m) is also evaluated when the intensity of the first-order, diffracted from an incident light of 1 mW optical power, is detected by a detector, such as a photo-diode with 0.4 A/W responsivity. The calculation result for various metals is presented in FIG. 23B. For example, the displacement sensitivity can be improved by 15 dB using a 20 nm thick silver layer for the mirror. For different metals with higher optical loss, the improvement may be less or the sensitivity may decrease as in case of aluminum.

FIG. 24A shows the experimental data obtained by two structures with and without an approximately 15 nm thick silver mirror layer with an aluminum diaphragm. FIG. 24A shows data for an embodiment without a mirror. Similar to FIG. 20A, increasing the DC bias voltage helps one to trace the intensity curve in FIG. 24A from right to left. Because there is no Fabry-Perot cavity formed in this embodiment, the intensity curve is smooth.

Figure 24C:
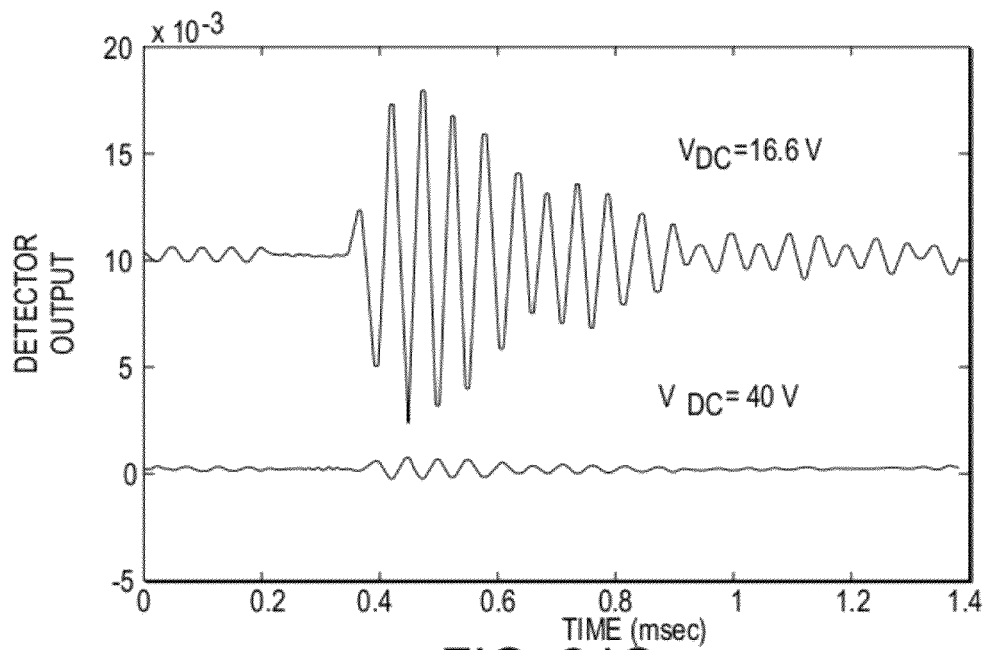

FIG. 24B shows the same curve for the Fabry-Perot cavity with a silver mirror. In this embodiment, the intensity curve has sharper features and large slopes around 16-18V DC bias. This is similar to the change predicted in FIG. 23A. The sensitivity dependence is also verified by subjecting the diaphragm to an external sound source at 20 kHz and recording the first order intensity at different DC bias levels. FIG. 24C shows the result of such an experiment and verifies that the optical detection signal is much larger for the 16V DC bias as compared to 40V, where the average intensity is the same. For a regular microphone without the Fabry-Perot cavity structure, one would expect to obtain larger signal levels with 40V DC bias.

Figure 25:
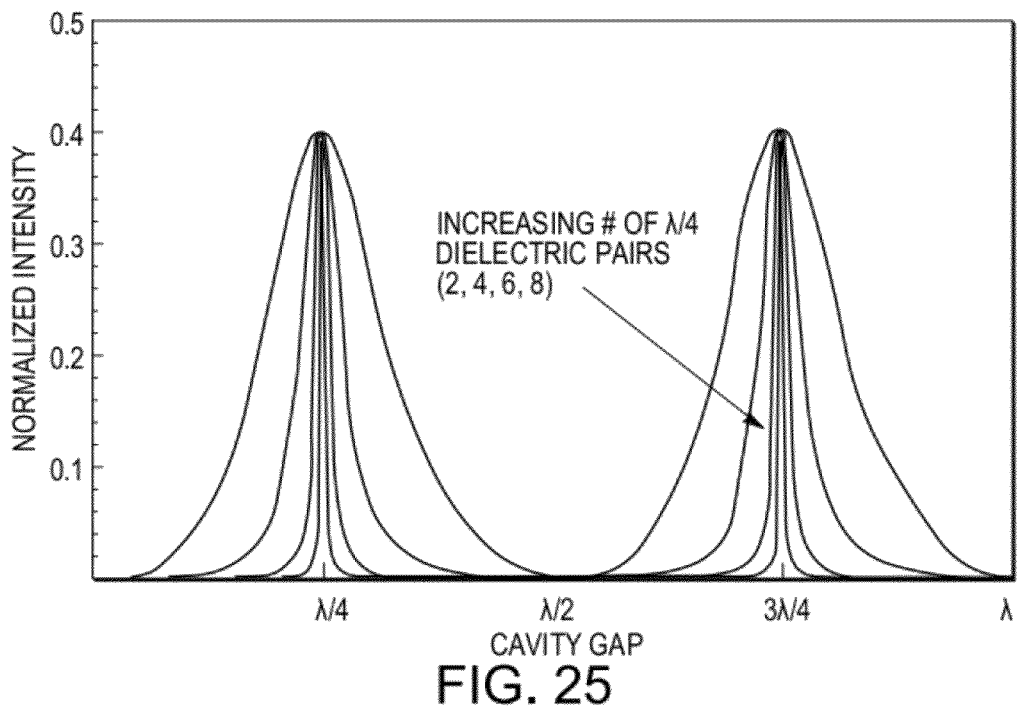
FIG. 25 shows a graph plotting normalized intensity versus gap thickness using a force sensor in accordance with the present teachings.

FIG. 25 shows the calculated intensity of the first order versus the gap 2205 for the case of the dielectric mirrors. In this embodiment the dielectric mirrors are made of silver and SiO2/Si3N4 pairs but any other dielectric material combination resulting in a high reflectivity and low loss at the desired wavelength can be used. The reflectance of the mirror can be controlled by the change in the thickness of the metal film and the number of alternating dielectric pairs for a given choice of mirror materials. In FIG. 25, the number of pairs is increased from 2 to 8 and which in turn increases the slope of the intensity curve resulting in a higher sensitivity.

In contrast to the dielectric mirror case, peak intensity amplitude of the first order decreases with the metal mirror reflectance due to the optical loss in the metal film (FIG. 23A), and thus metals of low absorption loss provide good results for the metal-mirror applications. In addition, the optimal bias position moves toward to a multiple of $\lambda/2$ with the reflectance of the metal mirror. However, the optimal bias position can be easily achieved through electrostatic actuation of the flexible mechanical structure 2204.

The scheme of the resonant-cavity-enhanced optical force sensor can be also applied to the other microstructures described herein with a simple modification of fabrication process.

Figure 26:
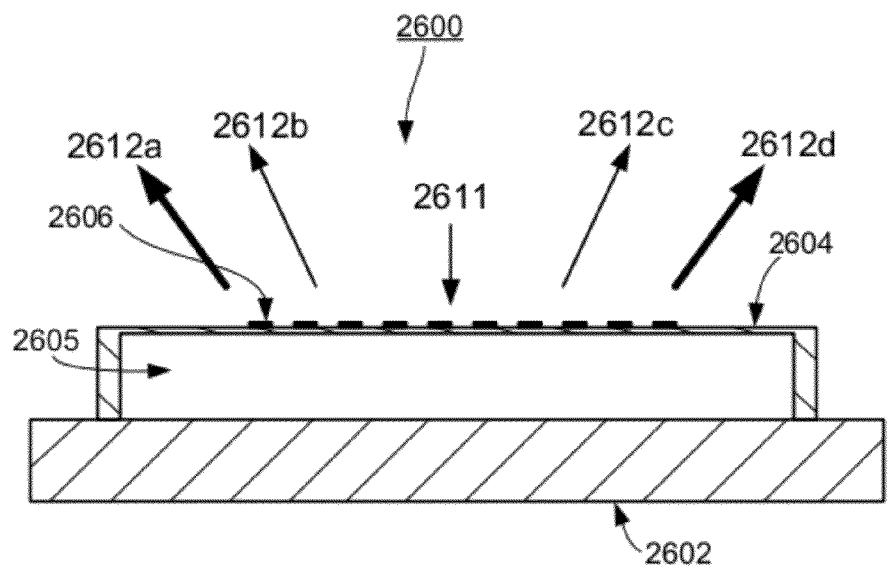
FIG. 26 shows a cross-sectional schematic diagram of another exemplary force sensor in accordance with the present teachings.

FIG. 26 depicts a cross-sectional schematic diagram of another exemplary force sensor in accordance with the present teachings. FIG. 26 shows a force sensor 2600 comprising a detection surface 2602, a flexible mechanical structure 2204 (also called a diaphragm), a gap 2605 (also called a cavity), and a grating 2606. The grating 2606 can be reflective and can be formed on the flexible mechanical structure 2204, which can be transparent. Further, the grating can comprise reflective diffraction fingers. According to various embodiments, the detection surface 2602 can be reflective. The force sensor 2600 can form a phase-sensitive diffraction grating when illuminated from the topside of the flexible mechanical structure 2204 as shown in FIG. 26. Similar to the embodiment shown in FIG. 18, the zero and all odd orders of light are reflected back and have intensities that depend on the gap 2605 between the diffraction grating 2606 and the detection surface 2602. The thickness of the gap 2605 can also include the thickness of the flexible mechanical structure 2604, which may be made of any transparent material. Examples of transparent materials include silicon dioxide, silicon nitride, quartz, sapphire, or a stretched polymer membrane such as parylene. Because the detection surface 2602 is reflective, any material, including semiconductor substrates or plastics, can suffice given that they are coated with a reflective layer, such as metal. To add electrostatic actuation, as described herein, a region of both the detection surface 2602 and the flexible mechanical structure 2604 can be made electrically conductive. For the flexible mechanical structure 2604, this can be accomplished by using a material that is both reflective and electrically conductive for the diffraction grating 2606. For example, any metal would work. In various embodiments, because the light source 2611 and detectors (not shown) exist on the top side of the flexible mechanical structure 2604, this particular embodiment offers remote sensing capabilities. For example, if measuring the displacement of the flexible mechanical structure 2604 due to a change in pressure is desired (as would be the case for a pressure sensor or a microphone), the detection surface 2602 can be attached to a surface and the light source 2611 and detectors can be stationed in a remote location, not necessarily close to the diaphragm.

In addition to remote measurements, the force sensor 2600 can be remotely actuated to modulate the output signal. For example, an acoustic signal at a desired frequency can be directed to the flexible mechanical structure 2604 with the grating 2606 and the output signal can be measured at the same frequency using a method such as a lock-in amplifier. The magnitude and phase of the output signal can give information on the location of the flexible mechanical structure 2604 on the optical intensity curve in shown in FIG. 19, which in turn may depend on static pressure, and other parameters such as temperature, etc. Similar modulation techniques can be implemented using electromagnetic radiation, where an electrostatically biased flexible mechanical structure with fixed charges on it can be moved by applying electromagnetic forces. In this case, the flexible mechanical structure can be made of some dielectric material with low charge leakage.

Figure 27:
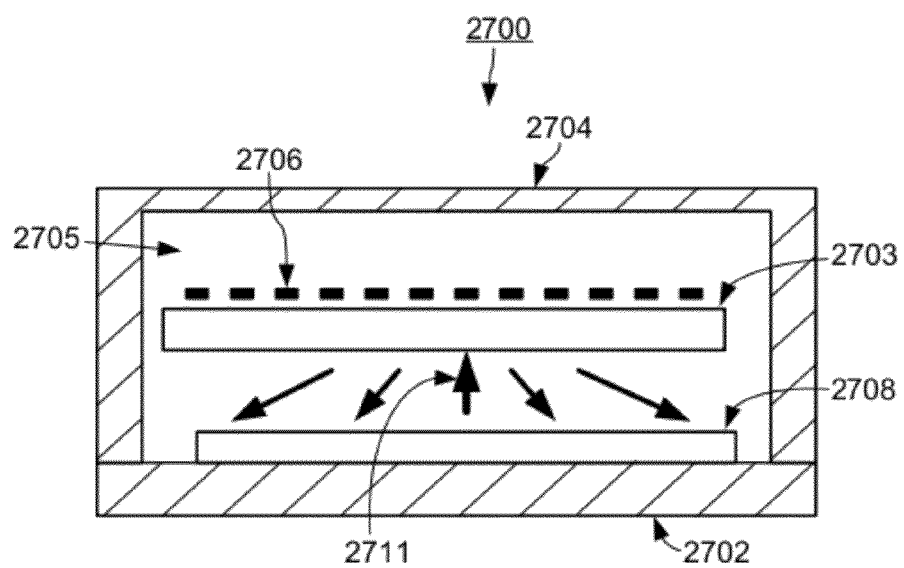
FIG. 27 shows a cross-sectional schematic diagram of another exemplary force sensor in accordance with the present teachings.

FIG. 27 depicts a cross-sectional schematic diagram of another exemplary force sensor in accordance with the present teachings. FIG. 27 shows a force sensor 2700 comprising a detection surface 2702, a transparent support comprising electrodes 2703, a flexible mechanical structure 2704 (also called a diaphragm), a gap 2705 (also called a cavity), a grating 2706, and a detector 2708. The detection surface 2702 in force sensor 2700 can be transparent so that the light source and detectors 2708 can be placed at a location behind the detection surface. However, placing the light source and detectors 2708 on the surface of the detection surface is equally viable and allows the usage of substrates such as silicon wafers or printed circuit boards. According to various embodiments, the grating 2706 can be moveable. As discussed herein, controlling the gap 2705 between the grating 2705 and the reflective flexible mechanical structure 2704 can be used to optimize detection sensitivity.

Various methods can be used to control the thickness of the gap 2705, such as, for example, controlling the flexible mechanical structure 2704 position, the grating 2706 position, or both. Furthermore, the force sensor 2700 allows placement of the grating 2706 anywhere in the cavity 2705 between the light source 2708 and the flexible mechanical structure 2704.

According to various embodiments, the use of highly reflective semi-transparent layers to enhance displacement sensitivity using Fabry-Perot cavity, as described by, for example the embodiment shown in FIG. 22. For example, a Fabry-Perot cavity can be implemented with any of the other embodiments mentioned so far, when using semitransparent layer is placed in close proximity to the diffraction grating For example, the sensors shown in FIGS. 18 and 21 can place a semi-transparent layer on the top or bottom surface of the grating. Further, the force sensor shown in FIG. 26 can place a semi-transparent layer on either the top or backside of the flexible mechanical structure, which is where the diffraction grating is located in this case.

Figure 28A:
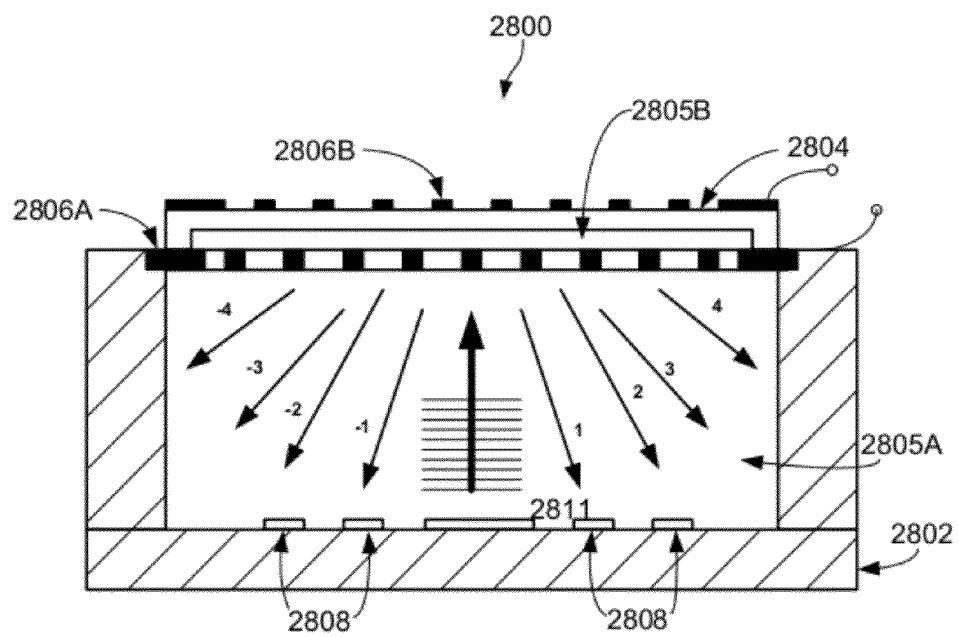
FIG. 28A shows a cross-sectional schematic diagram of another exemplary force sensor in accordance with the present teachings.

For example, FIG. 28A depicts a cross-sectional schematic diagram of another exemplary force sensor in accordance with the present teachings. FIG. 28A shows a force sensor 2800 comprising a detection surface 2802, a flexible mechanical structure 2804 (also called a diaphragm), a first gap 2805A (also called a first cavity), a second gap 2805B (also called a second cavity), a first grating 2806A (also called a reference grating), a second grating 2806B (also called a sensing grating), a detector 2808, and a light source 2811. The second grating 2806B can be formed on the flexible mechanical structure 2804, which can be transparent. Moreover, the flexible mechanical structure 2804 can be formed over the first grating 2806A.

In this embodiment, the flexible mechanical structure 2804 is or has a reflective diffraction grating, second grating 2806B, rather than a mirror-like uniform reflector surface described above. Moreover, the second grating 2806B on the flexible mechanical structure 2804 reflector can have the same periodicity as the first grating 2806B, but can be offset and can have diffraction fingers whose widths are smaller than the gap between the first grating 2806A. This offset allows some of the incident light to pass through. This structure, as shown in FIG. 28A, allows some of the incident light from light source 2811 to transmit through the whole force sensor 2800 and also introduces new diffraction orders in the reflected field. As such, this provides a different kind of phase grating than those described above.

Figure 28B:
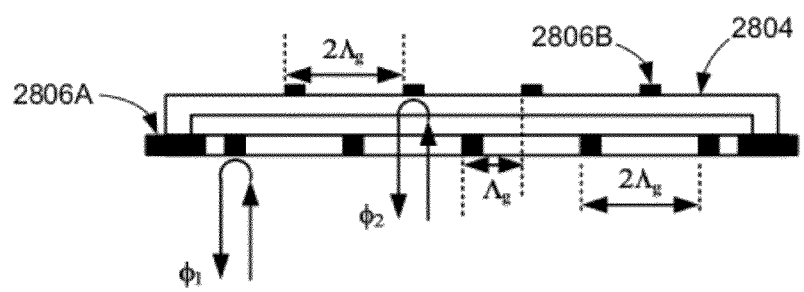
FIG. 28B shows a cross-sectional schematic diagram of a portion of the force sensor shown in FIG. 28A in accordance with the present teachings.

FIG. 28B is provided to assist in understanding the operation of a sensor having two gratings. For example, one can consider the phase of the light reflected from the first grating 2806A (also called the reference grating) (φ1) and the second grating 2806B on the flexible mechanical structure 2804 (φ2). When the difference between (φ1 and (φ2 is 2k□, k=0, 2, 4, . . . , the apparent period of the grating is Λg (apparent reflectivity of 1, 0, 1, 0 regions assuming perfect transmission through the transparent diaphragm 2804) and the even diffraction orders are reflected with angles $$\sin(\theta_n) = n\frac{\lambda}{\Lambda_g}, n = 0, \pm 2, \pm 4 \ldots \quad [2]$$

In contrast, when the difference between (φ1 and (φ2 is m□, m=1, 3, 5, . . . , the apparent period of the grating is 2Λg (apparent reflectivity of 1, 0, −1, 0, 1 regions assuming perfect transmission through the flexible mechanical structure 2804) and the odd diffraction orders are reflected with angles $$\sin(\theta_n) = n\frac{\lambda}{2\Lambda_g}, n = 1, \pm 3, \pm 5 \ldots \quad [3]$$

Here it is assumed that the width of the reflective fingers on the reference grating 2806S and the second grating 2806B on the flexible mechanical structure 2804 are the same. This does not have to be the case if the interfering beams go through different paths and experience losses due to reflection at various interfaces and also incidence angle variations. The diffraction grating geometry can then be adjusted to equalize the reflected order intensities for optimized interference.

In this double grating structure, shown, for example in FIG. 28A, the intensity of the odd and even numbered orders change with 180° out of phase with each other when the gap 2805B between the reference grating 2805A and sensing grating 2806B changes. The even numbered diffraction orders are in phase with the zero order reflection considered in the previous embodiments.

One advantage of having other off-axis even diffraction orders in phase with the specular reflection is that it enables one to easily use differential techniques. This is achieved by taking the difference of the outputs of two detectors positioned to detect odd and even orders, respectively. Hence the common part of the laser intensity noise which is common on both orders can be eliminated.

The sensors described herein can be used with various AFM systems and methods to measure, for example, the attractive and repulsive forces experienced by the tip to provide information on various surface forces and sample properties. Moreover, the force sensors described herein can be used with several AFM methods, including nanoindentation, force modulation, ultrasonic AFM, pulsed force mode, and dynamic force spectroscopy that have been developed to characterize the visco-elastic properties of the material under investigation.

Thus, a force sensor for probe microscope for imaging is provided that can offer the unique capability for measuring interaction forces at high speeds with high resolution. In addition to optical interferometer, various integrated readout techniques including capacitive, piezoelectric or piezo-resistive can be used. Similarly, the actuators described herein can include a thin film piezoelectric actuator, a magnetic actuator, or a thermal actuator. Further, force sensors with multiple tips, where several sensing and actuation functions are implemented in the same device are also envisioned. Still further, electrical measurements, chemical measurements, information storage and nanoscale manipulations can be performed all while simultaneously obtaining topography images of the sample in gas or liquid media. As such, the sensors and the methods of imaging described herein open a new area in the field of probe microscopy. This new device can enable high speed imaging and provide images of elastic properties and surface conditions of the sample under investigation.

In one experimental embodiment, the micro-fabrication of the membrane-based probe arrays involves a four-mask process. Standard IC materials (silicon nitride, silicon oxide, titanium and gold) are used for the mechanical structures whereas a special polymer film (Unity-400) is used as a sacrificial layer in order to increase the gap between the membrane and the substrate without inducing excessive stress on the membranes. The fabrication process starts with a 500-550 µm-thick quartz wafer on top of which 80 nm thick gold diffraction gratings with periods of 3.3, 4.0 and 6.0 µm are formed using e-beam evaporation and a standard lift-off process with the first mask. A 20 nm thick titanium layer is used as an adhesion layer between the gold layer and the substrate.

After the definition of diffraction gratings, the Unity-400 sacrificial polymer is spun at 500 rpm with a ramping speed of 250 rpm for 5 seconds followed by another spinning at 400 rpm with a ramping speed of 100 rpm for 60 seconds. After the softbake on a hot plate at 105° C. for 8 minutes, a flat polymer layer with thickness of 3.2 µm is obtained. Unity-400 is a photo-definable sacrificial polymer, where the exposed area remains (cross-linked). Thus, mask #2 is used to pattern the film at the wavelength of 405 nm with an energy density of 60 mJcm$^{-2}$. Post-exposure baking takes place in an oven at 125° C. for 15-20 minutes followed by developing the film in the Avatrel developer. Isopropanol is used to rinse the wafer during the development process. The polymer is then cured inside the Lindbergh furnace at 160° C. for 1 hour. After curing, the polymer is thinned down to the thickness of ~1.9 µm by using O$_2$ plasma in an RIE chamber.

To define the probe membrane, first a 0.1 µm thick PECVD dielectric layer is deposited on top of the sacrificial layer at 300° C. The dielectric film consists of Si$_3$N$_4$/SiO$_2$ with a ratio of 0.84:1 to minimize the intrinsic stress built-up in the layer. Then an 80 nm thick gold layer is sputtered to define the top electrode. To promote the adhesion, a 5 nm thick titanium layer is used between the gold layer and the dielectric layer to prevent electrical shorting in case the membrane collapses. Mask #3 is used to pattern the Ti/Au layer properly. After metallization, another dielectric layer consisting of four sequencing layers of Si$_3$N$_4$, SiO$_2$, Si$_3$N$_4$ and SiO$_2$ with a total thickness of 1.5 µm is deposited. The ratio of Si$_3$N$_4$ to SiO$_2$ is maintained at 0.84:1 as before. The membrane is patterned using RIE etching with mask #4 to form etch holes necessary for the etching of the sacrificial layer.

It is possible to decompose the Unity-400 film by heating up the wafer to a temperature of 440° C. with a furnace that can supply a continuous flow of N2 gas at 5-10 sccm. Since the membrane is a multi-layered structure, buckling can occur during the decomposition step. Thus, the furnace is heated up very slowly to minimize buckling. Once the sacrificial layer is fully decomposed, the wafer is then diced into chips and the etch holes are sealed by using epoxy for sealing. Circular probe membranes with various diameters (50-600 µm) are fabricated.

The polymer sacrificial layer provides a gap of about 2 µm. The reflow of the soft polymer layer provides planarization and prevents the translation of the diffraction grating pattern to the membrane as seen from the surface profile. The surface roughness is due to both the definition of the Unity 400 film and the deposition of the dielectric membrane.

For the mechanical characterization, the stiffness of each membrane was measured experimentally using TriboIndenter (Hysitron Inc.), which showed that the stiffness of the fabricated membranes was dominated by residual tensile stress of 30 MPa. Accordingly, the stiffness values of the 100-600 µm membranes are from 600 to 1500 N$^{-1}$. Therefore, these membranes are suitable for actuation purposes, where the membrane can be considered rigid as compared to the AFM cantilevers (k~0.01-0.05 Nm$^{-1}$) used in the single-molecule mechanics experiments.

The above process is specific for silicon nitride and oxide membrane fabrication. Similar structures can be fabricated using different dielectric membrane materials to achieve desired stiffness values. For example, for higher force resolution, polymer membranes were also fabricated. These membranes are a combination of parylene and metal layers providing lower spring constant values. As a comparison, we measured the spring constant of a 200 μm diameter membrane as 20 Nm$^{-1}$ and it is feasible to achieve even softer polymer membranes with a spring constant of 1 N m$^{-1}$.

To use these active probes in single-molecule mechanics experiments, both the electrostatic actuation and optical interferometric detection capabilities should be well characterized. The electrostatic actuator should provide a suitable actuation range with a reasonable speed whereas the optical interferometer should be capable of resolving as small displacements as possible while providing enough dynamic range.

Figure 33:
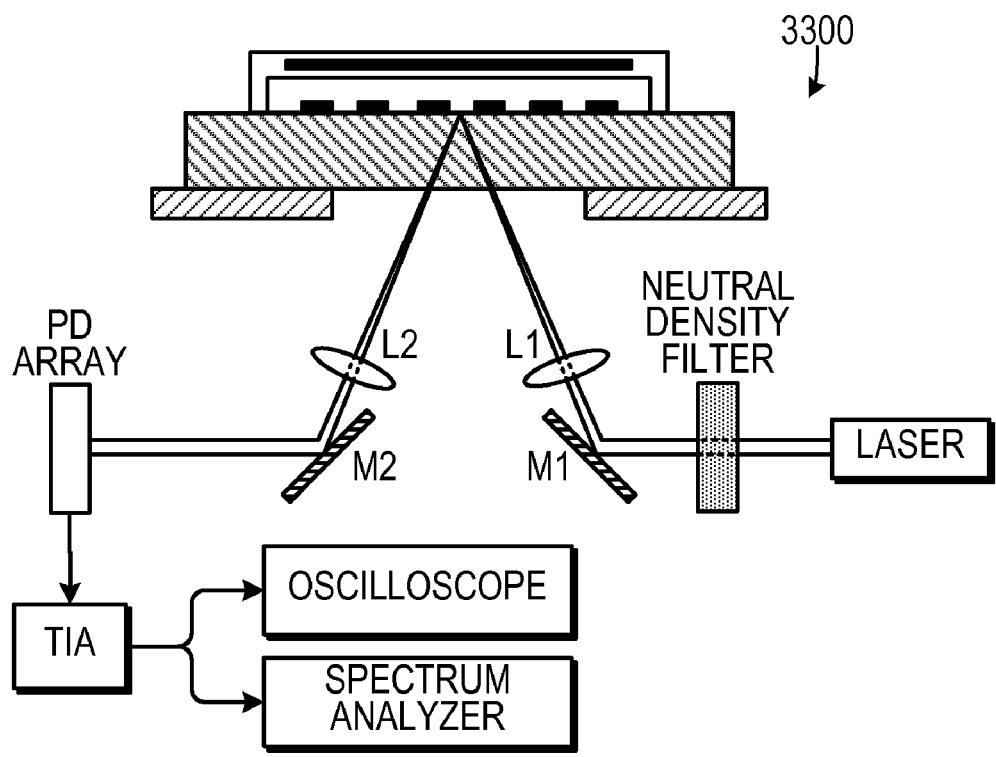
FIG. 33 is a schematic drawing of an experimental set-up for the characterization of membrane-based probes.

As shown in FIG. 33, an experimental set-up 3300 was used to characterize the probes. A low noise laser module supplied 5 mW laser light at 635 nm. The incident beam passed through a neutral density filter used to adjust laser power incident on the membranes. The beam was then deflected by an adjustable reflective mirror (M1) and focused on the membrane grating with a focusing lens (L1). The beam spot on the diffraction grating plane was approximately 30 μm. The light intensities in the 0th, +1$^{st}$ and −1$^{st}$ diffraction orders ($I_0$, $I_1$, and $I_{-1}$) were captured and collimated by a lens (L2) before they were directed onto a photodiode (PD) array (Hamamatsu, S4114-46Q) after reflection from a second mirror (M2). The photocurrent ($I_{pd}$) from the PD array was converted into a readout signal ($V_{pd}$) by transimpedance amplifiers (TIA) with a gain of 5 kV A$^{-1}$. The readout signal was fed into an oscilloscope (Tektronix, TDS2004), from which DC and modulated DC signals were monitored, and a dynamic signal analyzer (Stanford Research Systems, SR780, Sunnyvale, Calif.) was used for noise characterization.

For experimental characterization of the actuation performance, a 500 μm diameter transducer membrane with a diffraction grating period of 3.3 μm was used. The membrane was actuated by applying a voltage difference between the electrodes (top electrode and diffraction grating) while monitoring the intensity of light in the diffraction orders by the PD array. The intensity of the zeroth and first orders changed periodically as the gap height changed due to the applied voltage, as expected.

The same experiment was repeated under a white light interferometer to measure the membrane displacement as a function of applied bias voltage. Membrane displacement is proportional to the square of voltage and the experiment showed that, for a bias voltage of 50 V, the membrane was displaced by about 200 nm. Combining these data sets, the optical interference curve ($V_{pd}$) was mapped to the membrane displacement. The interference curve showed a nearly sinusoidal dependence to membrane displacement with a period of 210 nm.

The main noise sources in the overall optical detection system that determine minimum detectable displacement (MDD) can be listed as the shot noise in the photodetector, relative intensity noise (RIN) of the laser source, electronic noise of TIA and the thermo-mechanical noise of the membrane. MDD basically equals the displacement that is measured with a unity signal-to-noise ratio. For this experiment, the membrane was biased to its maximum sensitivity point and the noise was read from the PD outputs using a dynamic signal analyzer (Stanford Research Systems model # SR785). The differential readout scheme, subtracting the first-order signal from the zeroth-order signal by equating the DC levels, helped suppress the RIN. The displacement noise spectral density floor for the current system was below 10 fm Hz$^{-1/2}$ for frequencies as low as 3 Hz with the differential readout scheme. The noise suppression at the low frequency end (3-1000 Hz) is important since most bimolecular interaction measurements have significant signal components case can be due to several reasons including the membrane in this range. Overall, more than 20 dB noise suppression is curvature, the angular spectrum of the incident light beam achieved with differential detection.

For dynamic characterization, the transducer was excited with a small amplitude AC voltage (VAC) on top of the DC. Sensitivity is defined as the change it is expected to be low even in liquid media because of its in $V_{pd}$ divided by the change in membrane displacement.

A 200 μm diameter membrane with sealed etch holes was used for dynamic characterization. The resonant frequency of the membrane in air was 420 kHz, which dropped to 200 kHz when the membrane was operated in buffer solution. The flat response of the membrane in liquid up to resonant frequency exceeded the requirements of molecular force spectroscopy as the rupture events usually occur in a few tens of milliseconds.

The main noise sources in the overall optical detection system that determine minimum detectable displacement (MDD) can be listed as the shot noise in the photodetector, relative intensity noise (RIN) of the laser source, electronic noise of TIA and the thermo mechanical noise of the membrane. MDD essentially equals the displacement that is measured with a unity signal-to-noise ratio. For this experiment, the membrane was biased to its maximum sensitivity point and the noise was read from the PD outputs using a dynamic signal analyzer (Stanford Research Systems model # SR785). The differential readout scheme, subtracting the first-order signal from the zeroth-order signal by equating the DC levels, helped suppress the RIN. The displacement noise spectral density floor for the current system was below 10 fm Hz$^{-1/2}$ for frequencies as low as 3 Hz with the differential readout scheme. The noise suppression at the low frequency end (3-1000 Hz) is important since most biomolecular interaction measurements have significant signal components in this range. Overall, more than 20 dB noise suppression was achieved with differential detection. The shot noise in the photodetector for this intensity level was estimated to be about 2.3 fmHz$^{-1/2}$, and that the theoretical limit was approached for frequencies above 1000 Hz. These measurements show nearly an order of magnitude improvement, especially at low frequencies, as compared to the previously demonstrated interferometric methods.

The estimated thermo mechanical displacement noise of this membrane in air was well below the shot noise and it is expected to be low even in liquid media because of its large spring constant (1000 N m$^{-1}$). While the current MDD levels are suitable for actuator feedback, parylene membranes with spring constants of 1-10 N m$^{-1}$ can be used to implement sensors for force spectroscopy experiments.

Figure 29A:
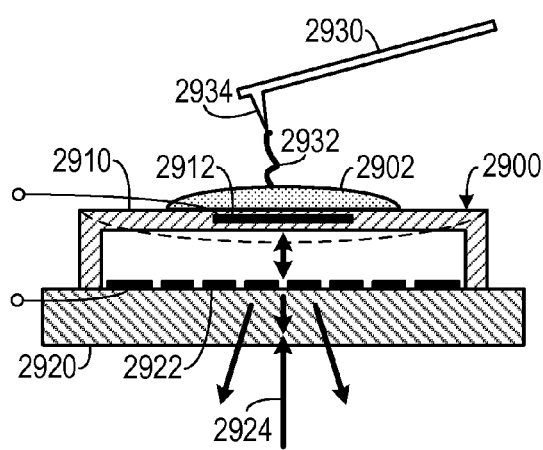
FIG. 29A is a schematic drawing of a flexible-surface electrostatic actuator operating with a sensing probe and an optical grating displacement sensor.

As shown in FIG. 29A, one embodiment of an apparatus for measuring a property (which can include any property that can be sensed) of a sample 2902 that includes a substrate 2920 and an actuation device 2900 disposed on the substrate 2920. The actuation device 2900 includes a flexible surface 2910 spaced apart from the substrate 2920 and configured so as to allow placement of the sample 2902 thereupon. The actuation device 2900 also includes a vertical actuator that is configured to cause the flexible surface to achieve a predetermined displacement from the substrate when a corresponding potential is applied thereto The vertical actuator, which in this embodiment is an electrostatic actuator, includes a first conductor 2912 that is coupled to the flexible surface 2910 and a second conductor 2922 that is coupled to the substrate. A potential is applied between the first conductor 2912 and the second conductor 2922 to control the displacement of the flexible surface 2910 relative to the substrate 2920.

A sensing probe 2934, which can be mounted on a cantilever 2930 or other probing structure (such as a FIRAT-type structure) is placed to interact with the sample 2902 thereby sensing the property of the sample. A molecule 2932 of a predetermined type may be attached to the probe 2934 to interact with the sample 2902. In the embodiment shown in FIG. 29A, the second electrode 2922 is also a diffraction grating that interacts with a light beam 2924 that reflects off of the bottom surface of the flexible surface 2910. The reflected beam provides feedback regarding the displacement of the flexible surface 2910.

Figure 29B:
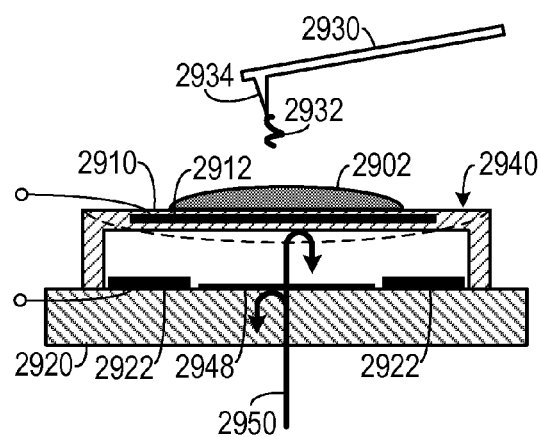
FIG. 29B is a schematic drawing of a flexible-surface electrostatic actuator operating with a sensing probe and a Fabry-Perot displacement sensor.

In an embodiment shown in FIG. 29B, a secondary partially-reflective reflector 1948 is integrated with the second electrode 2922 so that a Fabry-Perot cavity is formed between the first electrode 2912 and the second electrode 2922. A light beam 2950 can then provide displacement information through interferometry.

Figure 29C:
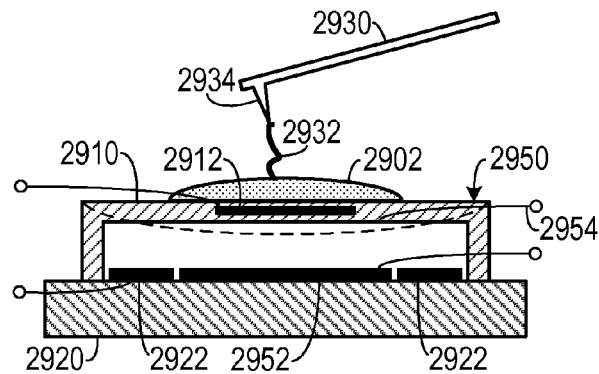
FIG. 29C is a schematic drawing of a flexible-surface electrostatic actuator operating with a sensing probe and a capacitive displacement sensor.

As shown in FIG. 29C, a capacitance sensor can be placed between a conductor 2952 disposed on the substrate 2920 and a conductor 2954 coupled to the flexible member 2910 to sense displacement as a function of capacitance.

In another embodiment, the vertical actuator is a piezoelectric actuator that that includes a piezoelectric member that is configured to achieve a desired displacement as a function of a potential being applied across the piezoelectric member.

As shown in FIG. 30, a feedback mechanism 3000 that monitors a displacement of the flexible surface 2910. The feedback mechanism 3000 can include a source 3010 that directs a beam of electromagnetic radiation toward the flexible surface 2910. A first reflective surface 3011 is disposed on the flexible surface 2910 and reflects a portion of the beam so as to form a reflected beam so that the reflected beam has a property that is indicative of the displacement of the flexible surface 2910. A sensor, which may be integrated with the source 3010 senses the property of the reflected beam. A controller 3016 receives displacement feedback from the sensor 3010 and from a force sensing detector 3012, which provides information about the position of the probe 2934. The controller 3016 controls a driver 3014 that applies a potential to the vertical actuator, thereby controlling displacement of the flexible surface 2910.

As shown in FIGS. 31A-31C, a plurality of actuation devices 3112 may be arranged on a substrate 3110 in an array 3100. The array 3100 may be driven by an x-axis actuator 3120 and a y-axis actuator 3122 (which may be part of a translation table). The lateral actuators 3120 and 3122 move the substrate relative to the sensing probe so that each of the plurality of actuation devices 3112, which move the sample along the z-axis, is accessible to the sensing probe. Each of the actuation devices 3112 may be independently addressable by the control circuit, so that displacement of each flexible surface of each of the actuation devices 3112 is independently controllable.

Figure 32A:
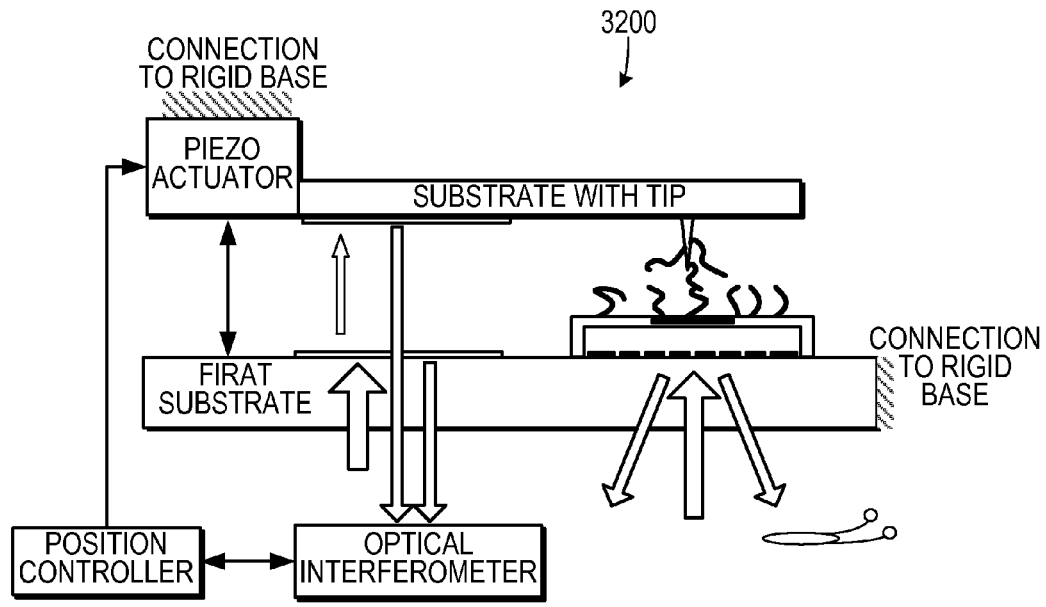
FIG. 32A is a schematic drawing of a sensing system employing a piezoelectrically-actuated probe sensor and an optical interferometer feedback system.
Figure 32B:
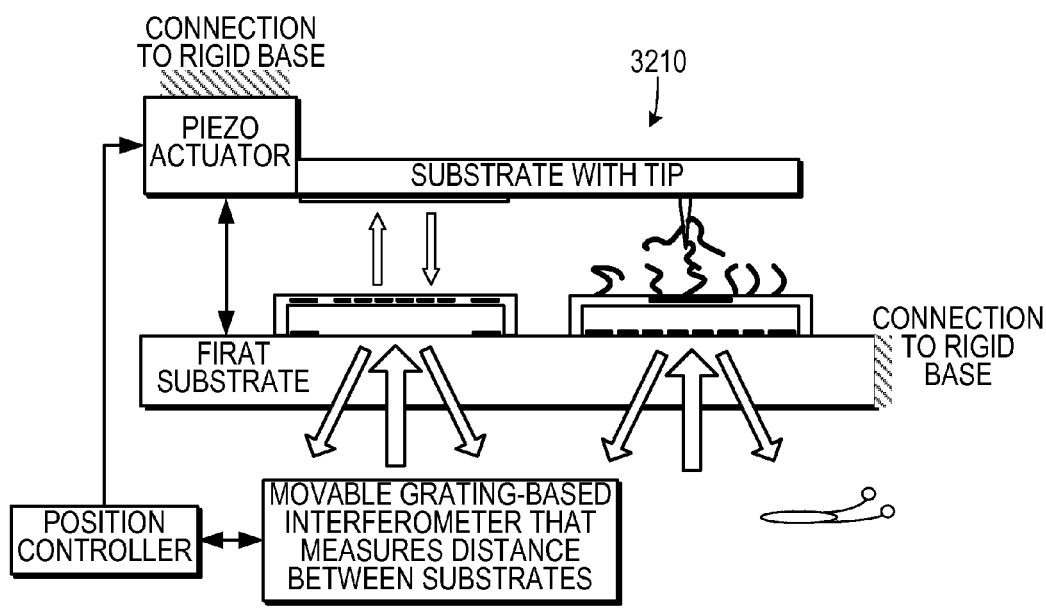
FIG. 32B is a schematic drawing of a sensing system employing a piezoelectrically-actuated probe sensor and a grating-based interferometer feedback system.
Figure 32C:
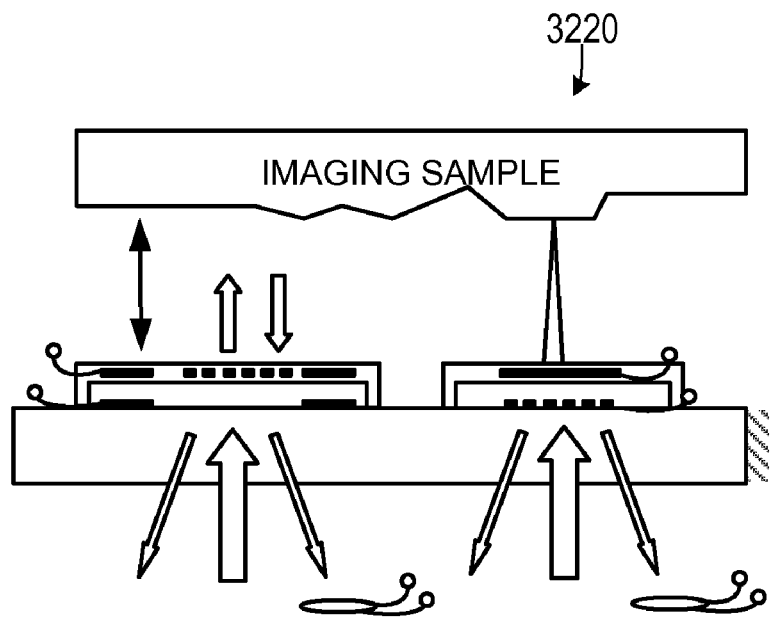
FIG. 32C is a schematic drawing of a sensing system in which a probe sensor is mounted on a flexible actuation structure.

One embodiment, as shown in FIGS. 32A-32C, encloses a probe microscope structure which includes a drift measurement and control system. The embodiment uses precise measurement of the distance between the sample surface and the rigid base of the force sensor, and feeding this information in real-time to the controller of a large scale actuator to keep the sample-force sensor distance at the desired value during measurement. In addition to reducing long term drift in the force measurements, this method may reduce the low frequency, vibration induced noise in scanning probe measurements and imaging. In summary, the scanning probe system has an independent substrate to substrate distance measurement and control system in addition to the force sensing probe. In contrast drift reducing methods which rely on sensors connected to the piezo actuator to close the control loop for the piezo actuator extension, the direct measurement of the sample-to-probe distance is used. The method is applicable to both contact and non-contact measurements and should be especially useful when imaging at low speeds.

In many experiments involving force measurements between two molecules which may be immobilized on a sharp tip, force sensing artificial or cell membrane, a functionalized beads, keeping the distance between the interacting objects during a portion of the measurement is critical. One example of that can be given as the distance dependent on rate measurement of molecular interactions between selectin and ligands. In this measurement, an AFM cantilever tip carrying one of the molecules is first brought into contact with the rigid surface coated with the other molecule using a piezo actuator. Then, the tip is retracted to a certain distance by the piezo actuator (e.g., 20 nm) and this distance is kept constant for a time which can be in the order of milliseconds to minutes. During this time, the force on the cantilever tip is monitored to record random bond formation events. This measurement can be repeated at different distances to vary the effective cross sectional area of molecular interactions.

Similarly, in some experimental embodiments, when a bond is formed, the molecule is extended to a certain distance and the time for bond rupture is measured. A problem arises when the piezo actuator drifts during the measurement due to thermal, mechanical changes in the system. This changes the distance between interacting samples, which needs to be kept constant to better than 1 nm during measurements. Some measurements rely on either open loop control of the piezo material, where a calibrated voltage is applied to the piezo to move a certain distance. Others, such as closed loop controlled systems, use a strain gage or a capacitive sensor integrated to the piezo actuator system to measure extension or contraction of the actuator. That information is then fed back to the controller to keep the extension of the piezo at a desired value, but the distance between the sample surface and a rigid surface of the force sensor is not measured.

One study used a similar idea where the tunneling current was measured and an interferometer was used to suppress the drift and low frequency noise using both sensors on a cantilever. This study demonstrated that by having two independent distance sensors one can eliminate the common noise and have a better topography image.

One embodiment combines a force sensor, a FIRAT probe, with an interferometric distance sensor on a rigid substrate, which can be transparent or can have an opening for optical access. Also, a movable grating can be used to optimize the distance sensor sensitivity using a FIRAT like optical readout. This could be useful for any SPM application of FIRAT that employs imaging with slow scan rates.

FIG. 32A shows one embodiment of a sensing system 3220 employing a FIRAT probe with independent distance measurement taking a molecular force spectroscopy case as an example. In this case, a rigid substrate with flat surface has the sharp tip with molecules and a reflective portion. The cavity between substrates may be filled with a suitable buffer solution. The rigid and transparent substrate has the FIRAT probe for force measurements and also a partially reflecting surface for optical interferometric measurements of the distance accurately. The distance information is fed back to the piezo actuator through a controller to keep the distance constant during the measurement. The FIRAT probe or the sharp tip can be scanned to form images while the feedback loop maintains the distance. Also, arrays of tips and individually actuated FIRAT membranes can be used to perform parallel measurements with low drift and noise.

FIG. 32B shows an embodiment of a sensing system 3210 where a movable grating formed on the same FIRAT substrate using the same fabrication process is used for distance measurement with optimized sensitivity. Thus, there are essentially two FIRAT based sensors, one of which is used as a microscale interferometer with tunable grating.

FIG. 32C shows an embodiment of a sensing system 3220 with the FIRAT probe based SPM imaging while the distance measurement to the sample is again performed by another grating based interferometer. One can fabricate and use arrays of these probes and interferometers to do fast imaging, alignment correction etc.

The sensing system of this present invention can be used in such mediums as air, other gasses, fluids and even a vacuum. Essentially, any medium in which the sample can withstand the environment may be employed with various embodiments of the present invention.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising."

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. An apparatus for sensing a property of a sample, comprising:
   a. means for actuating the sample using a flexible surface upon which the sample is placed;
   b. means for sensing a degree of actuation of the sample;
   c. means for controlling actuation of the sample; and
   d. means for sensing the property of the sample.

2. The apparatus of claim 1, wherein:
   a. the means for sensing the property of the sample includes an array of sensing probes that are each capable of sensing a property of a sample;
   b. the means for actuating the sample includes an array of actuation devices, each including a flexible surface that is spaced apart from a substrate, disposed so that each of the actuation devices is configured to interact with exactly one of the sensing probes; and
   c. the means for controlling actuation of the sample includes a control circuit for applying a potential to each of the actuation devices so as to control displacement of the flexible surface from the substrate.

3. The apparatus of claim 2, wherein each of the actuation devices is independently addressable by the control circuit, so that displacement of each flexible surface of each of the actuation devices is independently controllable.

4. The apparatus of claim 2, wherein the sample is disposed on the flexible surface of each of the actuation devices.

5. The apparatus of claim 2, further comprising a feedback mechanism that monitors a displacement of each of the flexible surfaces.

6. The apparatus of claim 5, wherein the feedback mechanism comprises:
   a. a source that directs a beam of electromagnetic radiation toward the flexible surface;
   b. a first reflective surface disposed on the flexible surface that reflects a portion of the beam so as to form a reflected beam so that the reflected beam has a property that is indicative of the displacement of the flexible surface; and
   c. a sensor that senses the property of the reflected beam.

7. The apparatus of claim 6, further comprising a diffraction grating that interacts with the reflected beam so as to generate a diffraction pattern that corresponds to the displacement of the flexible surface.

8. The apparatus of claim 6, further comprising a partially reflective surface disposed adjacent to the substrate and spaced apart from the first reflective surface so as to form a Fabry-Perot cavity therebetween, wherein the property sensed by the sensor comprises reflected beam intensity.

9. The apparatus of claim 5, wherein the feedback mechanism comprises:
   a. a first conductor disposed adjacent to the flexible surface;
   b. a second conductor spaced apart from the first conductor and adjacent to the substrate; and
   c. a capacitance sensor that senses a capacitance between the first conductor and the second conductor, the capacitance corresponding to the displacement of the flexible surface from the substrate.

10. The apparatus of claim 2, wherein the substrate comprises a transparent material.

11. The apparatus of claim 2, wherein each of the array of sensing probes comprises a probe tip affixed to a distal end of a cantilever beam.

12. The apparatus of claim 2, wherein the means for actuating the sample actuate along a z-axis and further comprising a lateral actuator that includes:
   a. an x-axis actuation member that moves the substrate along an x-axis that is transverse to the z-axis; and
   b. a y-axis actuation member that moves the substrate along a y-axis that is transverse to both the z-axis and the x-axis.

* * * * *